US008455222B2

(12) United States Patent
Takemoto et al.

(10) Patent No.: US 8,455,222 B2
(45) Date of Patent: Jun. 4, 2013

(54) BILIVERDIN FROM A NON-ANIMAL SOURCE

(75) Inventors: Jon Y Takemoto, North Logan, UT (US); Dong Chen, Logan, UT (US)

(73) Assignee: Utah State University, Logan, UT (US)

( * ) Notice: Subject to any disclaimer, the term of this patent is extended or adjusted under 35 U.S.C. 154(b) by 281 days.

(21) Appl. No.: 12/939,880

(22) Filed: Nov. 4, 2010

(65) Prior Publication Data

US 2011/0104728 A1    May 5, 2011

Related U.S. Application Data

(60) Provisional application No. 61/258,126, filed on Nov. 4, 2009.

(51) Int. Cl.
| | | |
|---|---|---|
| *C12P 17/18* | (2006.01) | |
| *C12N 9/02* | (2006.01) | |
| *C12N 9/10* | (2006.01) | |
| *C07D 207/44* | (2006.01) | |
| *C07H 21/04* | (2006.01) | |

(52) U.S. Cl.
USPC ........... 435/119; 435/189; 435/193; 548/518; 536/23.2

(58) Field of Classification Search
USPC ........... 435/119, 189, 193; 536/23.2; 548/518
See application file for complete search history.

(56) References Cited

U.S. PATENT DOCUMENTS

| 5,624,811 A | 4/1997 | Lang et al. | |
|---|---|---|---|
| 6,689,578 B2 * | 2/2004 | DeZwaan et al. | ............... 435/32 |
| 6,969,610 B2 | 11/2005 | Maines | |
| 7,504,243 B2 | 3/2009 | Pendrak et al. | |
| 8,344,019 B2 | 1/2013 | Pendrak et al. | |
| 2003/0027124 A1 | 2/2003 | Maines | |
| 2005/0209305 A1* | 9/2005 | Pendrak et al. | ............... 514/422 |
| 2009/0203762 A1 | 8/2009 | Pendrak et al. | |
| 2012/0142751 A1 | 6/2012 | Pendrak et al. | |

OTHER PUBLICATIONS

Bo et al., "The Coordinated Increased Expression of Biliverdin Reductase and Heme Oygenase-2 Promotes Cardiomyocyte Survival: a Reductase-Based Peptide Counters B-Adrenergic Receptor Ligand-Mediated Cardiac Dysfinction", The FASEB Journal, Sep. 27, 2010, vol. 25, p. 1-13, FASEB, Bethesda, MD.

Hoare & Datta, "Characteristics of L-Alanine: 4, 5-Dioxovaleric Acid Transaminase: An Alternate Pathway of Heme Biosynthesis in Yeast", Archives of Biochemistry and Biophysics, Feb. 15, 1990, vol. 227, No. 1, p. 122-129, Elsevier, Cambridge, MA.

Kapitulnik & Maines, "Pleiotropic Functions of Biliverdin Reductase: Cellular Signaling and Generation of Cytoprotective and Cytotoxic Bilirubin", Trends in Pharmacological Sciences, Mar. 2009, vol. 30, Issue 3, p. 129-137, Elsevier, Cambridge, MA.

Nakao et al., "Biliverdin Administration Prevents the Formation of Intimal Hyperlasia Induced by Vascular Injury", Circulation, Jul. 18, 2005, vol. 112, p. 587-591, American Heart Association, Dallas, TX.

Nagira et al., "Ischemia/Reperfusion Injury in the Monolayers of Human Intestinal Epithelial Cell Line Caco-2 and Its Recovery by Antioxidants", Drug Metabolism and Pharmacokinetics, Jul. 21, 2006, vol. 21, No. 3, p. 230-237, Tokyo, Japan.

(Continued)

*Primary Examiner* — Rosanne Kosson

(57) ABSTRACT

Methods for producing biliverdin in a microorganism, methods for producing biliverdin from a non-animal source, cells for producing biliverdin and methods for producing cells for producing biliverdin are disclosed.

11 Claims, 33 Drawing Sheets

OTHER PUBLICATIONS

Schneegurt, Mark; "δ-Aminolevulinic acid biosynthesis in *Ustilago maydis*", Journal of Basic Microbiology, Apr. 2005, vol. 45, Issue 2, p. 155-159, Wiley, Hoboken, NJ.

Sedlak & Snyder, "Bilirubin Benefits: Cellular Protection by Billiverdin Reductase Antioxidant Cycle", Pediatrics, Jun. 1, 2004, vol. 113, p. 1776-1782, American Academy of Pediatrics, Elk Grove Village, IL.

Sedlak et al., "Bilirubin and Glutathione have Complementary Antioxidant and Cytoprotective Roles", PNAS, Mar. 31, 2009, vol. 106, No. 13, p. 5171-5176, The National Academy of Sciences of the USA, Washington, DC.

Wang et al., "Bilirubin Can Induce Tolerance to Islet Allografts", Endocrinology, Oct. 27, 2005, vol. 147, No. 2, p. 762-768, The Endocrine Society, Chevy Chase, MD.

Yamashita et al.,"Biliverdin, a Natural Product of Herne Catabolism, Induces Tolerance to Cardiac Allografts", The FASEB Journal, Feb. 20, 2004, vol. 18, p. 765-767, FASEB, Bethesda, MD.

Boffelli et al., "Comparative Genomics at the Vertebrate Extremes", Nature Reviews: Genetics, Jun. 2004, vol. 5, p. 456-465, Nature Publishing Group, London, UK.

Krogh et al.,"Hidden Markov Models in Computational Biology: Application to Protein Modeling UCSC-CRL-93-32", Journal of Molecular Biology, Aug. 17, 1993, vol. 235, p. 1501-1531, Elsevier, Cambridge, MA.

Sharp & Li, "The Codon Adaptation Index—A Measure of Directional Synonymous Codon Usage Bias, and its Potential Applications", Nucleic Acids Research. Jan. 1987, vol. 15, No. 3. p. 1281-1295, IRL Press Limited, Oxford, UK.

Ikemura, "Correlation between the abundance of *Escherichia coli* transfer RNAs and the occurrence of the respective codons in its protein genes: A proposal for a synonymous codon choice that is optimal for the *E. coli* translational system", Journal of Molecular Biology, Sep. 25, 1981, vol. 151, Issue 3, p. 389-409, Acedemic Press Inc. Ltd., London, UK.

Link et al., "Methods for Generating Precise Deletions and Insertions in the Genome of Wild-Type *Escherichia coli*: Application to Open Reading Frame Characterization", Journal of Bacteriology, Oct. 1997, vol. 179, No. 20, p. 6228-6237, American Society for Microbiology, Washington, DC.

* cited by examiner

```
ATGAGTGTCAACTTAGCTTCCCAGTTGCGGGAAGGGACGAAAAAATCCCACTCCATGGCGGAGA
ACGTCGGCTTTGTCAAATGCTTCCTCAAGGGCGTTGTCGAGAAAAATTCCTACCGTAAGCTGGT
TGGCAATCTCTACTTTGTCTACAGTGCCATGGAAGAGGAAATGGCAAAATTTAAGGACCATCCC
ATCCTCAGCCACATTTACTTCCCCGAACTCAACCGCAAACAAAGCCTAGAGCAAGACCTGCAAT
TCTATTACGGCTCCAACTGGCGGCAAGAAGTGAAAATTCTGCCGCTGGCCAAGCCTATGTGGA
CCGAGTCCGGCAAGTGGCCGCTACGGCCCCTGAATTGTTGGTGGCCCATTCCTACACCCGTTAC
CTGGGGGATCTTTCCGGCGGTCAAATTCTCAAGAAAATTGCCCAAAATGCCATGAATCTCCACG
ATGGTGGCACAGCTTTCTATGAATTTGCCGACATTGATGACGAAAAGGCTTTTAAAAATACCTA
CCGTCAAGCTATGAATGATCTGCCCATTGACCAAGCCACCGCCGAACGGATTGTGGATGAAGCC
AATGACGCCTTTGCCATGAACATGAAAATGTTCAACGAACTTGAAGGCAACCTGATCAAGGCGA
TCGGCATTATGGTGTTCAACAGCCTCACCCGTCGCCGCAGTCAAGGCAGCACCGAAGTTGGCCT
CGCCACCTCCGAAGGCTAATAA
```

FIG. 6

```
ATGGACTACAATCTGGCACTCGATACCGCTCTGAACCGGCTCCATACCGAGGGCCGGTACCGGA
CCTTCATCGACATCGAGCGGCGCAAGGGTGCCTTCCCGAAAGCCATGTGGCGCAAGCCCGACGG
GAGCGAGAAGGAAATCACCGTCTGGTGCGGCAACGACTATCTCGGCATGGGCCAGCATCCGGTG
GTGCTGGGGGCCATGCACGAGGCGCTGGATTCGACCGGCGCCGGGTCGGGCGGCACGCGCAACA
TCTCGGGCACCACGCTCTATCACAAGCGCCTCGAGGCCGAGCTCGCCGACCTGCACGGCAAGGA
AGCGGCGCTGGTCTTCTCGTCGGCCTATATCGCCAACGACGCGACCCTCTCGACGCTGCCGCAG
CTGATCCCGGGCCTCGTCATCGTCTCGGACAAGTTGAACCACGCTTCGATGATCGAGGGCATCC
GCCGCTCGGGCACCGAGAAGCACATCTTCAAGCACAATGACCTCGACGACCTGCGCCGGATCCT
GACCTCGATCGGCAAGGACCGTCCGATCCTCGTGGCCTTCGAATCCGTCTATTCGATGGATGGC
GACTTCGGCCGCATCGAGGAGATCTGCGACATCGCCGACGAGTTCGGCGCGCTGAAATACATCG
ACGAGGTCCATGCCGTCGGCATGTACGGCCCCGCGGCGGCGGCGTGGCCGAGCGGGACGGGCT
GATGGACCGGATCGACATCATCAACGGGACGCTGGGCAAGGCCTATGGCGTGTTCGGCGGCTAT
ATCGCGGCCTCGTCAAAGATGTGCGACGCGGTGCGCTCCTACGCGCCGGGCTTCATCTTCTCGA
CCTCGCTGCCGCCCGTCGTGGCGGCCGGTGCGGCGGCCTCGGTGCGCCACCTCAAGGGCGATGT
GGAGCTGCGCGAGAAGCACCAGACCCAGGCCCGCATCCTGAAGATGCGCCTCAAGGGGCTCGGC
CTGCCGATCATCGACCACGGCTCGCACATCGTGCCGGTCCATGTGGGCGACCCCGTGCACTGCA
AGATGATCTCGGACATGCTGCTCGAGCATTTCGGCATCTATGTCCAGCCGATCAACTTCCCGAC
CGTGCCGCGCGGGACCGAGCGGCTGCGCTTCACCCCGTCGCCCGTGCATGATTCCGGCATGATC
GATCACCTCGTGAAGGCCATGGACGTGCTCTGGCAGCACTGTGCGCTGAATCGCGCCGAGGTCG
TTGCCTGA
```

FIG. 7

```
                        10         20         30         40         50         60         70         80
                 ....|....|....|....|....|....|....|....|....|....|....|....|....|....|....|....|
SEQ ID NO:11   2 TNLAQKLRYGTQQSHTLAENTAYMKCFLKGIVEREPFRQLIANLYLYSALEAALRQHRDNEIISAIYFP-ELNRTDKLA  80
SEQ ID NO:10   6 AGLAVELKQSTAQAHEKAEHSTFMSDLLKGRLGVAEFTRLQEQAWLFYTALEQAVDAVRASGFAESLLDP-ALNRAEVLA  84
SEQ ID NO:16   1 ----MRERTKTLHVTAERTGVVAELLRGRGTVRAYALLLRNLLPVYEALEAELVRHQASPVVGLTVRP-ELHRCPAIK  73
SEQ ID NO:18   2 DSFSTLIRTASHQQHVEAETSTFMSDLLGGLGVDAYARYTEQLMFVYEALEAAAGRLAADPVAGPFVRP-ELLRLASLE  80
SEQ ID NO:17   6 SPALAALRDATRDLHAELDRRSPLGD---DDLDDRAYLDHAGRILGWIEPLERALRDNRSGWPAALRADA-RLVKSTWLE  81
SEQ ID NO:13  13 LR-SQRLNLLTNEPHQRLESLVKSKEPF---ASRDNFARFVAAQYLFQHDLE-------------PLYRNEALA  69
SEQ ID NO:15  25 MAFTKELRKATKDVHNLTDVLVNAKIALALSDDEVWYDGLLA-FYELYKFFETHLPER--------LLPKEFHRTAAFE  94
SEQ ID NO:12  27 ADLSELLKEGTKEAHDRAENTKFVKDFLKGNIKKEIFKLATTALYFTYSALEEEMDRNKDHPAFAPLYFPMELHRKEALT 106
SEQ ID NO:14  15 RDLSEQIKKVTKDVHVRAESTELMLSFQRGQVTLQQYKLLCSLYEIYLALEEEMDRNCDHPSVAPIYFPAELARLATIE  94
SEQ ID NO:20  11 QDLSEALKEATKEVHTQAENAEFMRNFQKGQVTRDGFKLVMASLYHIYVALEEIERNKESPVFAPVYFPEELHRKAALE  90

90        100        110        120        130        140        150        160
                 ....|....|....|....|....|....|....|....|....|....|....|....|....|....|....|....|
SEQ ID NO:11  81 EDLTYYY-G-PNWQQIIQPTPCAKIYVDRLKTIAAS---EPELLIAHCYTRYLGDLSGGQSLKN-------------- 139
SEQ ID NO:10  85 RDLDKLNGS-SEWRSRITASPAVIDYVNRLEEIRDNV--DGPALVAHHYVRYLGDLSGGQVIAR-------------- 145
SEQ ID NO:16  74 ADLAALD-A----SDLLPEAIAYVRAIQEAGSG---SGHPLLAHAYTRYLGDLSGGQIIKK-------------- 128
SEQ ID NO:18  81 RDLAHLR-G-ADWRTGLTALPATEAYAARVRECAEE---WPAGYVANHYTRYLGDLSGGQIIRD-------------- 139
SEQ ID NO:17  82 SDL--LA-G-----GMSRAQVEALPRCADLPNAT--RAAEVFGVAYVMEGATLGGAYLYKR-------------- 132
SEQ ID NO:13  70 RLFPGLA-SRARDDAARADIADLGHPVPEGDQSVREADLSIAEALGWLFVSEGSKLGAAFLFKK-------------- 132
SEQ ID NO:15  95 RDFAYFY-G-SDWRKDYEIRPAVQKYLEHLEKIAAQ---NELLLFAYSYQMYALMSGGQMLQKKRMIARKMWIFSKNDD 169
SEQ ID NO:12 107 KDMEYFF-G-ENWEEQVQCSEAAQKYVERIHYIGQN---EPELLVAHAYTRYMGDLSGGQVLKK-------------- 165
SEQ ID NO:14  95 KDLEFFF-G-PDWREKIVVPAATERYCHRIRQIGQE---NPEYLIAHAYTRYLGDLSGGQVLGR-------------- 153
SEQ ID NO:20  91 QDLAFWY-G-PRWQEVIPYTPAMQRYVKRLHEVGRT---EPELLVAHAYTRYLGDLSGGQVLKK-------------- 149
```

FIG. 16A

```
SEQ ID NO:11   140 ------------------------------IIRSALQLPEG-EGTAMYEFDSLPTPGDRRQFKEIYRDVLNSLPLDEA 186
SEQ ID NO:10   146 ------------------------------MMQRHYGVDPE--ALGFYHFEGIA---KLKVYKDEYREKLNNLELSDE 188
SEQ ID NO:16   129 ------------------------------ILARSLELQPE--ALSFYEFPAIT---DIPRFKTEYREALEQAGSAMT 171
SEQ ID NO:18   140 ------------------------------KAERTWGFARKGDGVRFYVFEEIS---NPAAFKREYRDLLDGIRADDL 184
SEQ ID NO:17   133 ------------------------------LAPRLPGLPLQ---WLQGYGQ-----ATGVRWQEFLEQLARQIDSPE  171
SEQ ID NO:13   133 ------------------------------AAALELDENFGARHLAEPEG-----GRAQGWKSFVAILDGIELNEE   173
SEQ ID NO:15   170 EEQQKQADKEAELATARAADGSVKDDLEARPMPAQVTICPPGCEATYFPEKISVLKAKLRRVFNNHYGA-----FDDD 243
SEQ ID NO:12   166 ------------------------------VAQRALKLPSTGEGTQFYLFENVD---NAQQFKQFYRARMNALDLNLK 210
SEQ ID NO:14   154 ------------------------------IAQKSMKLGGS-EGLSFFAFPGVS---SPNLFKRLYRSRMNSVELTEE 197
SEQ ID NO:20   150 ------------------------------IAQKALDLPSSGEGLAFFTFPNIA---SATKFKQLYRSRMNSLEMTPA 194

SEQ ID NO:11   187 TINRIVEEANYAFSLNREVMHD 208
SEQ ID NO:10    89 QREHLLKEATDAFVFNHQVFAD 210
SEQ ID NO:16   172 EHDSVVEEAATAFQLNITLSQA 193
SEQ ID NO:18   185 EKQRVAECKRAFALNTAVFRA  206
SEQ ID NO:17   172 AIGLAQDAAQATFLSFRRWVLD 193
SEQ ID NO:13   174 EERLAAKGASDAFNRFGDLLER 195
SEQ ID NO:15   244 LRAAFIEESRNVFRLNIEVVRT 265
SEQ ID NO:12   211 TKERIVEEANKAFEYNMQIFSE 232
SEQ ID NO:14   198 QRSAVLQEALGAFEFNIQVFED 219
SEQ ID NO:20   195 VRQRVIEEAKTAFLLINIQLFEE 216
```

FIG. 16B

| | | |
|---|---|---|
| SEQ ID NO:1 | 1 | MSVNLASQLREGTKKSHSHSMAENVGFVKCFLKGVEKNSYRKLVGNLYFVYSAMEEEMAKF 60 |
| SEQ ID NO:7 | 1 | MSVNLATMLREGTKKSHSHTMAENVGFVKCFLKGVEKNSYRTLVANLYFVYSAMEEEMEKL 60 |
| SEQ ID NO:8 | 1 | MVANLATMLREGTKTSHTMAENVGFVKCFLKGVEKKSYRKLVADLYVVSAMEEEMERL 60 |
| SEQ ID NO:9 | 1 | MSSNLANKLRVGTKKAHTMAENVGFVKCFLKGVEKSSYRKLVANFYVYSAMEEEMEKH 60 |
| SEQ ID NO:1 | 61 | KDHPILSHIYFPELNRKQSLEQDLFYYGSNWRQEVKISAAGQAYVDRVRQVAATAPELL 120 |
| SEQ ID NO:7 | 61 | RHHELVSKIYFPQLHRKQSLEKDLCFYYGANWRNEVAPSKAAQAYVARIHEVAQTQPELL 120 |
| SEQ ID NO:8 | 61 | KDHPVVSQIYFPELNRKQSLETDLRYFGPNWQAEAKITPAGQAYVDRIHEVAQTAPELL 120 |
| SEQ ID NO:9 | 61 | SQHPIVSKINFSQLNRKQTLEQDLSYYGANWREQIQLSPAGEAYVQRIREISATEPELL 120 |
| SEQ ID NO:1 | 121 | VAHSYTRYLGDLSGGQILKKIAQNAMNLHDGGTAFYEFADIDDEKAFKNTYRQAMNDLPI 180 |
| SEQ ID NO:7 | 121 | AAHSYTRYLGDLSGGQILKKIAQRAMNLGENGGTAFYEFETISDEKAFKNEYRQALNELP 180 |
| SEQ ID NO:8 | 121 | VSHSYTRYLGDLSGGQILKKIAQNAMNLDGEGTAFYEFENISDEKAFKDKYRAAMNSLDV 180 |
| SEQ ID NO:9 | 121 | IAHSYTRYLGDLSGGQILKNIAVTAMNLNDGQGTAFYEFADISDEKAFKAKYRQTLDELA 180 |
| SEQ ID NO:1 | 181 | DQATAERIVDEANDAFAMNMKMFNELEGNLIKAIGIMVFNSLTRRRSQGSTEVGLATSEG 240 |
| SEQ ID NO:7 | 181 | IDEATAEKIVDEANAAFGMNMKMFMELEGNLIKAIGIMLFNTLTRRRSKGSTELAGAEQ 239 |
| SEQ ID NO:8 | 181 | PEETAEQIVQEANDAFGMNMNMFKELEGNLVKAIGVMLFNTLTRRRTKGSTDADLSPASN 240 |
| SEQ ID NO:9 | 181 | IDEATGDRIVDEANAAFGMNMKMFQELEGNLIKAIGMMLFNTLTRKRTRGATELATAE 238 |

FIG. 17A

```
SEQ ID NO:20    1                                                     MERPQPD--------SMP   10
SEQ ID NO:27    1                                                     MERPQPD--------SMP   10
SEQ ID NO:28    1   MERPQPDRQAPGAGRGARGAGRGVRALSPGWAAPARRREAPSPSSFGFGLRGGRVSVCMP           60
SEQ ID NO:19    1                                                     MERPQPDS-------SMP   11
SEQ ID NO:21    1                                                     MERPQPD--------SMP   10
SEQ ID NO:22    1                                                     MERPQLD--------SMS   10
SEQ ID NO:25    1                                                     METSQPHNAE-----SMS   13
SEQ ID NO:26    1                                                     MDSTKSKAAE-----NTG   13

SEQ ID NO:20   11   QDLSEALKEATKEVHTQAENAEFMRNFQKGQVTRDGFKLVMASLYHIYVALEEEIERNKE          70
SEQ ID NO:27   11   QDLSEALKEATKEVHTQAENAEFMRNFQKGQVTRDGFKLVMASLYHIYVALEEEIERNKE          70
SEQ ID NO:28   61   QDLSEALKEATKEVHTQAENAEFMKNFQKGQVTRKGFKLVMASLYHVYEALEEEIEHNRE         120
SEQ ID NO:19   12   QDLSEALKEATKEVHTQAENAEFMKNFQKGELTQEGFKLVMASLYHIYVALEEEIERNKE          71
SEQ ID NO:21   11   QDLSEALKEATKEVHIQAENAEFMKNFQKGQVSREGFKLVMASLYHIYTALEEEIERNKQ          70
SEQ ID NO:22   11   QDLSEALKEATKEVHIRAENSEFMRNFQKGQVSREGFKLVMASLYHIYTALEEEIERNKQ          70
SEQ ID NO:25   14   QDLSELLKEATKEVHEQAENTPFMKNTPFMKNFQKGQVSLHEFKLVTASLYFIYSALEEEIERNKD          73
SEQ ID NO:26   14   SDLSEQIKAVTKDSHVRAENTQLMLSYQKGQITQTQYKLLLCSLYEIYRALEEELDRNAD          73

SEQ ID NO:20   71   SPVFAPVYFPEELHRKAALEQDLAFWYGPRWQEVIPYTPAMQRYVKRLHEVGRTEPELLV         130
SEQ ID NO:27   71   SPVFAPVYFPEELHRKAALEQDLAFWYGPRWQEVIPYTPAMQRYVKRLHEVGRTEPELLV         130
SEQ ID NO:28  121   NPVYAPLYFPEELHRKAALERDMAFWYGPRWHEAIPYTQATRRYVQRLQEVGRREPELLV         180
SEQ ID NO:19   72   NPVYTPLYFPEELHRRASLEQDMAFWYGPRWQEAIPYTQATKRYVQRLQEVGRTEPELLV         131
SEQ ID NO:21   71   NPVYAPLYFPEELHRRAALEQDMAFWYGPHWQEIIPCTPATQHYVKRLHEVGRTHPELLV         130
SEQ ID NO:22   71   NPVYAPLYFPEELHRRAALEQDMAFWYGPHWQEAIPYTPATQHYVKRLHEVGGTHPELLV         130
SEQ ID NO:25   74   NPVYAPVYFPMELHRKAALEKDLEYFYGSNWRAEIPCPEATQKYVERLHVVGKKHPELLV         133
SEQ ID NO:26   74   HPAVQPIYFPQELARLEALGQDLEHFFGPQWRKRITVPAATHRYAQRLREIGKSSPELLV         133

SEQ ID NO:20  131   AHAYTRYLGDLSGGQVLKKIAQKALDLPSSGEGLAFFTFPNIASATKFKQLYRSRMNSLE         190
SEQ ID NO:27  131   AHAYTRYLGDLSGGQVLKKIAQKALDLPSSGEGLAFFTFPNIASATKFKQLYRSRMNSLE         190
SEQ ID NO:28  181   AHAYTRYLGDLSGGQVLKKIAQKALDLPSSGEGVDFFTFPNIASATKFKQLYRSRMNSLE         240
SEQ ID NO:19  132   AHAYTRYLGDLSGGQVLKKIAQKALNLPSSGEGLAFFTFPNIASATKFKQLYRSRMNTLE         191
SEQ ID NO:21  131   AHAYTRYLGDLSGGQVLKKIAQKAMALPSSGEGLAFFTFPNIDSPTKFKQLYRARMNTLE         190
SEQ ID NO:22  131   AHAYTRYLGDLSGGQVLKKIAQKAMALPSSGEGLAFFTFPSIDNPTKFKQLYRARMNTLE         190
SEQ ID NO:25  134   AHAYTRYLGDLSGGQVLGGQVLKKIAQKALQLPSTGEGLAFFTDGVSNATKFKQLYRSRMNALE         193
SEQ ID NO:26  134   AHAYTRYLGDLSGGQVLGKITQKSLGL-TGNKGILFFSFPGVTSANRFKQLYRSRMNSIE         193
```

FIG. 17B

```
SEQ ID NO:20   191  MTPAVRQRVIEEAKTAFLLNIQLFEELQELLTHDTKDQSPSRA-PGLRQRASNKVQDSAP  249
SEQ ID NO:27   191  MTPAVRQRVIEEAKTAFLLNIQLFEELQELLTHDTKDQSPSRA-PGLRQRASNKVQDSAP  249
SEQ ID NO:28   241  MTPEVRQRVIEEAKTAFLLNIQLFEELQELLSKDTEDQSPSQA-SGLRQRVGSRAQDSTP  299
SEQ ID NO:19   192  MTPEVRQRVLDEAKTAFLLNIQLFEELQGLLTQKAKDHDPLQA-PELHRRAGSKVQDLAP  250
SEQ ID NO:21   191  MTPEVKHRVTEEAKTAFLLNIELFEELQVMLTEEHKDQSPSQM-ASLRQRPASLVQDTAP  249
SEQ ID NO:22   191  MTPEVKHRVTEEAKTAFLLNIELFEELQALLTEEHKDQSPSQT-EFLRQRPASLVQDTTS  249
SEQ ID NO:25   194  MDHATKKRVLEEAKKAFLLNIQVFEALQKLVSKSQENGHAVQPKAELRTRSVNKSHENSP  253
SEQ ID NO:26   194  FTEQKRQEALDEAVRAFEFNIDVFDDLQKMLSITEEASSDK------------------  233

SEQ ID NO:20   250  V----ETPRGKPPLNT-RSQAPLLRWVLTLSFLVATVAVGLYAM  288
SEQ ID NO:27   250  V----ETPRGKPPLNT-RSQAPLLRWVLTLSFLVATVAVGLYAM  288
SEQ ID NO:28   300  A----ETPRGKPQLNL-PSQAPLLRWVLTLSFLVATVAVGLYVM  338
SEQ ID NO:19   251  T----KASRGKPQPSV-LSQAPLLRWVLTLSFLVATVAVGLYAM  289
SEQ ID NO:21   250  A----ETPRGKPQISTSSSQTPLLQWVLTLSFLLATVAVGIYAM  289
SEQ ID NO:22   250  A----ETPRGKSQISTSSSQTPLLRWVLTLSFLLATVAVGIYAM  289
SEQ ID NO:25   254  AAGKESERTSRMQADMLTTSPLVRWLLALGFIATTVAVGLFAM  296
SEQ ID NO:26   234  -----GNEAASQSLSKTFSSSPALQFALGVGITLATVGMGVYAF  272
```

FIG. 17C

| | | | |
|---|---|---|---|
| SEQ ID NO:23 | 1 | MATSRLNASCRFPASRRLDCESYVSLRAKTVTIRYVRTIAAPRRHLVRRANEDQTLVVNV | 60 |
| SEQ ID NO:24 | 1 | MATTRLNPSCHFPASTRLSCESYLGLRTTG-RISYARTLTAPRGYLAVKANGGQASVVTA | 59 |
| SEQ ID NO:23 | 61 | VAAAGEKPERRYPREPNGFVEEMRFVVMKIHPRDQVKEGKSDSNDL----VSTWNFTIEG | 116 |
| SEQ ID NO:24 | 60 | AAI-TEKQQKKYPGESKGFVEEMRFVAMRLHTKDQAREGEKESRSPEEGPVAKWEPTVEG | 118 |
| SEQ ID NO:23 | 117 | YLKFLVDSKLVFETLERIINESAIQAYAGLKNTGLERAENLSRDLEWFKEQGYEIPESMV | 176 |
| SEQ ID NO:24 | 119 | YLHFLVDSKLVYDTLEGIIDGSNFPTYAGFKNTGLERAESLRKDLEWFKEQGYEIPEPMA | 178 |
| SEQ ID NO:23 | 177 | PGKAYSQYLKNIAEKDPPAFICHFYNINFAHSAGGRMIGTKVAEKILDNKELEFYKWDGQ | 236 |
| SEQ ID NO:24 | 179 | PGKTYSEYLKDLAENDPQAFICHFYNIYFAHSAGGQMIGTKVSKKILDNKELEFYKWDGQ | 238 |
| SEQ ID NO:23 | 237 | LSELLQNVSEELNKVAELWTREEKNHCLEETEKSFKFYWEIFRYLLS | 283 |
| SEQ ID NO:24 | 239 | LSQLLQNVRQKLNKVAEWWTREEKSHCLEETEKSFKFSGEILRLILS | 285 |

FIG. 17D

```
SEQ ID NO:29    1 MQHLKAFEDALGAIHSEGRYRVFIDLHRHKGRFPKATARFEAGEREVTIWCSNDYLGMGQDDDVIKSMHEAIDSFGAGSG  80
SEQ ID NO:34    1 -MYQTLLSKKLSDLKASGQYRTFVTLNRICGQYPLAQLEGGDER-PVIVWCSNDYLGMSQHLVVRQAMHDAIDRYGAGSG  78
SEQ ID NO:44   14 RELRVLFEDRLTQLKSEGLYRSFMPCEHDASHPGTTRYRQR----QEVWCSNDYLGLSQDPQVIERLRESAALHSSGTG  89
SEQ ID NO:46    1 ------------------------------------------------MFCSNDYLGMSQNQEVINVMGDALKEYGAGAG  32
SEQ ID NO:36   16 ADTYAGLRAGLDKLRADGLYRDFVACSYLAEDRGHALHQGR----RIQVWCTNDYLGMSQHPDVMRAQIASTLRHSTGNG  91
SEQ ID NO:42    2 SNYSGVFAQALDTIKNEKRYREFVNLARISGEFPCAINEETNE--KIVIWCSNDYLGMGQNFTVCDSMKETIDRMGAGAG  79
SEQ ID NO:47    2 SNYSSVFARALDTIKNEKRYREFVNLARISGEFPCAINEETNE--KIVIWCSNDYLGMGQNFTVCDSMKETIDRMGAGAG  79
SEQ ID NO:41    1 MDFEKFFKDQINYLHHEKRYRFFTELAYEQYQFPYAIHNSDEGSRKVTIWCSNDYLGMGKHPKVIENAQRTFEKCIGAG  80
SEQ ID NO:37    2 VSYNNFFDNHLHSIKLEGRYRKFTCIKKSAKCFPYNICAQTGK--KVLIWCTNDYLGMSFHPEVLSSAVLAVKQMGVGAG  79
SEQ ID NO:30    2 LSYNNFFDNHLHSIKLEGRYRKFTCIKKSTKWFPYNICAQTGK--KVLIWCTNDYLGMSFHPEVLSSAVLAVKQMGVGSG  79
SEQ ID NO:2     1 MDYNLALDTALNRLHTEGRYRTFIDIERRKGAFPKAMWRKPDGSEKEITVWCGNDYLGMGQHPVVLGAMHEALDST-GAGSGG  82

SEQ ID NO:29   81 GTRNISGTTRFHVDLEQELADLHRKEAALLFTSGYVSNEATLSTLGKILPNLIIYSDALNHASMIEGIRRSGAEYRVFRH  160
SEQ ID NO:34   79 GSRNIGGSHGIFSQLERSLADWHSKEAALVFPTGFSSNDATLQCLLREIPDCVVISDEKNHASIINGIRATSTERQVFRH  158
SEQ ID NO:44   90 GSRNIAGTSISHVELERQLAQWHGKEQALVFNGGYTANFEFLSTLIAAVPDMAIFSDLNHRSLIEGIRRHPCQKFIFPH  169
SEQ ID NO:46   33 GSRNIGGSHKYFKLLENEIAKWHKKDSALVFPTGYSSNDASLQGLLRIFPEMIVFSDSKNHASIINALRSVKNKIEIFEH  112
SEQ ID NO:36   92 GSRNIAGTSEAHVELETLLAGWHAKERALVFNSGYVANVETLITTLLRAEPRTMVFSDALNHRSLIEGVRTSGNDKYFAH  171
SEQ ID NO:42   80 GTRNISGNNKEVVLLEKTIARLHQKEAALSFVCGYVANLASISTIISLMKDCIAFSDQCNHSSIIEGIRSSRCEKRIFRH  159
SEQ ID NO:47   80 GTRNISGNNKEVVLLEKTIAKLHQKEAALSFVCGYVANLASISTIISLMENCIAFSDQYNHSSIIEGIRTSRCEKRIFRH  159
SEQ ID NO:41   81 GTRNIAGTNYYHVMLEKELATLHGKEAALLFNSGYIANWATIGTLCSQIDNIICFSDSHNHASIIEGINKARCKKVIWNH  160
SEQ ID NO:37   80 GTRNIGGNNSAIVELEELLAILHKKQKALVFTSGYVANDTTLQTLAKIIPGLVFISDEYNHASIIAGIRNSRAEKHIYFH  159
SEQ ID NO:30   80 GTRNIGGNNSAIVELEELLAILHKKQKALVFTSGYVANDTTLQTLAKIIPGLVFISDEYNHASIIAGIRNSRAEKHIYFH  159
SEQ ID NO:2    83 GTRNISGTTLYHKRLEAELADLHGKEAALVFSSAYIANDATLSTLPQLIPGLVIVSDKLNHASMIEGIRRSGTEKHIFKH  162
```

FIG. 18A

```
                        170        180        190        200        210        220        230        240
                        ....|....|....|....|....|....|....|....|....|....|....|....|....|....|....|....|
SEQ ID NO:29    161 NDVDHLRALLELDDADRPKLIAFESVYSMDGDFGRMEEICDLAQEFNAITYLDEVHAVGMYGEQGAGVAEMLGLADRIDI 240
SEQ ID NO:34    159 NDLDHLEESLARYPLERPKIVFESVYSMDGDISPMAEIVDIAKQYNALTYLDEVHAVGMYGPRGAGLAAQLGIADKVDI 238
SEQ ID NO:44    170 NDVETLEKQLASVPLSQPKLIVFESIYSMDGDIAPIQVILDLADRYQAWTFLDETHAIGLYGGSGAGLCEEIE-ETRATF 248
SEQ ID NO:46    113 NNVKHLNELLNQYDINTPKLIVFESVYSMDGDIAPIVEIVELAKEYNSLTFLDEVHAIGMYGEEGRGYSDVVGVQEDIDI 192
SEQ ID NO:36    172 NDLTDLELALAAQPLDRPKLIVFESVYSMDGDVAPIREICDLAERYHAQTYLDETHAIGVLGPTGAGVCEEIG-ESRATF 250
SEQ ID NO:42    160 NDVNHLEELLSQVPREAHKIIIFESVYSMDGDVAPIKEICDLAEKYNALTYIDEVHAVGMYGRHGGITEEMDLVDRVDI 239
SEQ ID NO:47    160 NDVNHLEKLLSQVPKGAYKIIIFESIYSMDGDVAPIKEICDLAEKYNALTYIDEVHAVGMYGKHGGITEEMDLVDRVDI 239
SEQ ID NO:41    161 NDLEDLEKNLAATDLSIPKIIFESIYSMDGDIAPIKEICDLADQYNAITYIDEVHAVGIHGSCGAGISEREGIMNRITI 240
SEQ ID NO:37    160 NNMQSLQQILSSIPINQPKIIVFEAIYSMSGTIADVKGICNLAKMYNALTYIDEVHSVGLYGDDGSGICTLTGLFNQVDI 239
SEQ ID NO:30    160 NNMQSLQQILSSIPINQPKIIVFEAIYSMSGTIAAVKEICNLAKMYNALTYIDEVHSVGLYGDDGSGICTLTGLFNQVDI 239
SEQ ID NO:2     163 NDLDDLRRILTSIGKDRPILVAFESVYSMDGFGRIEEICDIADEFGALKYIDEVHAVGMYGPRGGVAERDGLMDRIDI 242

250        260        270        280        290        300        310        320
                        ....|....|....|....|....|....|....|....|....|....|....|....|....|....|....|....|
SEQ ID NO:29    241 MEGTLAKAYGVMGGYIASHSSVIDAIRSMASGFIFTTSTCPVMAAGALASIRKLRADEGRRLRAIHQDKAATLKQKFRDA 320
SEQ ID NO:34    239 IQGTMAKAIGVIGGYITGAQWLIDAVRSFSTGFIFTTSLPPVVAAGCLASIEHLKTQSQ--ERELLHTKTQQLRCALDSL 316
SEQ ID NO:44    249 IQGVFGKAMGTLGGYIAGPASVVDFVRSSAPGFIFTTALPQALLDATLCSFERVREDRQ--LVQDLHSNVIFFRAQLDAA 326
SEQ ID NO:46    193 IQSTMAKGIGIIGGYITGDQLLIDVIRSYSSGFIFTTALPPVIAAGCLTSIKIVRSNDK--LREELQDKTKYLKEKFKEN 270
SEQ ID NO:36    251 VQGVFGKAVGATGGYIGGYIAAKADIIDVVRSHASGFIFTTIPRASLDAALASLSVIRSPEGAGMRERLHANAELMRRLTEA 330
SEQ ID NO:42    240 IQGTLAKAYGVIGGYIAAKADIIDIIRSHASGFIFTTALPPVIASAGRASITHLYDSNE--ERRKQKENVAKLKAMFKAN 317
SEQ ID NO:47    240 IQGTLAKAYGVIGGYIAAKADIIDIIRSHASGFIFTTALPPVIASAGRASITHLYDSDE--ERRKQKENVAKLKAMFKAN 317
SEQ ID NO:41    241 ISGTLAKGFGTFGGYIAASENLCDFIRSFASGFIFSTSLPPAIASASVTSIQYIKQHYD--ERKKYLERVKQLRHSLENK 318
SEQ ID NO:37    240 IQGNLAKAYGAIGGYIAANSNIIDAIRSTASGFIFTTALPPVISCAAMTSIRYLMKSNK--ERLKLHETVSKLKDSLSNA 317
SEQ ID NO:30    240 IQGNLAKAYGAIGGYIAANSNIIDAIRSTASGFIFTTALPPVISCAAMTSIKYLMKSNK--ERLKLQETVAKLKDSLTSA 317
SEQ ID NO:2     243 INGTLGKAYGVFGGYIAASSKMCDAVRSYAPGFIFSTSLPPVVAAGAAASVRHLKGDVE---LREKHQTQARILKMRLKGL 321
```

FIG. 18B

```
                     330        340        350        360        370        380        390        400
                ....|....|....|....|....|....|....|....|....|....|....|....|....|....|....|....|
SEQ ID NO:29   321 GLPVME-SPSHIVLPLLVGDPERCKALSDTLLFDFGIYVQPINYPTVPRGTERLRFTPSPVHDEVMDELVAAILAVWKQL 399
SEQ ID NO:34   317 DIPVMSCSSTHVLPVLVGDAIKCKEAAERLLSVHGVYLQPINFPSVAAGTERFRVNVTPNHTDEQVTHLAEALREVFEHF 396
SEQ ID NO:44   327 GIPYLP-AQSHLVLVPVAGAERIKTVARRLLEEFDIYVQPINYPSVPRGGERFRLTVGPRRSHEEIQRFVAALKFCL--- 402
SEQ ID NO:46   271 GIEVLKQSKTHILPVIIGDSKKCEEAAKLLLGKFNIYDQAINSPTVEIGTERFRINVTPNHTKEQMDLLVSSIVYVFDFL 350
SEQ ID NO:36   331 GIAHVP-APTHLVPILVPGGNRVKRVSRRLLDEHSVYVQPINFPSVPKGGERFRVTVAPFRTEAQIEGFVEALARCL--- 406
SEQ ID NO:42   318 SIPYKD-APTHIIPVIIGHPEECKYASQTLLEEFKIFIQHINYPTVPRGTERLRITPTPQHTHTMMEELVFALKEVLGRI 396
SEQ ID NO:47   318 GIPYKD-APTHIIPVIIGHPEECKYASKTLLEEFKIFIQHINYPTVPRGTERLRITPTPQHTDTMMEELVFALKEVLGRI 396
SEQ ID NO:41   319 AIPCIP-NESHIPIMVGDSHKCTQISNILLKEFGIYIQPINYPTVAKKKERLRVTLTPLHTDSDIEHLVSSLENVWQKM  397
SEQ ID NO:37   318 GIRYLT-NNSHIIAIVIGEPVLTQRLAQILLEEYNIYIQAINFPTVPRGTERLRITPTPFHTDEMIHNLTVALKQVLLNL 396
SEQ ID NO:30   318 GIRYLT-NNSHIIAIVIGEPVLTQRVAQILLEEYNIYIQAINFPTVPRGTERLRITPTPFHTDGMIHNLTVALKQILLNL 396
SEQ ID NO:2    322 GLPIID-HGSHIVPVHVGDPVHCKMISDMLLEHFGIYVQPINFPTVPRGTERLRFTPSPVHDSGMIDHLVKAMDVLW--- 392

410
                ....|....|....:
SEQ ID NO:29   400 GLDKA---------A 405
SEQ ID NO:34   397 DIPLKTPPAFASAREAS 413
SEQ ID NO:44   403 ----A---------- 403
SEQ ID NO:46   351 NIRRSV---------- 356
SEQ ID NO:36   407 ADDPS---------- 411
SEQ ID NO:42   397 QHKKSAR-------GAV 406
SEQ ID NO:47   397 QHKKSAR-------GAI 406
SEQ ID NO:41   398 N-RYA---------- 401
SEQ ID NO:37   397 NISAAL--------G 403
SEQ ID NO:30   397 NIYAAL--------R 403
SEQ ID NO:2    393 -QHCALNRAEVVA 407
```

FIG. 18C

```
                           10         20         30         40         50         60         70         80
                  ....|....|....|....|....|....|....|....|....|....|....|....|....|....|....|....|
SEQ ID NO:2     1 MDYNLALDTALNRLHTEGRYRTFIDIERRKGAFPKAMWRKPDGSEKEITVWCGNDYLGMGQHPVVLGAMHEALDSTGAGS  80
SEQ ID NO:29    1 MQHLKAFEDALGAIHSEGRYRVFIDLHRHKGRFPKATARFEAGER-EVTIWCSNDYLGMGQDDDVIKSMHEAIDSFGAGS  79
SEQ ID NO:31    1 MSYDHFFADAVDALRRERRYRTFADVERDATRFPRATWHSPGGPR-EIVWCSNDYLGMGSHPAVVEAMRETALRRGAGA  79
SEQ ID NO:39    1 MDYKTAFASALDRVQAEGRYRVFADLKRHRGAFPRATWTKADGSESDVVWCSNDYLGQGQNPVVLDAMHRAIEAAGAGS  80
SEQ ID NO:38    1 MDYRVAFRTALENIRSEGRYRVFADLKRHRGAFPRATWTRADGSESDVVWCSNDYLGQGQNPVVLDAMHRAIEAAGAGS  80
SEQ ID NO:32    1 MDYKAAFRSAVEQIREEGRYRVFADLKRQRGQFPRATWTRQDGSEHEVVWCSNDYLGQGQNPVVLEAMKAAVDEHGSGS  80
SEQ ID NO:40    1 MDYKAAFRSAVEQIREEGRYRVFADLKRQRGQFPRATWTRQDGSEHEVVWCSNDYLGQGQNPVVLEAMKAAVDEHGSGS  80
SEQ ID NO:35    1 MDYKAAFRNTVDQIRDEGRYRVFADVKRHRGAFPRATWTRPDGGESEIVWCSNDYLGQGQNPLVLDAMHAAIDQHGSGS  80
SEQ ID NO:45    1 MDYRRFFEEAIDQLHAEKRYRVFADLERIVGRFPQAIWRNNGTAR-EITVWCSNDYLGMHHPDVIKAMCDTAGSAGSGA  79
SEQ ID NO:33    1 MDYRRFFEEAIDQLHAEKRYRVFADLERIVGRFPQAIWRNNGTAR-EITVWCSNDYLGMHHPDVIKAMCETAGSAGSGA  79
SEQ ID NO:43    1 MDYRRFFEEAIDQLHAEKRYRVFADLERIVGRFPQAIWRNNGTAR-EITVWCSNDYLGMHHPDVIKAMCETAGSAGSGA  79

90        100        110        120        130        140        150        160
                  ....|....|....|....|....|....|....|....|....|....|....|....|....|....|....|....|
SEQ ID NO:2    81 GGTRNISGTTLYHKRLEAELADLHGKEAALVFSSAYIANDATLSTLPQLIPGLVIVSDKLNHASMIEGIRRSGTEKHIFK 160
SEQ ID NO:29   80 GGTRNISGTTRFHVDLEQELADLHRKEAALLFTSGYVSNEATLSTLGKILPNLIIYSDALNHASMIEGIRRSG-AEYRVF 158
SEQ ID NO:31   80 GGTRNISGNSHEIVLLERELADLHGKEQGLVFTSGYVFTSGYVSNATGISTIAKLIPDCVISDELNHNNSMIEGVRQGG-RQKFIF 158
SEQ ID NO:39   81 GGTRNISGTTHYHVELERELADLHGKEAALLFTSGYVFTSGYVSNEATLSTLYKILPGLVVFSDALNHNNSMISGIRAGKREQRHVF 160
SEQ ID NO:38   81 GGTRNISGTTHYHVELERELADLHGKEAALLFTSGYVFTSGYVSNEATLSTLYKILPGLVVFSDALNHNNSMISGIRAGKREQRHVF 160
SEQ ID NO:32   81 GGTRNISGTNHDHVLLEQELADLHGKEAGLLFTSGYVSNEATLSVVQKILPGLIIFSDELNHASMIAGIRNGG-GPRKIF 159
SEQ ID NO:40   81 GGTRNISGTNHDHVLLEQELADLHGKEAGLLFTSGYVSNEATLSVVQKILPGLIIFSDELNHASMIAGIRNGG-GPRKIF 159
SEQ ID NO:35   81 GGTRNISGTNHHHVELEAELADLHGKEAALLFTSGYVSNEASLSALQKILPGLIIFSDAQNHASMIAGIRNGG-CQRHVF 159
SEQ ID NO:45   80 GGTRNISGNNHPLVELESELADLHGKEAGLVFTSGFVSNEASISTIARLLPNCLILSDELNHASMIEGVRRSG-AEKKIF 158
SEQ ID NO:33   80 GGTRNISGNNHPLVELESELADLHGKEAGLVFTSGFVSNEASISTIARLLPNCLILSDELNHASMIEGVRHSG-AEKKIF 158
SEQ ID NO:43   80 GGTRNISGNNHPLVELESELADLHGKEAGLVFTSGFVSNEASISTIARLLPNCLILSDELNHASMIEGVRRSG-AEKKIF 158
```

```
SEQ ID NO:2   320 --GLPIIDHGSHIVPVHVGDPVHCKMISDMLLEHFGIYVQPINFPTVPRGTERLRFTPSPVHDSGMIDHLVKAMDVLW-- 392
SEQ ID NO:29  319 DAGLPVMESPSHIVPLLVGDPERCKALSDTLLFDFGIYVQPINYPTVPRGTERLRFTPSPVHDEVMMDELVAAILAVWKQ 398
SEQ ID NO:31  316 AAGLPQMETPTHIVPVMVGDAKACKAASDVLLNEHNIYIQPINYPTVPRGTERLRITPTPFHNDKLIAHLADALNDVWNR 395
SEQ ID NO:39  319 AAGLPVMDSVSHIVPVLVGDPVHCKMISDILLEDHGIYVQPINFPTVPRGTERLRFTPSPAHTDAMMDALVAALETLWVR 398
SEQ ID NO:38  319 AAGLPVMDSVSHIVPVLVGDPVHCKMISDILLEDHGIYVQPINYPTVPRGTERLRFTPSPAHTDAMMDALVAALETLWVR 398
SEQ ID NO:32  318 AAGLPVMDSVSHIVPVLVGDPVHCKMISDMLLADFGVYVQPINYPTVPRGTERLRFTPTPFHTDDMMRKLVAAMEKLWAH 397
SEQ ID NO:40  318 AAGLPVMDSVSHIVPVLVGDPVHCKMISDMLLADFGVYVQPINYPTVPRGTERLRFTPTPFHTDDMMRKLVAAMEKLWAH 397
SEQ ID NO:35  318 AAGLPVMENDSHIVPVLVGDPVHCKLISDMLLADHGVYVQPINYPTVPRGTERLRFTPTPFHTDDMMRKLVGAMETLWAH 397
SEQ ID NO:45  317 AAGLPVMPSQTHIVPILVGDPELCKKASDRLLEVHGIYIQPINYPTVPRGTERLRITPSPLHDDKLIDGLKDALLEVWNE 396
SEQ ID NO:33  317 AAGLPVMPSQTHIVPILVGDPELCKKASDRLLEVHGIYIQPINYPTVPRGTERLRITPSPLHDDKLIDGLKDALLEIWNE 396
SEQ ID NO:43  317 AAGLPVMPSQTHIVPILVGDPELCKKASDRLLEVHGIYIQPINYPTVPRGTERLRITPSPLHDDKLIDGLKDALLEVWNE 396

SEQ ID NO:2   393 QHCALNRAEVVA 407
SEQ ID NO:29  399 LGLDKA------------------------------------------A 405
SEQ ID NO:31  396 LDLPRVRDTGSERRLVAAGAASLAMPTAGG                    425
SEQ ID NO:39  399 CNVVRVGG--------------------------------------MAA 409
SEQ ID NO:38  399 CNVKRVGG--------------------------------------VAA 409
SEQ ID NO:32  398 CNVARMGG--------------------------------------YAA 408
SEQ ID NO:40  398 CNVARMGG--------------------------------------YAA 408
SEQ ID NO:35  398 CNVARMGG--------------------------------------YAA 408
SEQ ID NO:45  397 LGIPFAEPSAPQAANSD-RIIPLMVSKAGG                    425
SEQ ID NO:33  397 LGIPFAEPSAPQAANSD-RIIPLMVSKAGG                    425
SEQ ID NO:43  397 LGIPFAEPSAPQAANSD-RIIPLMVSKAGG                    425
```

FIG. 19C

```
AGGAGGTAAAACATATGCATCACCACCACCATCACGAAAACTTATACTTCCAAGGCAGCGTAAA
TCTGGCATCGCAACTGAGAGAGGGCACCAAAAAGTCGCACAGCATGGCGGAGAATGTGGGTTTT
GTCAAGTGTTTCTTGAAGGGTGTTGTTGAGAAGAACAGCTACCGTAAACTGGTCGGTAATCTGT
ATTTTGTCTACAGCGCGATGGAAGAGGAAATGGCGAAGTTCAAGGATCATCCGATTCTGTCCCA
CATCTACTTCCCGGAACTGAACCGTAAGCAGTCCCTGGAACAGGACCTGCAGTTTTACTACGGT
AGCAACTGGCGTCAGGAAGTGAAAATCAGCGCTGCAGGCCAAGCTTACGTGGACCGCGTGCGCC
AGGTTGCGGCAACCGCACCGGAGCTGCTGGTCGCACACAGCTACACCCGTTATCTGGGTGATCT
GTCTGGCGGCCAAATCCTGAAGAAAATCGCGCAGAACGCGATGAATCTGCACGACGGCGGCACT
GCCTTTTACGAATTTGCAGACATTGACGATGAAAAGGCGTTCAAGAATACTTACCGTCAAGCCA
TGAACGACCTGCCGATTGACCAAGCTACCGCGGAACGTATCGTCGATGAAGCGAATGACGCGTT
TGCGATGAATATGAAAATGTTCAACGAGCTGGAGGGCAATCTGATCAAAGCGATCGGTATTATG
GTATTCAATAGCCTGACGCGCCGTCGCTCTCAGGGCAGCACCGAGGTGGGTCTGGCAACGAGCG
AAGGCTGACTCGAG
```

FIG. 20

```
MSVNLASQLREGTKKSHSMAENVGFVKCFLKGVVEKNSYRKLVGNLYFVYSAMEEEMAKF
KDHPILSHIYFPELNRKQSLEQDLQFYYGSNWRQEVKISAAGQAYVDRVRQVAATAPELL
VAHSYTRYLGDLSGGQILKKIAQNAMNLHDGGTAFYEFADIDDEKAFKNTYRQAMNDLPI
DQATAERIVDEANDAFAMNMKMFNELEGNLIKAIGIMVFNSLTRRRSQGSTEVGLATSEG
```

FIG. 21

```
MDYNLALDTALNRLHTEGRYRTFIDIERRKGAFPKAMWRKPDGSEKEITVWCGNDYLGMG
QHPVVLGAMHEALDSTGAGSGGTRNISGTTLYHKRLEAELADLHGKEAALVFSSAYIAND
ATLSTLPQLIPGLVIVSDKLNHASMIEGIRRSGTEKHIFKHNDLDDLRRILTSIGKDRPI
LVAFESVYSMDGDFGRIEEICDIADEFGALKYIDEVHAVGMYGPRGGVAERDGLMDRID
IINGTLGKAYGVFGGYIAASSKMCDAVRSYAPGFIFSTSLPPVVAAGAAASVRHLKGDVE
LREKHQTQARILKMRLKGLGLPIIDHGSHIVPVHVGDPVHCKMISDMLLEHFGIYVQPIN
FPTVPRGTERLRFTPSPVHDSGMIDHLVKAMDVLWQHCALNRAEVVA
```

FIG. 23

BILIVERDIN FROM A NON-ANIMAL SOURCE

RELATED APPLICATIONS

This application claims the benefit of U.S. Provisional Patent Application No. 61/258,126, filed Nov. 4, 2009, entitled "Enhanced Bioproduction of Biliverdin-IX alpha," which is hereby incorporated herein by reference.

BACKGROUND

Biliverdin IX-alpha (biliverdin IXα) is the most common form of several biliverdin isomers found in nature (FIG. 1). It is produced from heme (also named iron protoporphyrin IX) (FIG. 1) by the enzyme heme oxygenase. In animals, biliverdin IXα is reduced by the enzyme biliverdin reductase to bilirubin IXα which is the major form of several bilirubin isomers (FIG. 1). One known role of biliverdin IXα in nature is in animals as an intermediate in hemoglobin breakdown as red blood cells are degraded in phagocytes (FIG. 2). The hemoglobin prosthetic group, heme, with its bound iron, is released in this degradative process, and heme is converted by HO to biliverdin IXα. Biliverdin IXα is then converted to bilirubin IXα by the enzyme biliverdin reductase (FIG. 2). Bilirubin IXα is consecutively bound to serum albumin and then in the liver to glucoronic acid (conjugated bilirubin) which confers a relatively high degree of water solubility. Conjugated bilirubin is then excreted in the bile. Overall, this process is viewed as a process for animals (e.g. humans) to degrade and eliminate heme—which is toxic when accumulated.

Biliverdin IXα is also made by microbes. For example, biliverdin IXα is a precursor to microbial phycobilins, i.e. phycocyanobilin (pcb) and phycoerythrobilin (peb). Pcb and peb are the pigment molecules for the light-harvesting complexes of photosynthetic cyanobacteria, phycocyanin and phycoerythrin, respectively. These complexes collect light energy (for example solar energy) and funnel it to photosynthetic reaction centers where the energy is converted into chemical energy) (FIG. 3). Pcb is also the pigment for phytochrome—a light sensing receptor that occurs in plants and other cells. An analogous receptor, bacteriophytochrome, is found in certain bacteria. The pigment for bacteriophytochrome is biliverdin IXα rather than pcb, which reveals yet another biological role for biliverdin IXα. These latter bacteria—like all microbes—either do not produce or do not accumulate bilirubin IXα. The lack of bilirubin IXα accumulation by microbes is either a consequence of lacking biliverdin reductase or the conversion of bilirubin IXα to bile pigments such as those involved in photosynthetic light-harvesting.

Bilirubin IXα is known to associate with cell membranes where it quenches the propagation of reactive oxygen species (ROS). It is therefore believed to confer protection to membrane lipid and protein components against oxidative damage. Thus, an additional suggested function of biliverdin IXα is to serve as the immediate source of bilirubin IXα which in turn acts as a cytoprotective antioxidant and anti-inflammatory agent against cell damaging ROS (FIG. 4). Although bilirubin IXα (and not biliverdin IXα) is believed to be the cytoprotective antioxidant, it is observed that biliverdin IXα is more effective than bilirubin IXα when administered at tissue injury/inflammatory sites where ROS are prevalent. One explanation for the higher efficacy of biliverdin IXα is that it is more hydrophilic than bilirubin IXα and therefore has better access to tissue sites where it is then reduced by biliverdin reductase to bilirubin IXα. Another explanation is that when biliverdin IXα binds to biliverdin reductase, this enzyme is activated and initiates a cell signaling cascade that results in the production of the anti-inflammatory cytokine interferon-10.

There is increasing evidence that biliverdin IXα can be used as a cytoprotective therapeutic agent. Examples of clinical applications of biliverdin IXα include treatment of vasoconstriction (U.S. Patent Application Publication No. 20030027124); coronary artery disease (artherosclerosis); ischemia/reperfusion injuries after small intestinal, heart, and kidney transplantation; severe sepsis; injuries from liver grafts; and prevention of intimal hyperplasia induced by vascular injury. Today, biliverdin IXα is predominantly derived by chemical oxidation of bilirubin IXα or by using the enzyme bilirubin oxidase (U.S. Pat. No. 5,624,811). Bilirubin IXα is extracted from the bile of various mammals, especially from swine or other livestock. Commercial animal bilirubin IXα preparations are often contaminated with conjugated bilirubin and isomers (e.g. bilirubin XIIIα) (Reisinger et al. 2001; U.S. Pat. No. 431,166). As a result, biliverdin IXα derived from bilirubin IXα preparations using oxidative processes or enzymes may also contain isomers. The clinical consequences of using biliverdin IXα contaminated with such isomers are not clear. In addition, the use of biliverdin IXα preparations derived from animal bilirubin carries the risk of prion contamination often associated with materials derived from animal sources.

A recent claim (U.S. Pat. No. 7,504,243) for biliverdin IXα production by a yeast depends on addition of hemoglobin (from animal blood) to the growth culture as a source of heme. Another report shows biliverdin IXα synthesis by *Escherichia coli* expressing a heterologous HO gene of animal origin (rat). The biliverdin IXα was produced at low levels and appears to remain cell-bound.

The limited amounts of biliverdin IXα produced by yeast and *E. coli* expressing heterologous HO genes could result from restricted access to heme. In *E. coli*, the biosynthesis of heme is regulated at the initial step of tetrapyrrole biosynthesis—the synthesis of 5-aminolevulinic acid (ALA) by the C5-pathway. The C5 pathway involves conversion of glutamate to glutamyl-tRNA by glutamyl-tRNA synthetase, reduction to glutamate-γ-semialdehyde by an NADPH-dependent glutamyl tRNA reducatase and transamination by glutamate-γ-semialdehyde aminomutase to form ALA. The C5 pathway is feedback-inhibited by heme and, as a consequence, the cellular levels of heme are kept low. In contrast, mammals, plants, and certain bacteria such as *Rhodobacter sphaeroides* produce ALA from glycine and succinyl-CoA via the enzyme ALA synthetase. This latter mechanism for ALA biosynthesis is termed the "C4 pathway." The C4 pathway ALA synthetase is not subject to feedback inhibition by heme. It therefore allows the accumulation of heme and higher cellular concentrations. When combined with the C4 pathway for ALA synthesis, HO will have greater access to its substrate, heme, resulting in increased potential for producing biliverdin IXα.

SUMMARY

Methods for producing biliverdin in a microorganism, methods for producing biliverdin from a non-animal source, cells for producing biliverdin and methods for producing cells for producing biliverdin are disclosed. These methods and cells conform to a general strategy for enhanced production of biliverdin for a non animal source. This general strategy is depicted in FIG. 14.

In one aspect, a method of producing biliverdin in a microorganism is disclosed, comprising: culturing a cell comprising a recombinant heme oxygenase and a recombinant heme biosynthetic enzyme.

In certain embodiments, the cell comprises a vector comprising a polynucleotide which codes for a recombinant heme oxygenase. In certain other embodiments, the cell comprises a vector comprising a polynucleotide which codes for a recombinant heme biosynthetic enzyme. The cell may also comprise a regulatable promoter operably linked to a polynucleotide which codes for the heme oxygenase. In a related embodiment, the cell comprises a regulatable promoter operably linked to a polynucleotide which codes for the heme biosynthetic enzyme. The regulatable promoter may comprise the T7 promoter.

In certain embodiments, the heme biosynthetic enzyme is an ALA synthase. In a related embodiment, the heme biosynthetic enzyme is hemA. In another related embodiment, the heme biosynthetic enzyme is an ALA synthase analog.

In certain other embodiments, the heme oxygenase is a HO family enzyme. In a related embodiment, the heme oxygenase enzyme is HO1. In another related embodiment, the heme oxygenase enzyme is an HO family analog.

In certain other embodiments, lactose is provided to the cell. Lactose may be provided in an initial concentration of from about 2% (w/v) to about 10% (w/v). Furthermore, the methods may further comprise the step of providing a trace metal to the cell. Trace metals may be added as part of a trace metal solution. Some or all of NaCl, $ZnSO_4$, $MnCl_2$, $FeCl_3$, $CuSO_4$, $H_3BO_3$, $NaMoO_4$, $H_2SO_4$, $MgSO_4$, thiamine or $CaCl_2$ may be provided to the cell.

In certain other embodiments, a plurality of measurements of the dissolved oxygen concentration in the growth medium of the cell may be taken. In a related set of embodiments, at least an initial measurement, a first intermediate measurement, a second intermediate measurement, and a third intermediate measurement of dissolved oxygen concentration in the growth medium of the cell may be taken. In related embodiments, the initial measurement yields an initial value, the first intermediate measurement yields a first intermediate value less than the initial value, the second intermediate measurement yields a second intermediate value greater than the first intermediate value, and the third intermediate measurement yields a third intermediate value less than the first intermediate value. In further related embodiments, dissolved oxygen in the growth medium in concentrations at the initial value, the first intermediate value, the second intermediate value and the third intermediate value indicates that biliverdin will be produced.

In certain other embodiments, the biliverdin is excreted into the growth medium of the cell. In one such embodiment, foam accumulates in the growth medium of the cell and a portion of the biliverdin excreted in to the growth medium of the cell is located with the foam. In related embodiments, the foam is collected. In any embodiment, the biliverdin may be collected.

In another aspect, a method of producing biliverdin from a non-animal source is disclosed, comprising: culturing a cell comprising a recombinant heme oxygenase and a recombinant heme biosynthetic enzyme.

In certain embodiments, the cell comprises a vector comprising a polynucleotide which codes for a recombinant heme oxygenase. In certain other embodiments, the cell comprises a vector comprising a polynucleotide which codes for a recombinant heme biosynthetic enzyme. The cell may also comprise a regulatable promoter operably linked to a polynucleotide which codes for the heme oxygenase. In a related embodiment, the cell comprises a regulatable promoter operably linked to a polynucleotide which codes for the heme biosynthetic enzyme. The regulatable promoter may comprise the T7 promoter.

In certain embodiments, the heme biosynthetic enzyme is an ALA synthase. In a related embodiment, the heme biosynthetic enzyme is hemA. In another related embodiment, the heme biosynthetic enzyme is an ALA synthase analog.

In certain other embodiments, the heme oxygenase is a HO family enzyme. In a related embodiment, the heme oxygenase enzyme is HO1. In another related embodiment, the heme oxygenase enzyme is an HO family analog.

In certain other embodiments, lactose is provided to the cell. Lactose may be provided in an initial concentration of from about 2% (w/v) to about 10% (w/v). Furthermore, the methods may further comprise the step of providing a trace metal to the cell. Trace metals may be added as part of a trace metal solution. Some or all of NaCl, $ZnSO_4$, $MnCl_2$, $FeCl_3$, $CuSO_4$, $H_3BO_3$, $NaMoO_4$, $H_2SO_4$, $MgSO_4$, thiamine or CaCl2 amy be provided to the cell.

In certain other embodiments, a plurality of measurements of the dissolved oxygen concentration in the growth medium of the cell may be taken. In a related set of embodiments, at least an initial measurement, a first intermediate measurement, a second intermediate measurement, and a third intermediate measurement of dissolved oxygen concentration in the growth medium of the cell may be taken. In related embodiments, the initial measurement yields an initial value, the first intermediate measurement yields a first intermediate value less than the initial value, the second intermediate measurement yields a second intermediate value greater than the first intermediate value, and the third intermediate measurement yields a third intermediate value less than the first intermediate value. In further related embodiments, dissolved oxygen in the growth medium in concentrations at the initial value, the first intermediate value, the second intermediate value and the third intermediate value indicates that biliverdin will be produced.

In certain other embodiments, the biliverdin is excreted into the growth medium of the cell. In one such embodiment, foam accumulates in the growth medium of the cell and a portion of the biliverdin excreted in to the growth medium of the cell is located with the foam. In related embodiments, the foam is collected. In any embodiment, the biliverdin may be collected.

In another aspect, a cell comprising a recombinant heme oxygenase and a recombinant heme biosynthetic enzyme is disclosed.

In certain embodiments, the cell comprises a vector comprising a polynucleotide which codes for a recombinant heme oxygenase. In certain other embodiments, the cell comprises a vector comprising a polynucleotide which codes for a recombinant heme biosynthetic enzyme. The cell may also comprise a regulatable promoter operably linked to a polynucleotide which codes for the heme oxygenase. In a related embodiment, the cell comprises a regulatable promoter operably linked to a polynucleotide which codes for the heme biosynthetic enzyme. The regulatable promoter may comprise the T7 promoter.

In certain embodiments, the heme biosynthetic enzyme is an ALA synthase. In a related embodiment, the heme biosynthetic enzyme is hemA. In another related embodiment, the heme biosynthetic enzyme is an ALA synthase analog.

In certain other embodiments, the heme oxygenase is a HO family enzyme. In a related embodiment, the heme oxygenase enzyme is HO1. In another related embodiment, the heme oxygenase enzyme is an HO family analog.

In another aspect, methods of producing a cell for producing biliverdin are disclosed. In certain embodiments, a polynucleotide comprising a sequence which codes for a recombinant heme oxygenase is introduced into a parent cell comprising a recombinant heme biosynthetic enzyme. In certain other embodiments, a polynucleotide comprising a sequence which codes for a recombinant heme biosynthetic enzyme is introduced into a parent cell comprising a recombinant heme oxygenase. In certain other embodiments, the method comprises introducing into a parent cell a first polynucleotide comprising a first sequence which codes for a recombinant heme oxygenase; and a second polynucleotide comprising a second sequence which codes for a recombinant heme biosynthetic enzyme.

In other embodiments, a polynucleotide comprising a first sequence which codes for a recombinant heme oxygenase and a second sequence which codes for a recombinant heme biosynthetic enzyme is introduced into a parent cell.

In certain other embodiments, a first polynucleotide comprising a promoter sequence is introduced into a parent cell, and the first polynucleotide recombines with a second polynucleotide comprising a sequence which codes for a heme oxygenase, such that the first polynucleotide and a portion of the second polynucleotide form a linked polynucleotide which codes for a recombinant heme oxygenase.

In another set of embodiments, a first polynucleotide comprising a promoter sequence is introduced into a parent cell, and the first polynucleotide recombines with a second polynucleotide comprising a sequence which codes for a heme biosynthetic enzyme, such that the first polynucleotide and a portion of the second polynucleotide form a linked polynucleotide which codes for a recombinant heme biosynthetic enzyme.

For any method of producing a cell for producing biliverdin, introducing a polynulcoetide into a cell may be performed by transformation. The cell used may be a microorganism, bacterial cell, or an *Escherichia coli* cell. Furthermore, the methods of producing biliverdin may comprise culturing cells comprising a polynucleotide which has been optimized for expression in a cell. The cells for producing biliverdin may comprise culturing cells comprising a polynucleotide which has been optimized for expression in a cell. Furthermore, the methods of producing cells for producing biliverdin may comprise introducing a polynucleotide into the parent cell, the polynucleotide having been optimized for expression in a cell.

Additional aspects and advantages will be apparent from the following detailed description of preferred embodiments, which proceeds with reference to the accompanying drawings.

BRIEF DESCRIPTION OF THE DRAWINGS

FIG. 6 shows the DNA base sequence of cyanobacterium *Synechocystis* PCC6803 HO1 (SEQ ID NO: 48) (726 base pairs).

FIG. 7 shows the DNA base sequence of HemA of *R. sphaeroides* ALA synthetase (SEQ ID NO: 49) (1224 base pairs).

(FIG. 13B).

FIG. 16A through FIG. 16B shows an alignment of several HO family heme oxygenases.

FIG. 17 shows an alignment of several subfamily members for several HO subfamilies. FIG. 17A shows an alignment of the HO-1 subfamily of heme oxygenases. FIG. 17B through FIG. 17C shows an alignment of the HMOX1 subfamily of heme oxygenases. FIG. 17D shows an alignment of the ho subfamily of heme oxygenases.

FIG. 18A through FIG. 18C shows an alignment of diverse ALA synthases.

FIG. 19A through FIG. 19C shows an alignment of ALA synthases that are homologs of SEQ ID NO: 2.

FIG. 20 shows the optimized HO-1 gene DNA sequence provided by DNA 2.0 Inc. (SEQ ID NO: 50).

FIG. 21 shows the polypeptide sequence of HO-1 (SEQ ID NO: 1)

FIG. 23 shows the polypeptide sequence of HemA (SEQ ID NO: 2).

DETAILED DESCRIPTION OF PREFERRED EMBODIMENTS

Definitions

Figure 1:
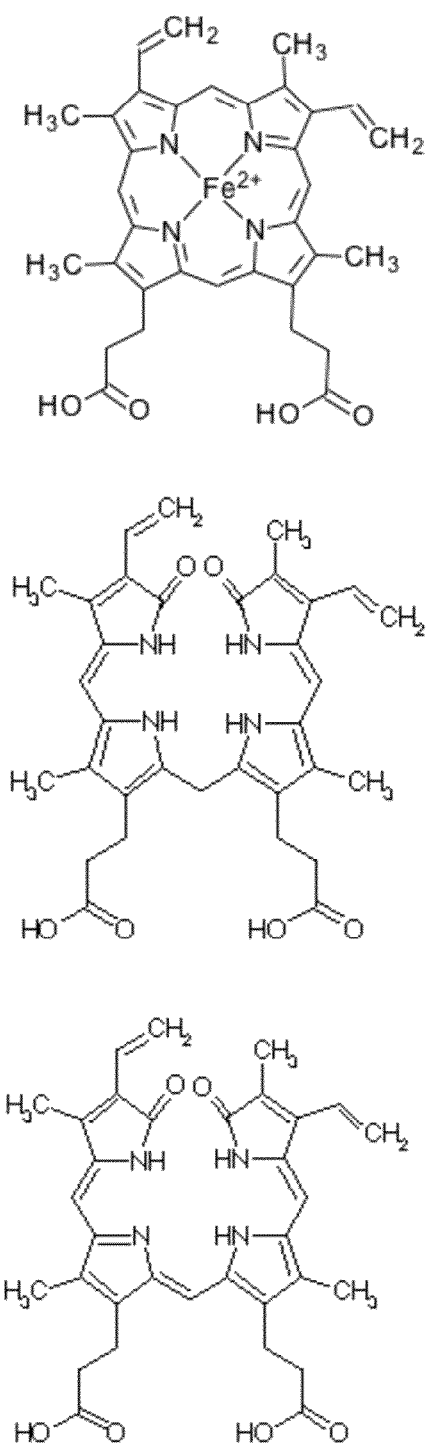
FIG. 1 shows the chemical structures of heme (top), bilirubin IXα (center), and biliverdin IXα (bottom).
Figure 2:
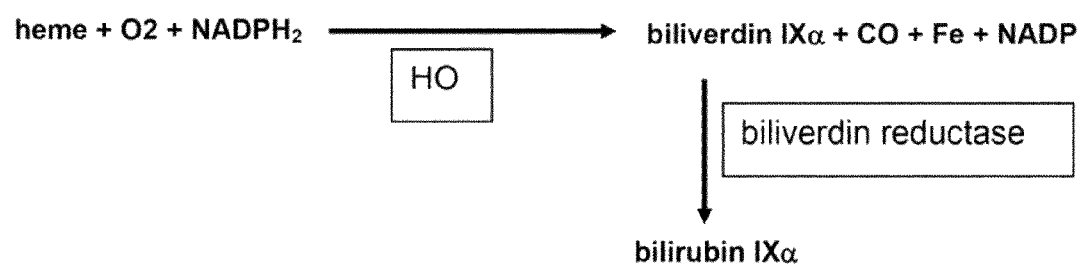
FIG. 2 shows the metabolic transformations of heme, biliverdin IXα and bilirubin IXα in animals.
Figure 3:
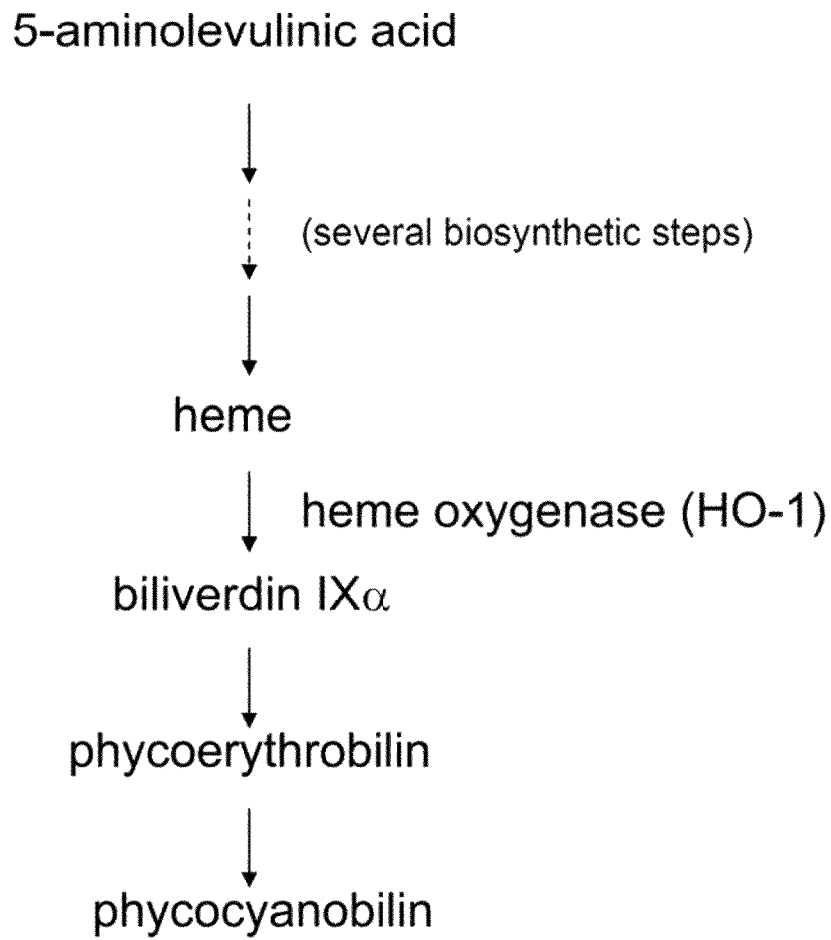
FIG. 3 shows the roles of biliverdin IXα and HO-1 in the biosynthesis of cyanobacterial phycocyanobilins.
Figure 4:
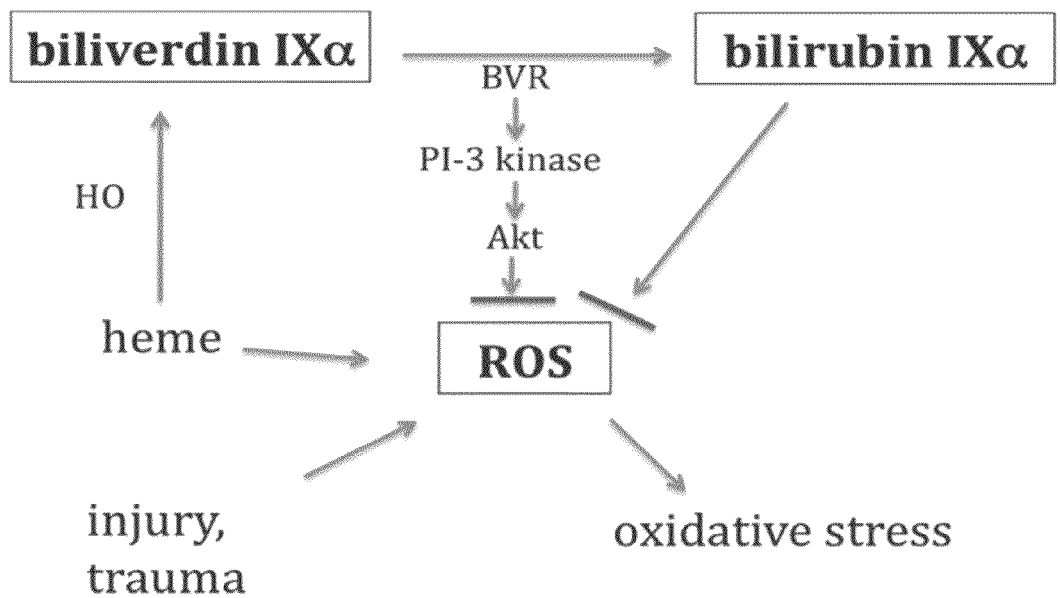
FIG. 4 shows the cytoprotective role of biliverdin IXα and bilirubin IXα against ROS. Acronym definitions are: HO (heme oxygenase), BVR (biliverdin reductase) and ROS (reactive oxygen species). The bars indicate suppression of ROS.
Figure 5:
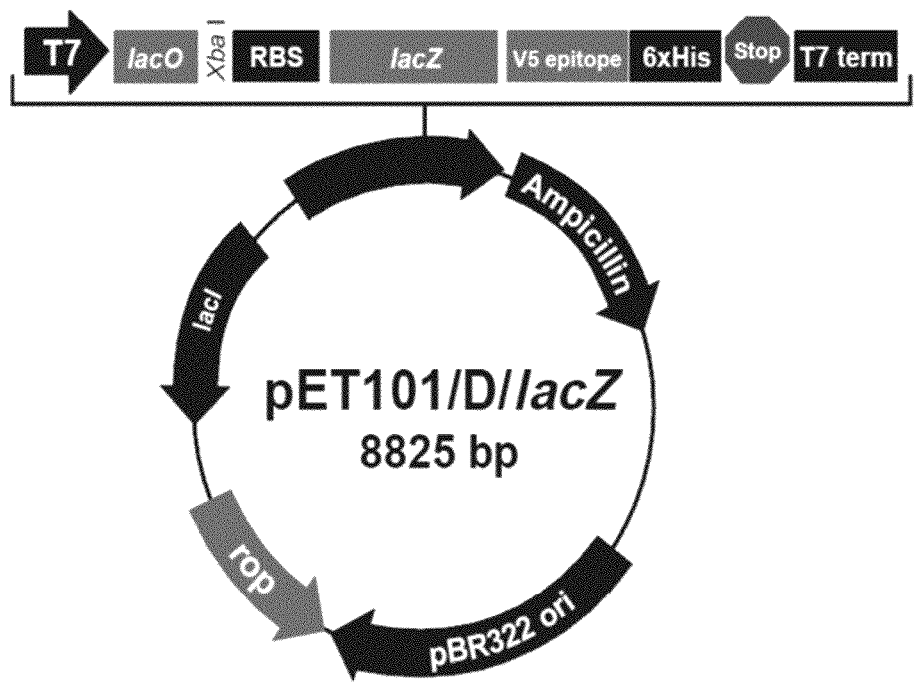
FIG. 5 shows a gene map for pET101 plasmid expression vector with T7 promoter used to express HemA and HO1 in *E. coli*.

"Biliverdin" means biliverdin IXα (CAS Registry Number: 114-25-0).

To "culture" or "culturing" means to provide nutrients to a cell sufficient to allow the cell to grow and reproduce. Methods of culturing cells are known in the art. In particular, method of culturing cells, including bacteria, are described in (Joe Sambrook, *Molecular Cloning: A Laboratory Manual, Third Edition*, Cold Spring Harbor Laboratory Press, 2001 (ISBN: 0879695773); or in Frederick M. Ausubel, et al., eds., *Current Protocols in Molecular Biology*, Wiley (ISSN: 1934-3639, last updated Jun. 28, 2010)), which are incorporated by reference.

"Recombinant" may be used to describe a polynucleotide or a polypeptide. A "recombinant polynucleotide" is a polynucleotide within a cell that comprises a sequence not naturally found inside that cell. For example, a recombinant polynucleotide could comprise a coding sequence (CDS) that is not naturally found in the cell. Alternatively a recombinant polynucleotide could comprise two sequences joined together, where one sequence is naturally found in the cell, and the other is not. For example a CDS naturally found in the cell could be operably linked to a promoter that is not naturally found in the cell. A "recombinant polypeptide" is the polypeptide product of a recombinant polynucleotide that comprises a CDS. For example, a recombinant heme oxygenase is the polypeptide product of a recombinant polynucleotide which codes for the heme oxygenase.

A polynucleotide "codes for" a polypeptide when the polynucleotide comprises a set of codons which, when transcribed and translated by cellular machinery, will produce a polypeptide whose amino acid sequence corresponds to the codons of the polynucleotide according to a genetic code.

"CDS" means coding sequence. A coding sequence is a polynucleotide sequence that codes for a polypeptide product.

A polynucleotide or polypeptide is "naturally found" in a cell when that polynucleotide or polypeptide is present in a healthy, uninfected, wild-type cell under one or more culture conditions. All other polynucleotides and polypeptides are not naturally found in a cell.

A "heme oxygenase" is an enzyme with the activity defined by Enzyme Commission ("E.C.") number 1.14.99.3. Heme oxygenases include two families of enzymes, the HO family, and the HemS family. The HO family is a defined enzyme family comprising, for example, polypeptides (SEQ ID NOs: 1 and 7-28). The identity of these SEQ IDs is shown in Table 1. The HO family may be defined, for example, by shared sequence motifs as described in the Hidden Markov Model Pf01126. An alignment of several HO family heme oxygenases is provided in FIG. 16. The HO family may also be subdivided into subfamilies, including the HMOX1 subfamily found in some animals, the HO-1 subfamily found in some cyanobacteria and the ho subfamily found in some plants. An alignment of several subfamily members for several HO subfamilies is found in FIG. 17. The HemS family of enzymes is also a defined enzyme family comprising *Escherichia coli* O157:H7 gene product ChuS and other proteins. The HemS family may be defined, for example, by shared sequence motifs as described in the Hidden Markov Model PF05171.

TABLE 1

Representative sample of HO family heme oxygenases

| SEQ ID | Species | Gene product |
|---|---|---|
| 1 | Synechocyctis PCC 6803 | HO-1 |
| 7 | Cyanotheca sp. | cce2573 |
| 8 | Synechococcus sp. | A2508 |
| 9 | Anabaena sp. | all1897 |
| 10 | Corynebacterium Diphtheriae | Hmuo |
| 11 | Synechocystis sp. | 1WOW_A |
| 12 | Oryctolagus cuniculus | heme oxygenase 2 |
| 13 | Pseudomonas aeruginosa | gi 50513550 |
| 14 | Takifugu rubripes | HMOX |
| 15 | Drosophila melanogaster | Q9VGJ9 |
| 16 | Bradyrhizobium sp | gi 75412672 |
| 17 | Pseudomonas aeruginosa | gi 81540044 |
| 18 | Streptomyces coelicolor | gi 81550417 |
| 19 | Bos taurus | HMOX1 |
| 20 | Homo sapiens | HMOX1 |
| 21 | Mus musculus | Hmox1 |
| 22 | Rattus norvegicus | Hmox1 |
| 23 | Arabidopsis thaliana | ho4 |
| 24 | Arabidopsis thaliana | ho3 |
| 25 | Gallus gallus | HMOX1 |
| 26 | Danio rerio | hmox1 |
| 27 | Pan troglodytes | HMOX1 |
| 28 | Canis lupus familiaris | HMOX1 |

A "heme oxygenase analog" means a heme oxygenase enzyme bearing one or more additions deletions or substitutions of residues compared to the original heme oxygenase. Useful heme oxygenase analogs include analogs which retain the heme oxygenase activity defined by E.C. 1.14.99.3. By examining and aligning known heme oxygenase sequences from a given heme oxygenase family, a skilled person can determine which heme oxygenase residues are conserved across species. Using this alignment, the skilled person could generate a consensus sequence, using, for example, the Clustal algorithm. Since conserved residues are generally those which are required for function (Boffelli D, Nobrega M A, Rubin E M. *Comparative genomics at the vertebrate extremes*. Nat Rev Genet. 2004; 5:456-465), non-naturally occurring proteins that conform to this consensus sequence would define heme oxygenase analogs that likely retain the heme oxygenase activity defined by E.C. 1.14.99.3. For example, from the alignments in FIG. 16 or 17, a consensus sequence for the HO family could be constructed. Further, additional alignments may be generated using, for example, the HomoloGene and Conserved Domain (CDD) algorithms of the National Center for Biotechnology Information (NCBI), U.S. National Library of Medicine, Bethesda Md. USA.

Alternatively, generating heme oxygenase analogs which retain heme oxygenase activity could also be accomplished by using existing bioinformatic resources. Proteins and protein domains are often described by a Hidden Markov Model (HMM). An HMM of a polypeptide is not a sequence alignment, but it does convey actual structural information about the protein. Most HMMs are based on the probability of any particular residue occurring next to a second residue in the linear sequence of the polypeptide. Using HMMs to describe proteins is discussed in Krogh A, Brown M, Mian I S, Sjölander K, Haussler D, *Hidden Markov models in computational biology. Applications to protein modeling*. J Mol. Biol. 1994; 235; 1501-31, which is hereby incorporated by reference.

The European Bioinformatics Institute maintains the Interpro database, which compiles HMM information from various databases, including some described below. Interpro has two different entries which describe heme oxygenases. The first is IPR002051 Haem oxygenase (defining the HO family) and IPR007845 Haemin-degrading HemS (defining the HemS family).

The Wellcome Trust Sanger Institute also maintains the Pfam database, which describes the heme oxygenase proteins in terms of HMMs. The Pfam HMMs that define the heme oxygenase proteins are PF01126 (HO family) and PF05171 (HemS family). Included in the database for each HMM entry is a feature which allows the user to visualize the structural information in the HMM.

Although the HMMs do not provide typical sequence information regarding heme oxygenase proteins, they do provide a description of the probable structure of a heme oxygenase. Thus, analogs of heme oxygenase that conform to the HMM would be more likely to retain heme oxygenase activity. To easily generate sequences of heme oxygenase analogs more likely to have heme oxygenase activity, a skilled person could generate heme oxygenase analog sequences using a computer to introduce substitutions, deletions or additions to a heme oxygenase sequence. The relative probabilities embodied in the heme oxygenase HMMs could guide a skilled person regarding which residues, when mutated, are more likely to lead to a loss of function. The skilled person could then compare the analog sequences to the HMMs in the databases listed above. Those analogs which met the threshold of being tagged as bearing a heme oxygenase domain would likely have the property of heme oxygenase activity. The HMMs discussed above which describe heme oxygenases and heme oxygenase analogs are hereby incorporated by reference.

"HO1" or "HO-1" is the polypeptide represented by SEQ ID NO: 1.

A "heme biosynthetic enzyme" is an enzyme involved in the anabolic metabolism of heme. Heme biosynthetic enzymes include Amino levulinic acid dehydratase, Porphobilinogen deaminase, Uroporphyrinogen III synthase, Uroporphyrinogen III decarboxylase, Coprophorinogen III oxidase, Protopophyrinogen IX oxidase, and Ferrochetalase. These enzymes are well characterized and their role in heme biosynthesis is understood. A very important step in the production of Heme is the production of amino levulinic acid (ALA). Two anabolic pathways exist for the production of ALA, the C-4 and C-5 pathways. The enzymes of the C-4 and C-5 pathway are heme biosynthetic enzymes. An example of a C-5 pathway enzyme is glutamyl-tRNA reductase. An example of a C-4 pathway enzyme is ALA synthase.

An "ALA synthase" or "ALA sythetase" is an enzyme with the activity defined by E.C. 2.3.1.37. ALA synthase enzymes are not subject to feedback inhibition from heme. ALA synthases are a defined class of enzymes including, for example, polypeptides (SEQ ID NOs: 2 and 29-47). The identity of these SEQ IDs is shown in Table 2. The ALA synthases may be defined, for example, by shared sequence motifs as described in the Hidden Markov Model TIGR01821. An alignment of diverse ALA synthases is provided in FIG. 18. An alignment of conserved homologs of SEQ ID NO: 2 is provided in FIG. 19.

TABLE 2

Representative sample of ALA synthetases

| SEQ ID | Species | Gene product |
| --- | --- | --- |
| 2 | Rhodobacter sphaeroides 2.4.1 | HemA |
| 29 | Hyphomonas neptunium ATCC 15444 | gi 114797766 |
| 30 | Orientia tsutsugamushi str. Boryong | gi 148284187 |

TABLE 2-continued

Representative sample of ALA synthetases

| SEQ ID | Species | Gene product |
| --- | --- | --- |
| 31 | Azorhizobium caulinodans ORS 571 | gi 158421958 |
| 32 | Caulobacter crescentus CB15GI: 16125604 | gi 16125604 |
| 33 | Brucella canis ATCC 23365 | gi 161618302 |
| 34 | Bordetella petrii DSM 12804 | gi 163855632 |
| 35 | Caulobacter sp. K31 | gi 167647011 |
| 36 | Streptomyces griseus subsp. griseus | gi 182439088 |
| 37 | Orientia tsutsugamushi str. Ikeda | gi 189183979 |
| 38 | Phenylobacterium zucineum HLK1 | gi 197105140 |
| 39 | Phenylobacterium zucineum HLK1 | gi 197106256 |
| 40 | Caulobacter crescentus NA1000 | gi 221234354 |
| 41 | Candidatus Liberibacter asiaticus str. | gi 254780604 |
| 42 | Neorickettsia risticii str. | gi 254797163 |
| 43 | Brucella microti CCM 4915 | gi 256368778 |
| 44 | Chromobacterium violaceum ATCC 12472 | gi 34496258 |
| 45 | Brucella abortus bv. 1 str. | gi 62289313 |
| 46 | Staphylococcus aureus RF122 | gi 82751601 |
| 47 | Neorickettsia sennetsu str. Miyayama | gi 88608338 |

An "ALA synthase analog" means an ALA synthase enzyme bearing one or more additions deletions or substitutions of residues compared to the original ALA synthase. Useful ALA synthase analogs include analogs which retain the activity defined by E.C. 2.3.1.37. By examining and aligning known ALA synthase sequences, a skilled person can determine which ALA synthase residues are conserved across species. Using this alignment, the skilled person could generate a consensus sequence, using, for example, the Clustal algorithm. Since conserved residues are generally those which are required for function (Boffelli D, Nobrega. M A, Rubin E M. *Comparative genomics at the vertebrate extremes*. Nat Rev Genet. 2004; 5:456-465), non-naturally occurring proteins that conform to this consensus sequence would define ALA synthase analogs that likely retain the ALA synthase activity defined by E.C. 2.3.1.37. For example, from the alignment in FIG. 18 or 19, a consensus sequence for several ALA synthases may be constructed. Further, additional alignments may be generated using, for example, the HomoloGene and Conserved Domain (CDD) algorithms of the National Center for Biotechnology Information (NCBI), U.S. National Library of Medicine, Bethesda Md. USA.

Alternatively, generating ALA synthase analogs which retain ALA synthase activity could also be accomplished by using HMM as described above.

Interpro has one entry which describe ALA synthases: IPR010961 Tetrapyrrole biosynthesis, 5-aminolevulinic acid synthase. The J. Craig Venter Institute maintains the TIGR database. The TIGR HMM profile that describes the probable structure of ALA synthases is TIGR01821.

Although these HMMs do not provide typical sequence information regarding ALA synthase proteins, they do provide a description of the probable structure of a ALA synthase. Thus, analogs of ALA synthase that conform to the HMM would be more likely to retain ALA synthase activity. To easily generate sequences of ALA synthase analogs more likely to have ALA synthase activity, a skilled person could generate ALA synthase analog sequences using a computer to introduce substitutions, deletions or additions to a ALA synthase sequence. The relative probabilities embodied in the ALA synthase HMMs could guide a skilled person regarding which residues, when mutated, are more likely to lead to a loss of function. The skilled person could then compare the analog sequences to the HMMs in the databases listed above. Those analogs which met the threshold of being tagged as bearing a ALA synthase domain would likely have the property of ALA synthase activity. The HMMs discussed above which describe ALA synthases and ALA synthase analogs are hereby incorporated by reference.

"HemA" is the polypeptide represented by SEQ ID NO: 2.

"Growth media" or "growth medium" is a composition comprising one or more nutrients used to culture a cell. Growth medium includes any foam which accumulates in the medium.

A "vector" is a polynucleotide which can be used to introduce a desired sequence into a cell. The vector polynucleotide typically includes additional sequences, including sequences that direct propagation of the vector in the cell or insertion of part of the vector into the cell's genome, and a gene which allows an individual to screen for the presence of the vector. Common examples of vectors include plasmids, artificial chromosomes, viruses, and linear polynucleotide fragments which are designed to insert into a cell's genome. Vectors are well known tools to the skilled artisan, and an artisan can easily find appropriate vectors for a particular organism in the literature or in biobanks such as ATCC.

A "promoter" is a polynucleotide sequence that, when operably linked to a CDS, is sufficient, under one or more conditions, to cause an RNA polymerase to begin transcribing an mRNA from a polynucleotide.

A promoter is "operably linked" to a polynucleotide sequence when the promoter is linked to the polynucleotide sequence in such a way that a RNA polymerase will transcribe at least a portion of the polynucleotide sequence. Typically, linking a promoter to the 5' end of a polynucleotide will result in the promoter being operably linked to the polynucleotide.

In the context of a first polynucleotide and a second polynucleotide, the first and second polynucleotides are "linked" when they are joined by a linker or a phosphodiester bond.

A "linker" is a polynucleotide of one of more bases which is used to link two or more polynucleotides.

"Foam" is a suspension of a gas in another substance. When foam accumulates in growth media, a gas which is in contact with the growth media become suspended in the media. For example foam often forms in vessels containing growth media when they are agitated.

Biliverdin is from a "non-animal source" when the heme oxidase catalyzed step of biliverdin production is not performed in a cell from an organism in the Eukaryotic kingdom *animalia*, and where the heme substrate of the heme oxidase was not produced in a cell from an organism in the Eukaryotic kingdom *animalia*.

"Collecting" a substance means removing a measurable quantity of the substance from the vessel in which it was produced. For example, if foam was produced in a vessel while a cell was cultured, removing the foam from the vessel is collecting the foam. Likewise, in the context of producing biliverdin, removing biliverdin from the vessel in which it was produced is collecting the biliverdin. "Collecting" does not necessitate purification of the biliverdin from the organism in which the biliverdin was synthesized.

In the context of generating a cell for producing biliverdin, "a parent cell" is a cell into which a recombinant heme oxygenase and/or a recombinant heme biosynthetic enzyme is introduced.

To "introduce" or "introducing" a polynucleotide into a cell means using physical or genetic techniques to cause the polynucleotide to enter within a membrane which surrounds the cell. These include transformation, conjugation between bacterial cells, and recombination during sexual reproduction.

To "transform" or "transforming" means to introduce a polynucleotide into a cell by chemical, electrical or other physical means. Methods of transforming cells include chemical destabilization of the cell membrane to allow the polynucleotide to enter, electroporation, microinjection, or firing particles coated with the polynucleotide into the cell.

A composition found inside a cell is "excreted" when the composition moves outside of the membrane surrounding the cell. A composition may be excreted passively, meaning that the composition diffuses across the membrane, or a compound may be excreted actively, meaning that cellular factors aid the composition in moving outside the membrane surrounding the cell.

A first composition is "located with" a second composition when a measurable quantity of the second composition is associated with the first composition such that collecting the first composition will also collect some of the associated second composition.

A polynucleotide that contains a CDS is "optimized for expression in a cell" where one or more nucleotide bases of the polynucleotide are modified according to an algorithm such that when the polynucleotide is linked to a promoter and introduced into a cell, more of the protein product of the CDS is produced than would be produced by the unmodified polynucleotide linked to the same promoter.

Various methods of modifying a polynucleotide so that it is optimized for expression in a cell are known. For example, the polynucleotide sequence may be modified according to the Codon Adaptation Index method (Sharp, P. M., and W. H. Li, (1987). *The codon adaptation index a measure of directional synonymous codon usage bias, and its potential applications*. Nucleic Acids Research 15: 1281-1295, which is hereby incorporated by reference). Also, the polynucleotide sequence may be modified according to the Frequency of Optimal Codons method (Ikemura, T., (1981). *Correlation between the abundance of Escherichia coli transfer RNAs and the occurrence of the respective codons in its protein genes: a proposal for a synonymous codon choice that is optimal for the E. coli system*. Journal of Molecular Biology 151: 389-409, which is incorporated by reference).

Alternatively, a polynucleotide may be optimized for expression in a cell where the nucleotide bases are modified according to the proprietary methods of DNA 2.0 Inc., Menlo Park, Calif.

Many of the embodiments described below incorporate methods for culturing cells, transforming cells, or performing other genetic manipulations on cells. Many methods for performing these steps are known in the art. In particular, many laboratory methods are described in Joe Sambrook, *Molecular Cloning: A Laboratory Manual, Third Edition*, Cold Spring Harbor Laboratory Press, 2001 (ISBN: 0879695773); or in Frederick M. Ausubel, et al., eds., *Current Protocols in Molecular Biology*, Wiley (ISSN: 1934-3639, last updated Jun. 28, 2010, which are incorporated by reference.

Methods of Producing Biliverdin

One aspect of the invention includes methods of producing biliverdin in a microorganism. Another aspect of the invention includes methods for producing biliverdin from a non-animal source. In general, both methods of producing biliverdin in a microorganism and methods of producing biliverdin from a non-animal source include culturing a cell comprising a recombinant heme oxygenase and a recombinant heme biosynthetic enzyme. The embodiments described below represent embodiments of both methods of producing biliverdin in a microorganism and methods for producing biliverdin from a non-animal source.

In one embodiment, the cultured cell comprises a vector comprising a polynucleotide which codes for a recombinant heme oxygenase. In another embodiment, the cell comprises a vector comprising a polynucleotide which codes for a recombinant heme biosynthetic enzyme. The vector may be a plasmid, a construct designed to integrate into the genome of the cell, an artificial chromosome, or any other vector known in the art which is appropriate for use in the cell. For example, ATCC maintains a collection of vectors for use in a variety of organisms.

In another embodiment, a promoter may drive expression of a polynucleotide which codes for a recombinant heme oxygenase. In another embodiment, a promoter may drive expression of a polynucleotide which codes for a recombinant heme oxygenase. In any embodiment where a promoter is used, the promoter may be a regulatable promoter. Furthermore, regulatable promoters may be used to control the expression of recombinant polypeptides in a temporal or other fashion. Some regulatable promoters are inducible promoters. For example, the T7 promoter drives very low basal levels of expression when cells are grown in the absence of IPTG. However, when IPTG is added to the culture media, the promoter is activated and higher expression is induced. Other regulatable promoters may be repressible promoters. For example, the tetR promoter has very low expression when cells are grown in the presence of tetracycline, but expression increases when tetracycline is removed from the growth medium. Many promoters which are appropriate for use in a variety of cells are known in the art. The Registry of Standard Biological Parts, maintained by Massachusetts Institute of Technology discloses many promoters which will be appropriate for use in different types of cells to achieve a desired pattern of expression. The Registry of Standard Biological Parts is hereby incorporated by reference.

In another embodiment, the heme oxygenase enzyme is a HO family heme oxygenase. In another embodiment, the heme oxygenase is a HemS family heme oxygenase. In a particular embodiment, HO1 (SEQ ID NO: 1) is used as the heme oxygenase. In another embodiment, the heme oxygenase enzyme may be an HO family analog.

In another emdodiment, the heme bisynthetic enzyme used is ALA dehydratase. In another emdodiment, the heme bisynthetic enzyme used is Porphobilinogen deaminase. In another emdodiment, the heme bisynthetic enzyme used is Uroporphyrinogen III synthase. In another emdodiment, the heme bisynthetic enzyme used is Uroporphyrinogen III decarboxylase. In another emdodiment, the heme bisynthetic enzyme used is Coprophorinogen III oxidase. In another emdodiment, the heme bisynthetic enzyme used is Protopophyrinogen IX oxidase. In another emdodiment, the heme bisynthetic enzyme used is Ferrochetalase.

In certain embodiments, the heme biosynthetic enzyme used is an ALA synthase. In a particular embodiment, the heme biosynthetic enzyme is hemA (SEQ ID NO: 2). In certain other embodiments, the heme biosynthetic enzyme is an ALA synthase analog.

Figure 9:
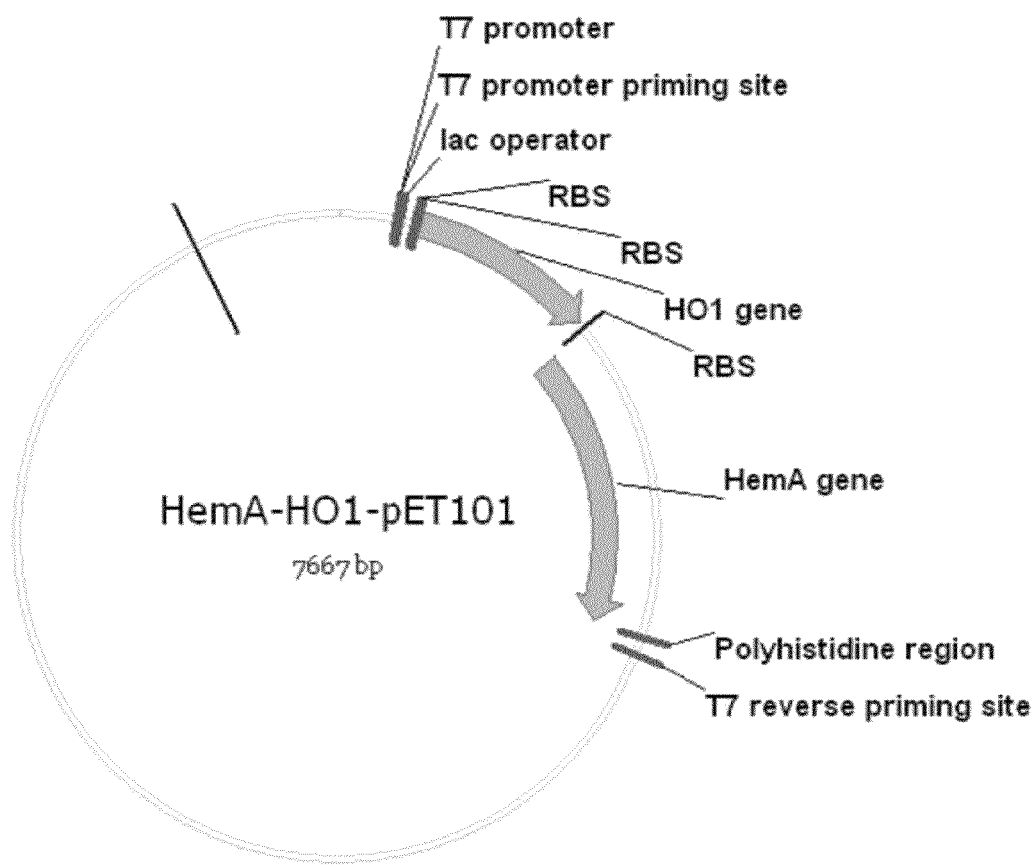
FIG. 9 shows a gene map of the plasmid expression vector HemA-HO1-pET101 with HO1 and HemA genes inserted downstream of DNA sequences that permit transcriptional regulation via T7 lac operon dependent mechanisms and ribosome binding sites (RBSs) for each gene to provide efficient initiation of protein translation.

In a particular embodiment, the cell comprises HemA-HO1-pET101 (FIG. 9).

In another embodiment, lactose is provided to the cell which is being cultured. Generally, lactose may be provided to the cell as a component of the growth medium. Lactose may be provided in a initial concentration, and the actual concentration of lactose in the media will decrease as the cells consume it. In one embodiment, the initial concentration of lactose is from about 2% (w/v) to about 10% (w/v). In another embodiment, the lactose may be provided in an initial concentration of about 2, 2.5, 3, 4, 5, 6, 7, 8, 9, 10 or about 10%. In a particular embodiment the initial concentration of lactose is 2.5%.

In another embodiment, one or more trace metals is provided to the cell. The trace metal(s) may be provided in the form of a trace metal solution. In one embodiment, one or more of NaCl, $ZnSO_4$, $MnCl_2$, $FeCl_3$, $CuSO_4$, $H_3BO_3$, $NaMoO_4$, $H_2SO_4$, $MgSO_4$, thiamine or $CaCl_2$ are added to the culture. In another embodiment, NaCl, $ZnSO_4$, $MnCl_2$, $FeCl_3$, $CuSO_4$, $H_3BO_3$, $NaMoO_4$, $H_2SO_4$, $MgSO_4$, thiamine and $CaCl_2$ are added to the culture.

In another embodiment, the concentration of dissolved oxygen in the growth medium of the cell is measured. Any oxygen measuring device known in the art can be used. For example an oxygen measuring probe may be used. In one embodiment, InPro® 6800 Series $O_2$Sensors (METTLER TOLEDO) may be used in monitoring the concentration of dissolved oxygen In one embodiment, a plurality of measurements of the dissolved oxygen concentration are made. In another embodiment, the concentration of dissolved oxygen has an initial value, then the dissolved oxygen concentration decreases to a first intermediate value, then the dissolved oxygen concentration increases to a second intermediate value greater than the first intermediate value, then the dissolved oxygen concentration decreases to a third intermediate value less than the first intermediate value.

In another embodiment, the biliverdin is excreted from the cell into the growth medium. In another embodiment, foam accumulates in the growth medium, and a portion of the biliverdin is located with the foam. In a related embodiment, the foam is collected. In another embodiment, the biliverdin is collected.

For any embodiment of a method of producing biliverdin discussed above, the cell may comprise a polynucleotide that is optimized for expression in a cell In certain embodiments, the cell comprises a sequence that codes for a heme oxygenase that is optimized for expression in a cell. In certain embodiments, the cell comprises a sequence that codes for an HO family heme oxygenase that is optimized for expression in a cell. In one embodiment, the cell comprises a sequence that codes for HO-1 that is optimized for expression in a cell. In one embodiment, the cell comprises a sequence that codes for HO-1 that is optimized for expression in a bacterial cell. In one embodiment, the cell comprises a sequence that codes for HO-1 that is optimized for expression in an *Escherichia coli* cell. In another embodiment, the cell comprises a polynucleotide comprising SEQ ID NO: 50, wherein the cell is a bacterial cell. In another embodiment, the cell comprises a polynucleotide comprising bases 15 to 776 of SEQ ID NO: 50, wherein the cell is a bacterial cell. In another embodiment, the cell comprises a polynucleotide comprising SEQ ID NO: 50, wherein the cell is an *Escherichia coli* cell. In another embodiment, the cell comprises a polynucleotide comprising bases 15 to 776 of SEQ ID NO: 50, wherein the cell is an *Escherichia coli* cell.

In certain embodiments, the cell comprises a sequence that codes for a heme biosynthetic enzyme that is optimized for expression in a cell. In certain embodiments the cell comprises a sequence that codes for an ALA synthase that is optimized for expression in a cell. In one embodiment, the cell comprises a sequence that codes for HemA that is optimized for expression in a cell. In a related embodiment, the cell comprises a sequence that codes for HemA that is optimized for expression in a bacterial cell. In a related embodiment, the cell comprises a sequence that codes for HemA that is optimized for expression in an *Escherichia coli* cell.

Cells for Producing Biliverdin

Another aspect of the invention includes cells for producing biliverdin. In general, cells for producing biliverdin comprise a recombinant heme oxygenase and a recombinant heme biosynthetic enzyme.

In one embodiment, the cell comprises a vector comprising a polynucleotide which codes for a recombinant heme oxygenase. In another embodiment, the cell comprises a vector comprising a polynucleotide which codes for a recombinant heme biosynthetic enzyme. The vector may be a plasmid, a construct designed to integrate into the genome of the cell, an artificial chromosome, or any other vector known in the art which is appropriate for use in the cell. For example, ATCC maintains a collection of vectors for use in a variety of organisms.

Figure 8:
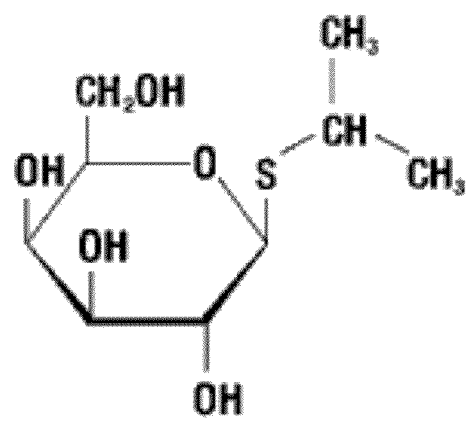
FIG. 8 shows the chemical structure of isopropyl-beta-D-thiogalactopyranoside (IPTG).

In another embodiment, the cell comprises a promoter that may drive expression of a polynucleotide which codes for a recombinant heme oxygenase. In another embodiment, the cell comprises a promoter that may drive expression of a polynucleotide which codes for a recombinant heme oxygenase. In any embodiment where a promoter is used, the promoter may be a regulatable promoter. Furthermore, regulatable promoters may be used to control the expression of recombinant polypeptides in a temporal or other fashion. Some regulatable promoters are inducible promoters. For example, the T7 promoter drives very low basal levels of expression when cells are grown in the absence of IPTG (FIG. 8). However, when IPTG is added to the culture media, the promoter is activated and higher expression is induced. Other regulatable promoters may be repressible promoters. For example, the tetR promoter has very low expression when cells are grown in the presence of tetracycline, but expression increases when tetracycline is removed from the growth medium. Many promoters which are appropriate for use in a variety of cells are known in the art. The Registry of Standard Biological Parts, maintained by Massachusetts Institute of Technology discloses many promoters which will be appropriate for use in different types of cells to achieve a desired pattern of expression. The Registry of Standard Biological Parts is hereby incorporated by reference.

In another embodiment, the heme oxygenase enzyme is a HO family heme oxygenase. In another embodiment, the heme oxygenase is a HemS family heme oxygenase. In a particular embodiment, HO1 (SEQ ID NO: 1) is used as the heme oxygenase. In another embodiment, the heme oxygenase enzyme may be an HO family analog.

In another emdodiment, the heme bisynthetic enzyme used is ALA dehydratase. In another embodiment, the heme bisynthetic enzyme used is Porphobilinogen deaminase. In another emdodiment, the heme bisynthetic enzyme used is Uroporphyrinogen III synthase. In another emdodiment, the heme bisynthetic enzyme used is Uroporphyrinogen III decarboxylase. In another emdodiment, the heme bisynthetic enzyme used is Coprophorinogen III oxidase. In another emdodiment, the heme bisynthetic enzyme used is Protopophyrinogen IX oxidase. In another emdodiment, the heme bisynthetic enzyme used is Ferrochetalase.

In certain embodiments, the heme biosynthetic enzyme used is an ALA synthase. In a particular embodiment, the heme biosynthetic enzyme is hemA (SEQ ID NO: 2). In certain other embodiments, the heme biosynthetic enzyme is an ALA synthase analog.

In a particular embodiment, the cell comprises HemA-HO1-pET101 (FIG. 9).

For any embodiment that provides a cell for producing biliverdin discussed above, the cell may comprise a polynucleotide that is optimized for expression in a cell.

In certain embodiments, the cell comprises a sequence that codes for a heme oxygenase that is optimized for expression in a cell. In certain embodiments, the cell comprises a sequence that codes for an HO family heme oxygenase that is optimized for expression in a cell. In one embodiment, the cell comprises a sequence that codes for HO-1 that is optimized for expression in a cell. In one embodiment, the cell comprises a sequence that codes for HO-1 that is optimized for expression in a bacterial cell. In one embodiment, the cell comprises a sequence that codes for HO-1 that is optimized for expression in an *Escherichia coli* cell. In another embodiment, the cell comprises a polynucleotide comprising SEQ ID NO: 50, wherein the cell is a bacterial cell. In another embodiment, the cell comprises a polynucleotide comprising bases 15 to 776 of SEQ ID NO: 50, wherein the cell is a bacterial cell. In another embodiment, the cell comprises a polynucleotide comprising SEQ ID NO: 50, wherein the cell is an *Escherichia coli* cell. In another embodiment, the cell comprises a polynucleotide comprising bases 15 to 776 of SEQ ID NO: 50, wherein the cell is an *Escherichia coli* cell.

In certain embodiments, the cell comprises a sequence that codes for a heme biosynthetic enzyme that is optimized for expression in a cell. In certain embodiments the cell comprises a sequence that codes for an ALA synthase that is optimized for expression in a cell. In one embodiment, the cell comprises a sequence that codes for HemA that is optimized for expression in a cell. In a related embodiment, the cell comprises a sequence that codes for HemA that is optimized for expression in a bacterial cell. In a related embodiment, the cell comprises a sequence that codes for HemA that is optimized for expression in an *Escherichia coli* cell.

Methods of Producing Cells

Another aspect of the invention includes methods of producing cells for producing biliverdin. In general, these methods comprise introducing into a cell a recombinant polypeptide. In one embodiment, a recombinant heme oxygenase is introduced into the cell. In another embodiment, a recombinant heme biosynthetic enzyme is introduced into the cell.

In one embodiment, the method comprises introducing into the cell a polynucleotide comprising a sequence which codes for a recombinant heme oxygenase. In another embodiment, the method comprises introducing into the cell a polynucleotide comprising a sequence which codes for a recombinant heme biosynthetic enzyme. In another embodiment, a polynucleotide is introduced into the cell, the polynucleotide comprising a first sequence which codes for a recombinant heme oxygenase and a second sequence which codes for a recombinant heme biosynthetic enzyme. In a particular embodiment, the HemA-HO1-pET101 (FIG. 9) is introduced into the cell.

In another embodiment, a promoter is introduced into the cell in such a way that it recombines with a sequence which codes for a heme oxygenase to produce a linked polynucleotide which codes for a recombinant heme oxygenase, where the parent cell comprises a recombinant heme biosynthetic enzyme. In another embodiment, a promoter is introduced into the cell in such a way that it recombines with a sequence which codes for a heme biosynthetic enzyme to produce a linked polynucleotide which codes for a recombinant heme biosynthetic enzyme, where the parent cell comprises a recombinant heme oxygenase. Methods of introducing polynucleotides for directed recombination with polynucleotides in a cell are known in the art. For example, methods for directed recombination are discussed in AJ Link et al., Methods for generating precise deletions and insertions in the genome of wild-type *Escherichia coli*: application to open reading frame characterization, J. Bacteriol, (179) 6228-6237 (1997), which is incorporated by reference.

In another embodiment, any step comprising introducing a polynucleotide into a cell comprises transforming the cell.

In another embodiment, the cell is a microorganism. In another embodiment, the cell is a prokaryotic cell. In another embodiment, the cell is a bacterial cell. In another embodiment, the cell is an *Escherichia coli* cell.

For any embodiment that provides a method of producing a cell for producing biliverdin discussed above, the polynucleotides may be optimized for expression in a cell.

In certain embodiments, a sequence that codes for a heme oxygenase that is optimized for expression in a cell is introduced into a cell. In certain embodiments, a sequence that codes for an HO family heme oxygenase that is optimized for expression in a cell is introduced into a cell. In one embodiment, a sequence that codes for HO-1 that is optimized for expression in a cell is introduced into a cell. In another embodiment, a polynucleotide comprising SEQ ID NO: 50 is introduced into a bacterial cell. In another embodiment, a polynucleotide comprising bases 15 to 776 of SEQ ID NO: 50 is introduced into a bacterial cell. In another embodiment, a polynucleotide comprising SEQ ID NO: 50 is introduced into an *Escherichia coli* cell. In another embodiment, a polynucleotide comprising bases 15 to 776 of SEQ ID NO: 50 is introduced into an *Escherichia coli* cell.

In certain embodiments, a sequence that codes for a heme biosynthetic enzyme that is optimized for expression in a cell is introduced into a cell. In certain embodiments a sequence that codes for an ALA synthase that is optimized for expression in a cell is introduced into a cell. In one embodiment, a sequence that codes for HemA that is optimized for expression in a cell is introduced into a cell. In a related embodiment, a sequence that codes for HemA that is optimized for expression in a cell is introduced into a bacterial cell. In a related embodiment, a sequence that codes for HemA that is optimized for expression in a cell is introduced into an *Escherichia coli* cell.

The following examples are intended to further illustrate exemplary embodiments and are not intended to limit the scope of the disclosure.

EXAMPLES

Example 1

Construction of Plasmid Expression Vectors and Gene Expression

HO-1 pET101: HO(HO-1) gene of *Synechocystis* PCC6803 was amplified by the polymerase chain reaction (PCR) using the following primers:

```
(HO1 forward primer)
CACCATGAGTGTCAACTTAGCTTC        (SEQ ID NO: 3)

(HO1 reverse primer)
CTAGCCTTCGGAGGTGGCGA            (SEQ ID NO: 4)
```

The PCR product was blunt ended using thermostable proofreading polymerase, gel purified, ligated into pET101 vector by directional TOPO® Cloning Reaction and transformed into chemically competent *E. coli* TOP10 (Invitrogen) cells according to the manufacturer's instructions. Five white colonies were selected on Xgal agar plates, plasmids isolated and subjected to gel electrophoresis to confirm cloning of HO-1 into the vector. DNA sequencing showed that the cloned DNA had an identical sequence to Synechococcus PCC6803 HO-1 (SEQ ID NO: 48) (FIG. 6). The vector with the HO-1 gene was transformed into *E. coli* BL21 (Invitrogen) and cells from a single white colony were propagated in Luria-Bertani (LB) broth medium (25 g per L, Fisher Scientific) plus 100 μg per mL ampicillin. Its DNA plasmids were isolated and the HO-1 gene sequence in the plasmid was confirmed by DNA sequencing again. The plasmid was used as the clone that harbored expression vector HO-1 pET101.

HemA-HO-1 pET101: HemA which encodes ALA synthase from *R. sphaeroides* was amplified by the polymerase chain reaction (PCR) using the following primers:

```
(Hem A forward primer)
                                 (SEQ ID NO: 5)
ACAACGTTGAAGGAGCCCTTCTCCATGGACTACAATCTGGCACT (Hem A reverse primer)
                                 (SEQ ID NO: 6)
ATGACCGGTACGTCAGGCAACGACCTCGGCGC
```

The HemA gene was cut by restriction enzymes (AclI and AgeI) and ligated to HO1-pET101 vector which was digested by restriction enzymes (BstBI and AgeI). The construct was transformed into competent *E. coli* BL21 (DE3) (Invitrogen) cells according to the manufacturer's instructions. Five white colony isolates were selected and were propagated in Luria-Bertani (LB) broth medium (25 g per L, Fisher Scientific) plus 100 μg per mL ampicillin. Their plasmid DNAs were extracted and the occurrence of HemA was confirmed by DNA sequencing (FIG. 7—SEQ ID NO: 49). After DNA sequencing analysis of the plasmid DNAs, an isolate yielding plasmid DNA with the expected size was selected, designated *E. coli* strain HemA-HO-1 and was used as the clone that harbors expression vector HemA-HO-1 pET101.

Example 2

Bacterial Growth, Protein Expression, and Production of Biliverdin

*E. coli* strains HO-1 and HemA-HO-1 were maintained on LB agar medium with 100 μg per mL ampicillin. For analysis of protein expression, cells were grown in LB broth medium supplemented with 1% glucose and 100 μg per mL ampicillin with rotary shaking 225 rpm at 37° C. overnight. IPTG was added (1 mM final concentration) when the culture achieved an absorbance between 0.3 and 0.5 at 600 nm. Exponentially grown cells were harvested and lysed and cell extracts were recovered as supernatant fractions after centrifugation at 8,000×g for a minimum of 5 min. The cell extracts were subjected to sodium dodecylsulfate polyacrylamide gel electrophoresis and the gel was stained with Coomasie Brilliant Blue. The stained gel showed the induction of the HO-1 protein (23 kdaltons) by IPTG in both *E. coli* strains which confirmed the expression of HO-1 gene.

For biliverdin production, the HemA and HO-1 containing *E. coli* strains are grown in 100 to 200-ml of LB broth medium plus 100 μg per mL ampicillin in 500-mL capacity Erlenmeyer flasks in a rotary water bath shaker (200 rpm) at 37° C. to a cell density showing an absorbance of 4 to 5 measured at 600 nm using a 1 cm path length cuvette and LB broth medium as blank. The culture is then added to 1 or 1.5 L of LB broth medium or biliverdin—Minimal Medium (biliverdin 2) (per L, $KH_2PO_4$, 3.5 g; $K_2HPO_4$, 5.0 g; $(NH_4)_2SO_4$, 5.0 g; yeast extract, 5.0 g; trace metals solution (per L, NaCl, 5 g; $ZnSO_4\text{-}7H_2O$, 1 g; $MnCl_2\text{-}4H_2O$, 4 g; $FeCl_3\text{-}6H_2O$, 4.75 g;

$CuSO_4$-$5H_2O$, 0.4 g; $H_3BO_3$, 0.575 g; $NaMoO_4$-$2H_2O$, 0.5 g; and 6N $H_2SO_4$, ~12.5 ml), 1 mL; $MgSO_4$-$7H_2O$ (25%), 4 mL; thiamine (220 mg per mL), 10 mL, $CaCl_2$-$H_2O$ (15 g per L), 10 mL with trace metals solution, $MgSO_4$-$7H_2O$, thiamine, and $CaCl_2$-$H_2O$ filter sterilized separately and added to the other ingredients after autoclaving) containing 100 mg per L ampicillin and 2.5% α-lactose both filtered sterilized and added separately after autoclaving. The final pH for both growth media is 7.0. The E. coli inocula cultures are added to give an initial absorbance of ~0.03 measured at 600 nm using a 1 cm path length cuvette. The cultures are grown in a VirTis Omniculture bioreactor system with 2.0 L vessel (VirTis, Gardner, N.Y.). Airflow is at 3.5 liters per min at 30° C. Agitation is set at 250 rpm until an absorbance of 0.4 to 0.5 measured at 600 nm (1 cm path length) is attained, and then agitation is increased to 450 rpm. Under these conditions, blue-green pigmented material becomes visible 6 to 10 hours at or near the top of foam formed above the surface of the culture. At this point, dissolved oxygen levels are less than 5% saturation. The material accumulates as a blue-green film and as blue-green aggregates that adhere to the glass walls of the vessel and the stainless steel head plate. In addition, polyethylene tubing (Tygon, ¼ inch I.D., 0.5 to 1 m length) connected to an outlet port of the vessel head plate and with the other end opened into a receiving flask is used to collect foam-trapped blue-green material during culture growth. Growth is terminated after approximately 20 hours or when production of blue-green material ceases.

Example 3

Collecting the Biliverdin

Figure 10:
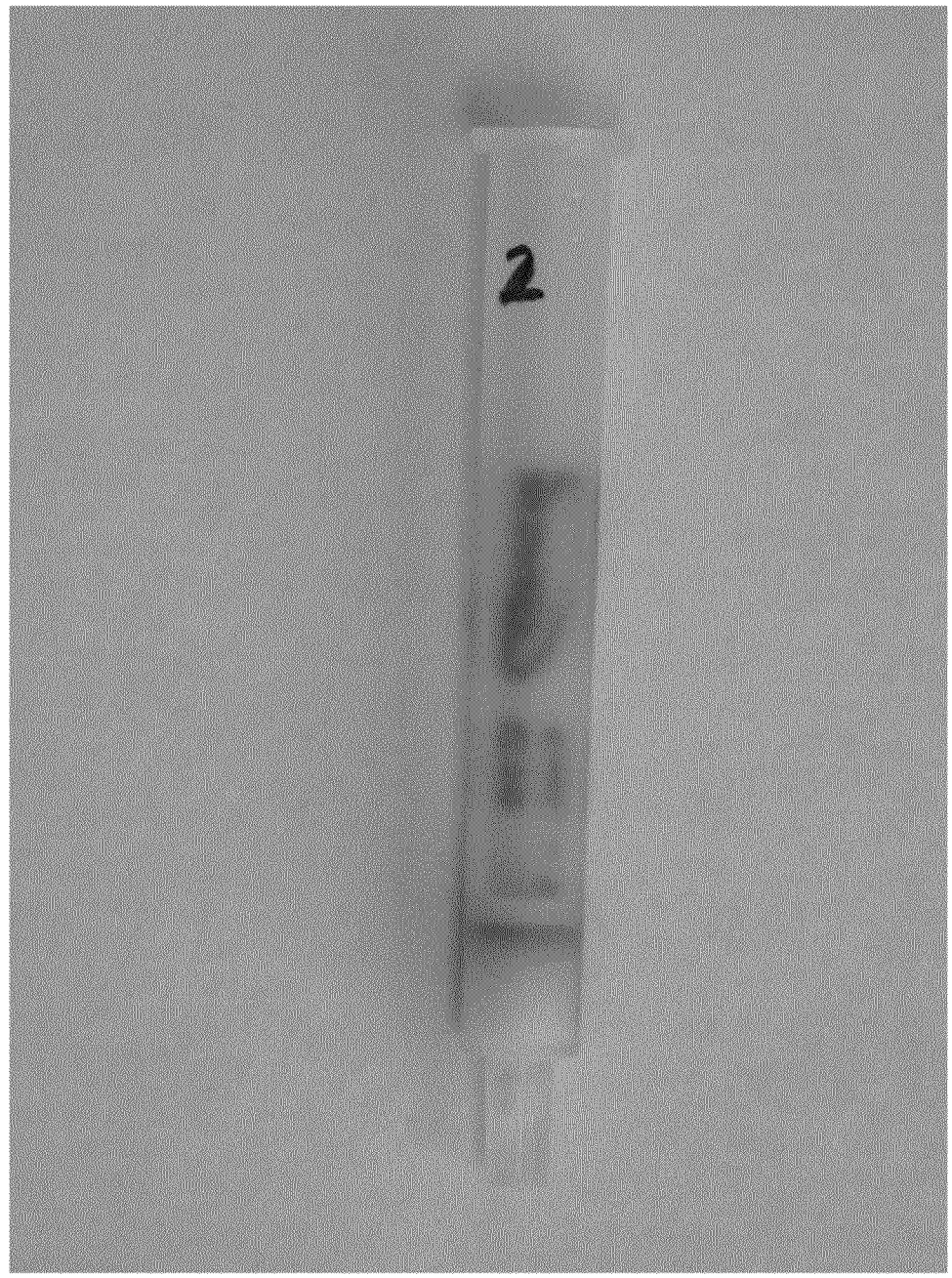
FIG. 10 shows a photograph of solid phase extraction Sepak C18 column (3 ml) with green material produced by *E. coli* (HO-1). A methanol extract of green aggregated material from growing cultures was loaded in 40% methanol, 0.2M Na acetate, pH 5.2. The green material was then eluted off the column with 100% methanol and recovered.

After the growth of a batch culture is completed, the blue-green film and aggregated materials are physically removed from the vessel surfaces using a spatula and suspended in methanol. The methanol suspension is combined with the blue green material collected in the receiving flask and an equivalent volume of methanol is added. A volume of 1N HCl equal to the total volume of the methanol suspension is added dropwise to the suspension with stirring. A ¹⁄₁₀ volume of water is added, and the mixture is vortexed and extracted into chloroform. The green chloroform layer is recovered, dried, and the resulting blue-green material is stored in the dark at −20° C. Absorbance spectra of this material resemble the spectrum obtained for authentic biliverdin (Frontier Scientific, Inc.) suggesting that the blue-green material contains biliverdin IXα. For purification, the dried material is dissolved in 40% methanol, 0.2 M Na acetate, pH 5.2 and loaded onto a Sepak C18 column. The column is eluted successively with 40% methanol, 0.2 M Na acetate, pH 5.2, water, and 100% methanol. The blue-green material elutes with 100% methanol (FIG. 10) and is collected. It is acidified with HCl (0.25 N final concentration), extracted into chloroform and stored in the dark at −20° C.

Example 4

Analytical Determination of Biliverdin

Figure 11:
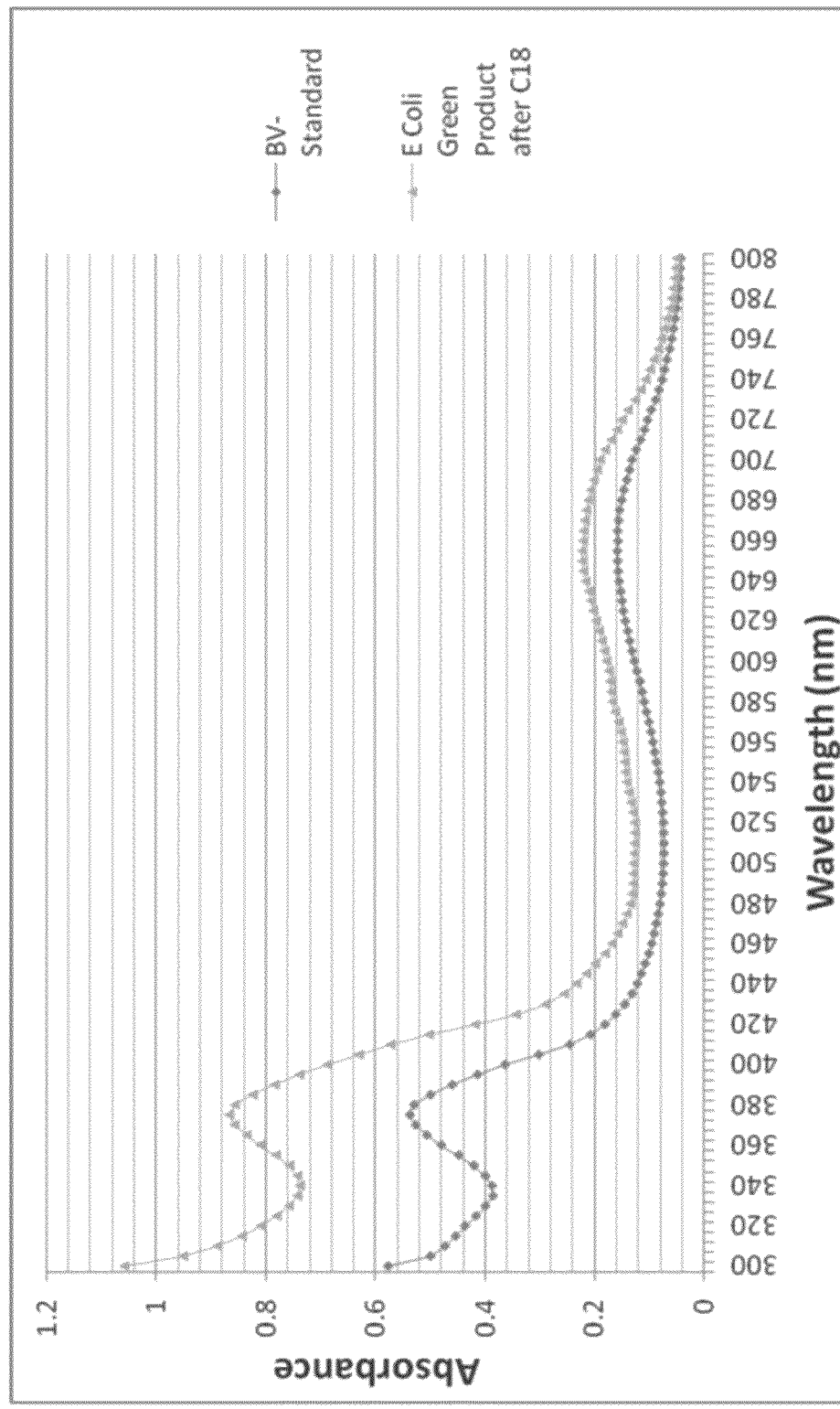
FIG. 11 shows absorbance spectra of a) methanol-extracted green material produced by *E. coli* (HO1), loaded onto a C18 solid phase extraction Sepak C-18 column (3 ml) in 40% methanol, 0.2 M Na acetate, pH 5.2, and recovered by elution with 100% methanol, and b) biliverdin IXα standard, commercially available from Frontier Scientific, Inc.
Figure 12A:
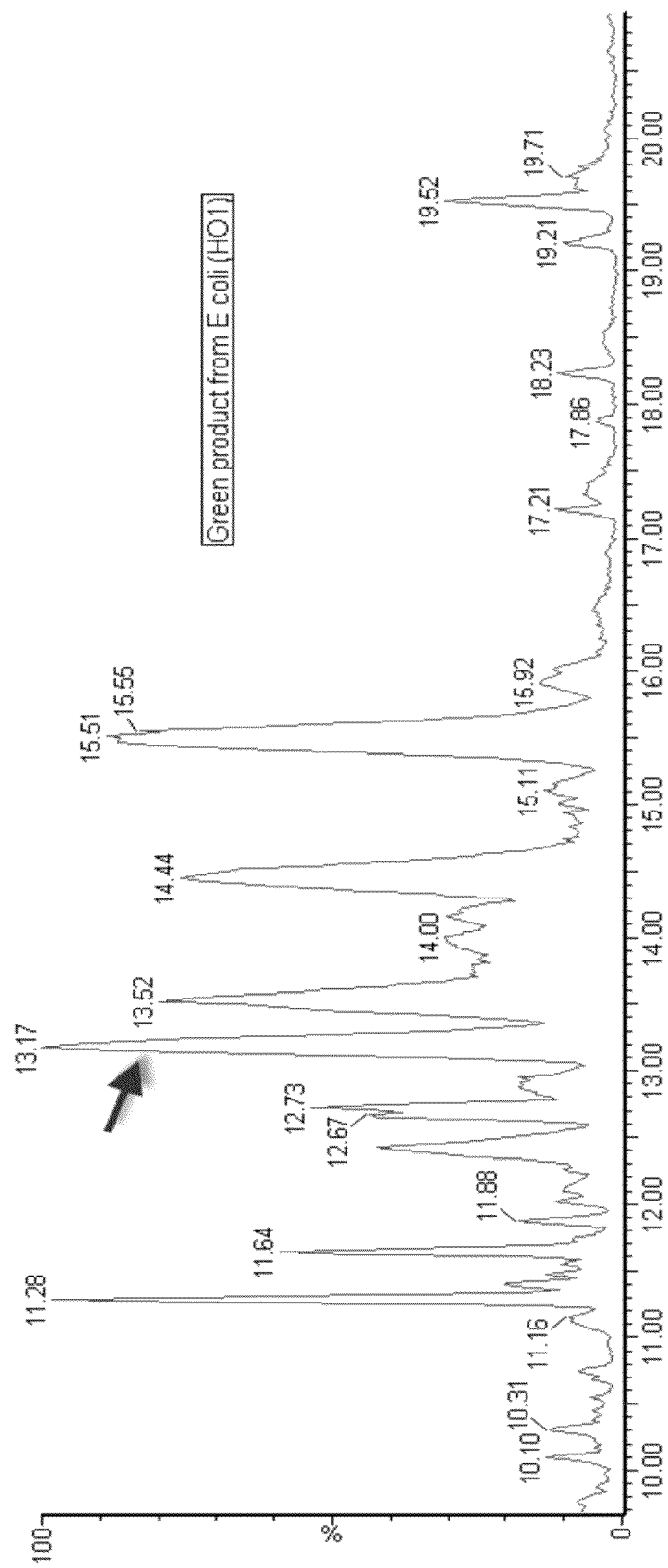
FIG. 12A shows a high-performance liquid chromatograms of methanol-extracted green material from cultures of *E. coli* (HO1)
Figure 12B:
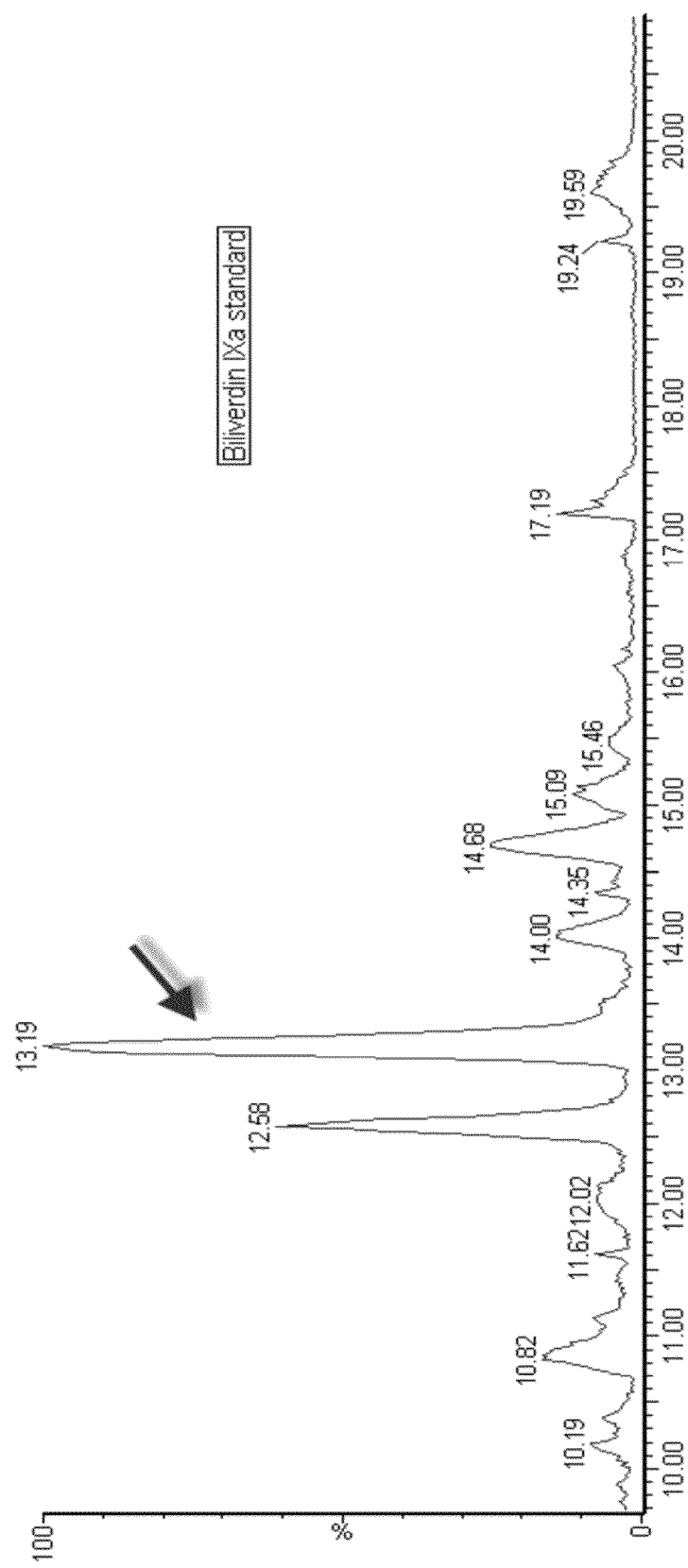
FIG. 12B shows a high-performance liquid chromatograms of a biliverdin IXα standard, commercially available from Frontier Scientific, Inc. The bacterially-derived green material (FIG. 12A) contains components with retention times that are identical to commercially available biliverdin IXα.
Figure 13A:
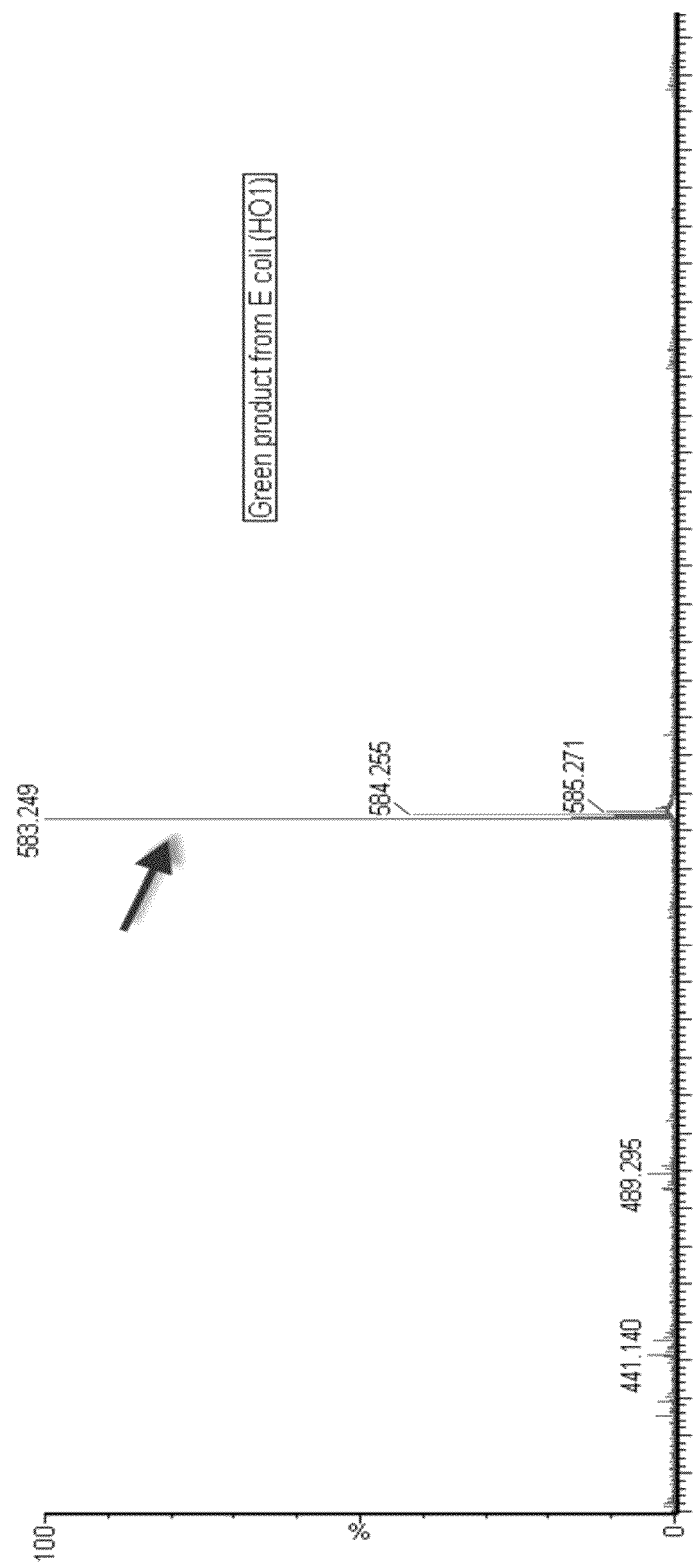
FIG. 13A shows a mass spectrum showing the mass of the methanol, extracted and solid phase extraction recovered "green material" from *E. coli* (HO1).
Figure 13B:
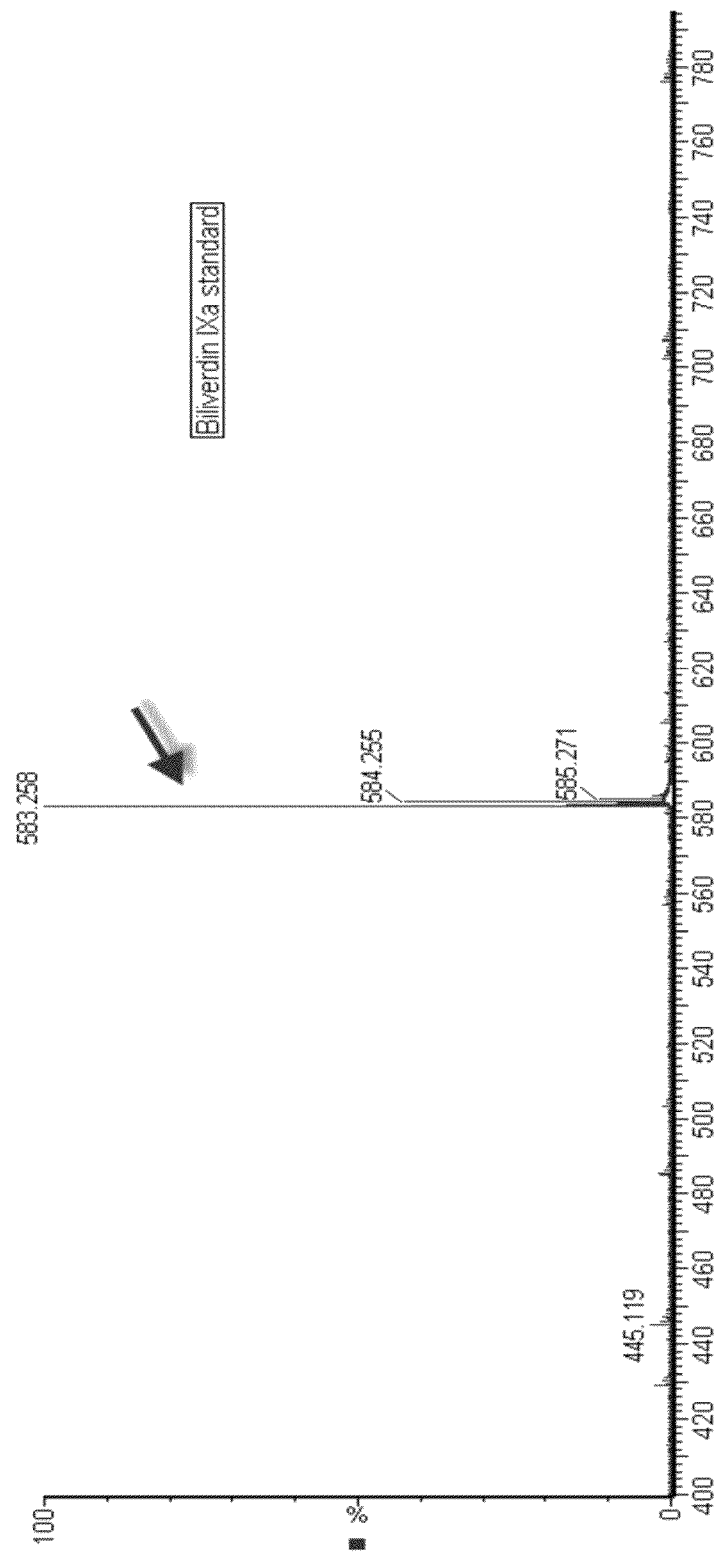
FIG. 13B shows a mass spectrum showing the mass of a commercial biliverdin IXα standard obtained from Frontier Scientific, Inc. The methanol extracted and solid phase extraction recovered "green material" from *E. coli* (HO1) (FIG. 13A) has the same mass (m/e 583.68) as a commercial biliverdin IXα standard obtained from Frontier Scientific, Inc.
Figure 14:
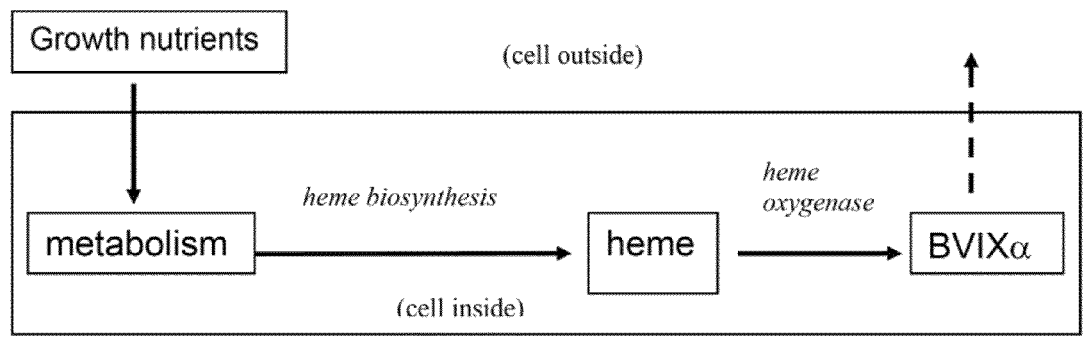
FIG. 14 shows an overall strategy of increasing heme oxygenase activity and the biosynthesis of heme in a host cell to enhance Biliverdin IX alpha accumulation.

Absorbance spectra between wavelengths 300 and 800 nm were obtained using an Applied Biosystem spectrophotometer. The presence of biliverdin in the blue-green material is evident by comparison to the absorbance spectrum of a known standard of biliverdin (from Frontier Scientific, Inc.) derived from bilirubin IXα (FIG. 11) with characteristic spectral peaks at 385 nm and 650 nm-660 nm. The same absorbance spectrum was obtained with blue-green material produced by E. coli strains TOP10 or BL21 transformed with and expressing HO1-pET101 or HemA-HO-1 pET101, respectively. Also, the same absorbance spectrum was obtained with blue-green material from cultures of E. coli strains grown in either LB broth medium or biliverdin 2 broth medium. High performance liquid chromatography (HPLC) is also an analytical tool to help determine the chemical identity of the purified blue-green material as biliverdin. Identical or very similar HPLC peaks (major peaks with Rf values of 13.19 and 13.17 in FIG. 12) monitored at 385 nm are obtained with the blue-green material produced by E. coli strains TOP10 or BL21 transformed with and expressing HO1-pET101 or HemA-HO-1 pET101, respectively (FIG. 12). An HPLC peak with an Rf value of 13.19 is obtained with the biliverdin commercial standard indicating that the blue-green material contains biliverdin in high concentration. Finally, mass spectral analyses of the purified blue-green material reveal a predominant molecular mass of 583.2-583.3 which is the expected monoisotopic mass of biliverdin IXα and that was also observed with the biliverdin IXα commercial standard (FIG. 13). Altogether, the analytical results show that E. coli strains TOP10 or BL21 transformed with and expressing HO1-pET101 or HemA-HO-1 pET101, respectively, produce biliverdin IXα when grown as described.

Example 5

Other Factors which Influence the Production of Biliverdin

The effect of trace metals on biliverdin production was tested. A trace metal solution consisting of (per L) NaCl, 5 g; $ZnSO_4$-$7H_2O$, 1 g; $MnCl_2$-$4H_2O$, 4 g; $FeCl_3$-$6H_2O$, 4.75 g; $CuSO_4$-$5H_2O$, 0.4 g; $H_3BO_3$, 0.575 g; $NaMoO_4$-$2H_2O$, 0.5 g; and 6N $H_2SO_4$, ~12.5 ml) was added to the growth medium. The amount of biliverdin recovered with different amounts of trace metal solution added is reported in Table 3.

TABLE 3

Effect of trace metal solution addition on biliverdin production

| trace metals solution (mL $L^{-1}$) | Average amount BVIXα produced (mg $L^{-1}$) | Range BVIXα produced (mg $L^{-1}$) |
| --- | --- | --- |
| 0 | <0.1 | <0.1 |
| 1.0 | 7.0 | 2.0-9.2 |
| 2.0 | 12 | 4.5-20 |

Figure 15:
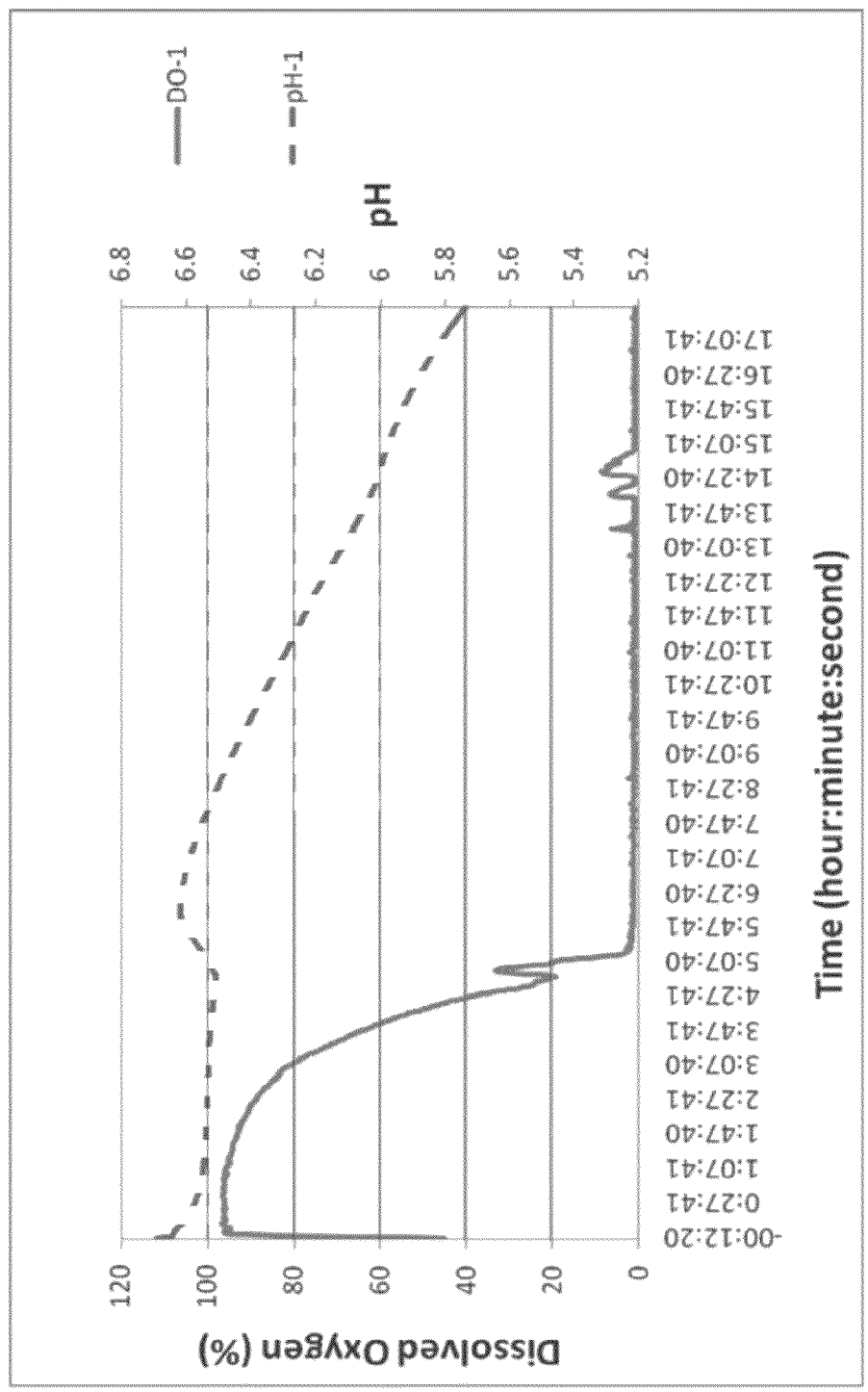
FIG. 15 shows dissolved oxygen (DO-1) and pH (pH-1) in growth medium of *Escherichia coli* cells during biliverdin production.

The concentration of dissolved oxygen during biliverdin production was also tested. $dO_2$ was measured by InPro® 6800 Series $O_2$Sensors (METTLER TOLEDO) connected to BIOFLO® 310 Fermentation System (New Brunswick Scientific). The results are plotted in FIG. 15. In general, the dissolved oxygen profile seen in FIG. 15 is associated with the production of biliverdin. In particular, the small spike (or peak) in oxygen concentration seen at about 5:07:40 is correlated with biliverdin production. Thus, if the dissolved oxygen concentration decreases from its initial value to a first intermediate value, then increases to a second intermediate value higher than the first intermediate value, then decreases to a third intermediate value lower than the first intermediate value, it is expected that the cells in the culture will produce biliverdin.

Example 6

Biliverdin Production Using an Optimized Polynucleotide Construct

Figure 22:
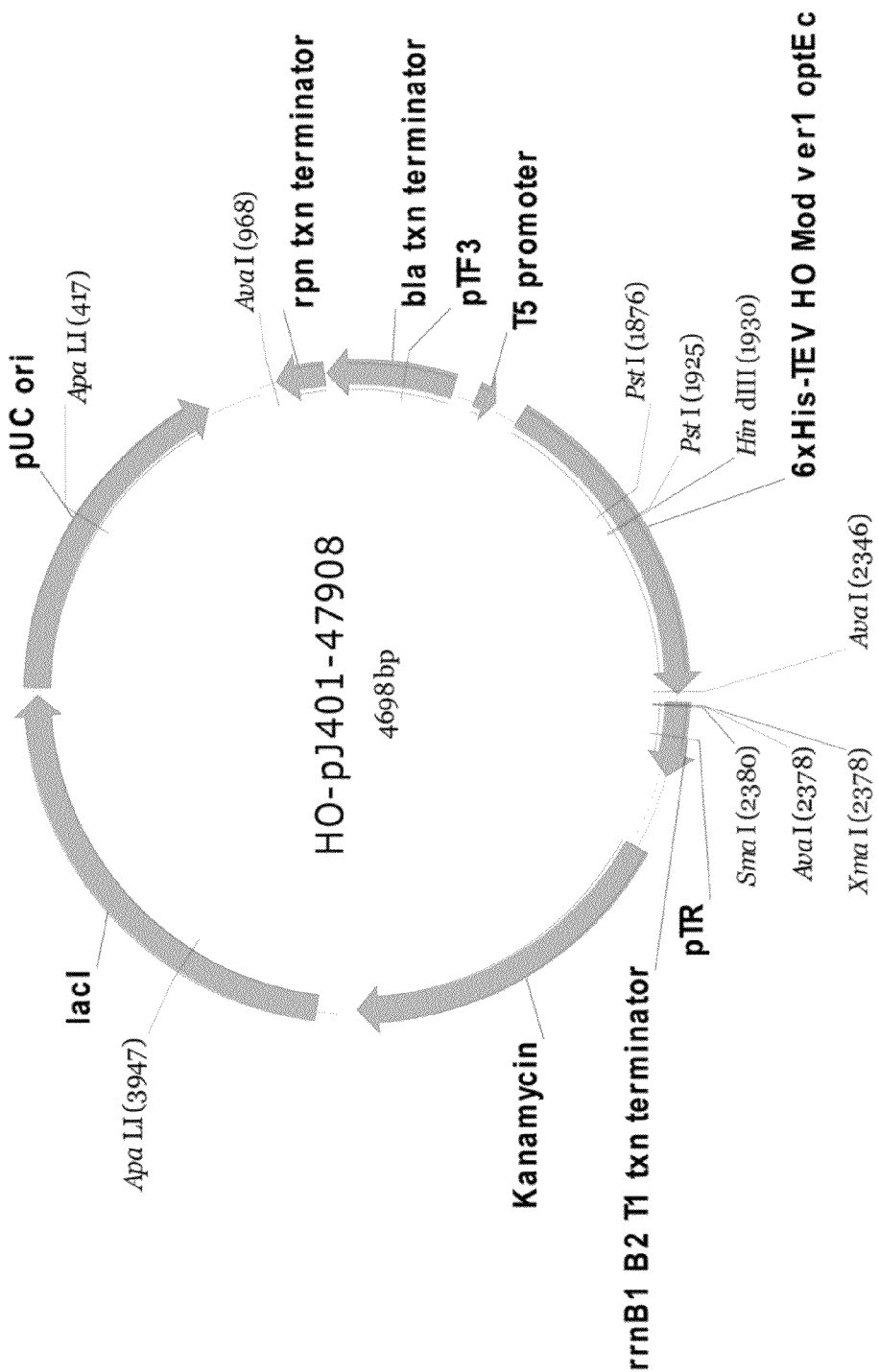
FIG. 22 shows a gene map for the vector HO1-pJ401.

The gene coding for HO1 was optimized to work in *E. coli* and synthesized by DNA 2.0 Inc. (Menlo Park, Calif.). The coding sequence for a 6×His tag was incorporated at the 5' end of the sequence so as to introduce six histidines to the N-terminus of HO1 expressed from the construct (FIG. 20). The synthesized HO1 gene was inserted into Vector pJexpress 401 (DNA 2.0, Menlo Park, Calif.) to form vector HO1-pJ401 (FIG. 22). The vector HO1-pJ401 was transformed into *E. coli* BL21.

For biliverdin production, modified HO1-pJ401 containing *E. coli* strains were grown in 80-ml of LB broth medium plus 100 μg per mL Kanamycin in 250-mL capacity Erlenmeyer flasks in a shaker (225 rpm) at 37° C. to a cell density showing an absorbance of 2 to 6 measured at 600 nm using a 1 cm path length cuvette and LB broth medium as blank. The culture was then added to 2 L medium with 20 g NZamineA (Amersco, Solon Ohio), 10 g Yeast extract (Fisher), 10 ml 100% Glycerol (Amersco, Solon Ohio), 20 ml Lactose 20%, 5 ml Glucose 20%, 10 ml 200× Trace elements, 1 ml 2M $MgSO_4$, and 100 ml 20× NPS (Studier 2006) in NewBrunswick Bioflow 310 controller used with bioCamand software for data collection, 40% dissolved oxygen cascade control (0-30 percent $O_2$ supplemented to airflow, 280-500 rpm agitation, and 0.75-4-slpm airflow), and exponential feed, 200 ml 10% glycerol and 2% lactose feed. Blue-green pigmented material became visible 4 to 10 hours after lactose induction at or near the top of the foam formed above the surface of the culture. Production of biliverdin increased about two fold or more compared to the production in Example 2.

The 200× trace elements solution was prepared by adding to a final volume of 250 ml: 0.5 ml HCl in 50 ml $H_2O$, $FeCl_3$ 0.675 g, $CaCl_2$ 0.15 g, $MnCl_2$ 0.1 g, $ZnSO_4$ 0.015 g, $CoCl_2$ 0.023 g, $CuCl_2$ 0.015 g, $NiCl_2$ 0.023 g, $Na_2MoO_4$ 0.025 g, and $H_3BO_3$ 0.007 g, then filter sterilizing. The 20× NPS stock solution was prepared by dissolving 66 g $(NH_4)_2SO_4$, 136 g $KH_2PO_4$, and 142 g $Na_2HPO_4$ in 1 L dd $H_2O$. The solution was autoclaved at 121° C. 15 min.

It will be apparent to those having skill in the art that many changes may be made to the details of the above-described embodiments without departing from the underlying principles of the invention. The scope of the present invention should, therefore, be determined only by the following claims.

---

The invention claimed is:

1. A method of producing biliverdin from a non-animal source, comprising:

(a) culturing a non-animal cell in a growth medium, the cell comprising a recombinant heme oxygenase and a recombinant heme biosynthetic enzyme; and (b) isolating the biliverdin made in step (a).

2. The method of claim 1, wherein the cell comprises a vector comprising a polynucleotide which codes for the recombinant heme oxygenase.

3. The method of claim 1, wherein the cell comprises a vector comprising a polynucleotide which codes for the recombinant heme biosynthetic enzyme.

4. The method of claim 1, wherein the cell comprises a regulatable promoter operably linked to a polynucleotide which codes for the heme oxygenase.

5. The method of claim 1, wherein the cell comprises a regulatable promoter operably linked to a polynucleotide which codes for the heme biosynthetic enzyme.

6. The method of claim 2, wherein the polynucleotide which codes for the heme oxygenase comprises the polynucleotide of SEQ ID NO: 50.

7. The method of claim 1, wherein the heme biosynthetic enzyme is an aminolevulinic acid synthase (ALA synthase).

8. The method of claim 1, wherein the heme oxygenase is a HO family enzyme.

9. The method of claim 1, wherein the heme biosynthetic enzyme is ALA synthase from *Rhodobacter sphaeroides* (hemA).

10. The method of claim 1, wherein the heme oxygenase enzyme is HO1.

11. A method of determining that the recombinant non-animal cell of claim 1 makes biliverdin, comprising the steps of: taking at least an initial measurement, a first intermediate measurement, a second intermediate measurement, and a third intermediate measurement of dissolved oxygen concentration in the growth medium of the cell, wherein the initial measurement yields an initial value, the first intermediate measurement yields a first intermediate value less than the initial value, the second intermediate measurement yields a second intermediate value greater than the first intermediate value, and the third intermediate measurement yields a third intermediate value less than the first intermediate value, and wherein dissolved oxygen concentrations in the growth medium at the initial value, the first intermediate value, the second intermediate value and the third intermediate value indicate that biliverdin is produced.

* * * * *

SEQUENCE LISTING

<160> NUMBER OF SEQ ID NOS: 50

<210> SEQ ID NO 1
<211> LENGTH: 240
<212> TYPE: PRT
<213> ORGANISM: Synechocystis PCC6803

<400> SEQUENCE: 1

```
Met Ser Val Asn Leu Ala Ser Gln Leu Arg Glu Gly Thr Lys Lys Ser
1               5                   10                  15

His Ser Met Ala Glu Asn Val Gly Phe Val Lys Cys Phe Leu Lys Gly
            20                  25                  30

Val Val Glu Lys Asn Ser Tyr Arg Lys Leu Val Gly Asn Leu Tyr Phe
        35                  40                  45

Val Tyr Ser Ala Met Glu Glu Met Ala Lys Phe Lys Asp His Pro
    50                  55                  60

Ile Leu Ser His Ile Tyr Phe Pro Glu Leu Asn Arg Lys Gln Ser Leu
65                  70                  75                  80

Glu Gln Asp Leu Gln Phe Tyr Tyr Gly Ser Asn Trp Arg Gln Glu Val
                85                  90                  95

Lys Ile Ser Ala Ala Gly Gln Ala Tyr Val Asp Arg Val Arg Gln Val
            100                 105                 110

Ala Ala Thr Ala Pro Glu Leu Leu Val Ala His Ser Tyr Thr Arg Tyr
        115                 120                 125

Leu Gly Asp Leu Ser Gly Gly Gln Ile Leu Lys Lys Ile Ala Gln Asn
    130                 135                 140

Ala Met Asn Leu His Asp Gly Gly Thr Ala Phe Tyr Glu Phe Ala Asp
145                 150                 155                 160

Ile Asp Asp Glu Lys Ala Phe Lys Asn Thr Tyr Arg Gln Ala Met Asn
                165                 170                 175

Asp Leu Pro Ile Asp Gln Ala Thr Ala Glu Arg Ile Val Asp Glu Ala
            180                 185                 190

Asn Asp Ala Phe Ala Met Asn Met Lys Met Phe Asn Glu Leu Glu Gly
```

```
                195                 200                 205
Asn Leu Ile Lys Ala Ile Gly Ile Met Val Phe Asn Ser Leu Thr Arg
    210                 215                 220
Arg Arg Ser Gln Gly Ser Thr Glu Val Gly Leu Ala Thr Ser Glu Gly
225                 230                 235                 240

<210> SEQ ID NO 2
<211> LENGTH: 407
<212> TYPE: PRT
<213> ORGANISM: Rhodobacter sphaeroides

<400> SEQUENCE: 2

Met Asp Tyr Asn Leu Ala Leu Asp Thr Ala Leu Asn Arg Leu His Thr
1               5                   10                  15

Glu Gly Arg Tyr Arg Thr Phe Ile Asp Ile Glu Arg Lys Gly Ala
            20                  25                  30

Phe Pro Lys Ala Met Trp Arg Lys Pro Asp Gly Ser Glu Lys Glu Ile
        35                  40                  45

Thr Val Trp Cys Gly Asn Asp Tyr Leu Gly Met Gly Gln His Pro Val
    50                  55                  60

Val Leu Gly Ala Met His Glu Ala Leu Asp Ser Thr Gly Ala Gly Ser
65                  70                  75                  80

Gly Gly Thr Arg Asn Ile Ser Gly Thr Thr Leu Tyr His Lys Arg Leu
                85                  90                  95

Glu Ala Glu Leu Ala Asp Leu His Gly Lys Glu Ala Ala Leu Val Phe
            100                 105                 110

Ser Ser Ala Tyr Ile Ala Asn Asp Ala Thr Leu Ser Thr Leu Pro Gln
        115                 120                 125

Leu Ile Pro Gly Leu Val Ile Val Ser Asp Lys Leu Asn His Ala Ser
    130                 135                 140

Met Ile Glu Gly Ile Arg Arg Ser Gly Thr Glu Lys His Ile Phe Lys
145                 150                 155                 160

His Asn Asp Leu Asp Asp Leu Arg Arg Ile Leu Thr Ser Ile Gly Lys
                165                 170                 175

Asp Arg Pro Ile Leu Val Ala Phe Glu Ser Val Tyr Ser Met Asp Gly
            180                 185                 190

Asp Phe Gly Arg Ile Glu Glu Ile Cys Asp Ile Ala Asp Glu Phe Gly
        195                 200                 205

Ala Leu Lys Tyr Ile Asp Glu Val His Ala Val Gly Met Tyr Gly Pro
    210                 215                 220

Arg Gly Gly Gly Val Ala Glu Arg Asp Gly Leu Met Asp Arg Ile Asp
225                 230                 235                 240

Ile Ile Asn Gly Thr Leu Gly Lys Ala Tyr Gly Val Phe Gly Gly Tyr
                245                 250                 255

Ile Ala Ala Ser Ser Lys Met Cys Asp Ala Val Arg Ser Tyr Ala Pro
            260                 265                 270

Gly Phe Ile Phe Ser Thr Ser Leu Pro Pro Val Val Ala Ala Gly Ala
        275                 280                 285

Ala Ala Ser Val Arg His Leu Lys Gly Asp Val Glu Leu Arg Glu Lys
    290                 295                 300

His Gln Thr Gln Ala Arg Ile Leu Lys Met Arg Leu Lys Gly Leu Gly
305                 310                 315                 320

Leu Pro Ile Ile Asp His Gly Ser His Ile Val Pro Val His Val Gly
                325                 330                 335

Asp Pro Val His Cys Lys Met Ile Ser Asp Met Leu Leu Glu His Phe
```

-continued

```
                340                 345                 350
Gly Ile Tyr Val Gln Pro Ile Asn Phe Pro Thr Val Pro Arg Gly Thr
        355                 360                 365

Glu Arg Leu Arg Phe Thr Pro Ser Pro Val His Asp Ser Gly Met Ile
370                 375                 380

Asp His Leu Val Lys Ala Met Asp Val Leu Trp Gln His Cys Ala Leu
385                 390                 395                 400

Asn Arg Ala Glu Val Val Ala
            405

<210> SEQ ID NO 3
<211> LENGTH: 24
<212> TYPE: DNA
<213> ORGANISM: Artificial Sequence
<220> FEATURE:
<223> OTHER INFORMATION: PCR primer

<400> SEQUENCE: 3
caccatgagt gtcaacttag cttc                                          24

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
ctagccttcg gaggtggcga                                               20

<210> SEQ ID NO 5
<211> LENGTH: 44
<212> TYPE: DNA
<213> ORGANISM: Artificial Sequence
<220> FEATURE:
<223> OTHER INFORMATION: PCR primer

<400> SEQUENCE: 5
acaacgttga aggagccctt ctccatggac tacaatctgg cact                    44

<210> SEQ ID NO 6
<211> LENGTH: 32
<212> TYPE: DNA
<213> ORGANISM: Artificial Sequence
<220> FEATURE:
<223> OTHER INFORMATION: PCR primer

<400> SEQUENCE: 6
atgaccggta cgtcaggcaa cgacctcggc gc                                 32

<210> SEQ ID NO 7
<211> LENGTH: 239
<212> TYPE: PRT
<213> ORGANISM: Cyanothece ATCC51142

<400> SEQUENCE: 7

Met Ser Val Asn Leu Ala Thr Met Leu Arg Glu Gly Thr Lys Lys Ser
1               5                   10                  15

His Thr Met Ala Glu Asn Val Gly Phe Val Lys Cys Phe Leu Lys Gly
            20                  25                  30

Val Val Glu Lys Asn Ser Tyr Arg Thr Leu Val Ala Asn Leu Tyr Phe
        35                  40                  45

Val Tyr Ser Ala Met Glu Glu Glu Met Glu Lys Leu Arg His His Glu
```

```
                50                  55                  60
Leu Val Ser Lys Ile Tyr Phe Pro Gln Leu His Arg Lys Gln Ser Leu
 65                  70                  75                  80

Glu Lys Asp Leu Cys Phe Tyr Tyr Gly Ala Asn Trp Arg Asn Glu Val
                 85                  90                  95

Ala Pro Ser Lys Ala Ala Gln Ala Tyr Val Ala Arg Ile His Glu Val
                100                 105                 110

Ala Gln Thr Gln Pro Glu Leu Leu Ala Ala His Ser Tyr Thr Arg Tyr
            115                 120                 125

Leu Gly Asp Leu Ser Gly Gly Gln Ile Leu Lys Lys Ile Ala Gln Arg
130                 135                 140

Ala Met Asn Leu Gly Glu Asn Gly Gly Thr Ala Phe Tyr Glu Phe Glu
145                 150                 155                 160

Thr Ile Ser Asp Glu Lys Ala Phe Lys Asn Glu Tyr Arg Gln Ala Leu
                165                 170                 175

Asn Glu Leu Pro Ile Asp Glu Ala Thr Ala Lys Ile Val Asp Glu
            180                 185                 190

Ala Asn Ala Ala Phe Gly Met Asn Met Lys Met Phe Met Glu Leu Glu
            195                 200                 205

Gly Asn Leu Ile Lys Ala Ile Gly Ile Met Leu Phe Asn Thr Leu Thr
210                 215                 220

Arg Arg Arg Ser Lys Gly Ser Thr Glu Leu Ala Gly Ala Glu Gln
225                 230                 235

<210> SEQ ID NO 8
<211> LENGTH: 240
<212> TYPE: PRT
<213> ORGANISM: Synechococcus PCC7002

<400> SEQUENCE: 8

Met Val Ala Asn Leu Ala Thr Met Leu Arg Glu Gly Thr Lys Thr Ser
 1               5                  10                  15

His Thr Met Ala Glu Asn Val Gly Phe Val Lys Cys Phe Leu Lys Gly
                20                  25                  30

Val Val Glu Lys Lys Ser Tyr Arg Lys Leu Val Ala Asp Leu Tyr Tyr
                35                  40                  45

Val Tyr Ser Ala Met Glu Glu Glu Met Glu Arg Leu Lys Asp His Pro
 50                  55                  60

Val Val Ser Gln Ile Tyr Phe Pro Glu Leu Asn Arg Lys Gln Ser Leu
 65                  70                  75                  80

Glu Thr Asp Leu Arg Tyr Tyr Phe Gly Pro Asn Trp Gln Ala Glu Ala
                 85                  90                  95

Lys Ile Thr Pro Ala Gly Gln Ala Tyr Val Asp Arg Ile His Glu Val
                100                 105                 110

Ala Gln Thr Ala Pro Glu Leu Leu Val Ser His Ser Tyr Thr Arg Tyr
            115                 120                 125

Leu Gly Asp Leu Ser Gly Gly Gln Ile Leu Lys Lys Ile Ala Gln Asn
130                 135                 140

Ala Met Asn Leu Asp Gly Glu Gly Thr Ala Phe Tyr Glu Phe Glu Asn
145                 150                 155                 160

Ile Ser Asp Glu Lys Ala Phe Lys Asp Lys Tyr Arg Ala Ala Met Asn
                165                 170                 175

Ser Leu Asp Val Pro Glu Glu Thr Ala Glu Gln Ile Val Gln Glu Ala
            180                 185                 190

Asn Asp Ala Phe Gly Met Asn Met Asn Met Phe Lys Glu Leu Glu Gly
```

-continued

```
        195                 200                 205

Asn Leu Val Lys Ala Ile Gly Val Met Leu Phe Asn Thr Leu Thr Arg
    210                 215                 220

Arg Arg Thr Lys Gly Ser Thr Asp Ala Asp Leu Ser Pro Ala Ser Asn
225                 230                 235                 240

<210> SEQ ID NO 9
<211> LENGTH: 238
<212> TYPE: PRT
<213> ORGANISM: Anabaena PCC7120

<400> SEQUENCE: 9

Met Ser Ser Asn Leu Ala Asn Lys Leu Arg Val Gly Thr Lys Lys Ala
1               5                   10                  15

His Thr Met Ala Glu Asn Val Gly Phe Val Lys Cys Phe Leu Lys Gly
            20                  25                  30

Val Val Glu Lys Ser Ser Tyr Arg Lys Leu Val Ala Asn Phe Tyr Tyr
        35                  40                  45

Val Tyr Ser Ala Met Glu Glu Glu Met Glu Lys His Ser Gln His Pro
    50                  55                  60

Ile Val Ser Lys Ile Asn Phe Ser Gln Leu Asn Arg Lys Gln Thr Leu
65                  70                  75                  80

Glu Gln Asp Leu Ser Tyr Tyr Tyr Gly Ala Asn Trp Arg Glu Gln Ile
                85                  90                  95

Gln Leu Ser Pro Ala Gly Glu Ala Tyr Val Gln Arg Ile Arg Glu Ile
            100                 105                 110

Ser Ala Thr Glu Pro Glu Leu Leu Ile Ala His Ser Tyr Thr Arg Tyr
        115                 120                 125

Leu Gly Asp Leu Ser Gly Gly Gln Ile Leu Lys Asn Ile Ala Val Thr
    130                 135                 140

Ala Met Asn Leu Asn Asp Gly Gln Gly Thr Ala Phe Tyr Glu Phe Ala
145                 150                 155                 160

Asp Ile Ser Asp Glu Lys Ala Phe Lys Ala Lys Tyr Arg Gln Thr Leu
                165                 170                 175

Asp Glu Leu Ala Ile Asp Glu Ala Thr Gly Asp Arg Ile Val Asp Glu
            180                 185                 190

Ala Asn Ala Ala Phe Gly Met Asn Met Lys Met Phe Gln Glu Leu Glu
        195                 200                 205

Gly Asn Leu Ile Lys Ala Ile Gly Met Met Leu Phe Asn Thr Leu Thr
    210                 215                 220

Arg Lys Arg Thr Arg Gly Ala Thr Glu Leu Ala Thr Ala Glu
225                 230                 235

<210> SEQ ID NO 10
<211> LENGTH: 215
<212> TYPE: PRT
<213> ORGANISM: Corynebacterium diphtheriae

<400> SEQUENCE: 10

Met Thr Thr Ala Thr Ala Gly Leu Ala Val Glu Leu Lys Gln Ser Thr
1               5                   10                  15

Ala Gln Ala His Glu Lys Ala Glu His Ser Thr Phe Met Ser Asp Leu
            20                  25                  30

Leu Lys Gly Arg Leu Gly Val Ala Glu Phe Thr Arg Leu Gln Glu Gln
        35                  40                  45

Ala Trp Leu Phe Tyr Thr Ala Leu Glu Gln Ala Val Asp Ala Val Arg
    50                  55                  60
```

```
Ala Ser Gly Phe Ala Glu Ser Leu Leu Asp Pro Ala Leu Asn Arg Ala
 65                  70                  75                  80

Glu Val Leu Ala Arg Asp Leu Asp Lys Leu Asn Gly Ser Ser Glu Trp
                 85                  90                  95

Arg Ser Arg Ile Thr Ala Ser Pro Ala Val Ile Asp Tyr Val Asn Arg
            100                 105                 110

Leu Glu Glu Ile Arg Asp Asn Val Asp Gly Pro Ala Leu Val Ala His
        115                 120                 125

His Tyr Val Arg Tyr Leu Gly Asp Leu Ser Gly Gln Val Ile Ala
    130                 135                 140

Arg Met Met Gln Arg His Tyr Gly Val Asp Pro Glu Ala Leu Gly Phe
145                 150                 155                 160

Tyr His Phe Glu Gly Ile Ala Lys Leu Lys Val Tyr Lys Asp Glu Tyr
                165                 170                 175

Arg Glu Lys Leu Asn Asn Leu Glu Leu Ser Asp Glu Gln Arg Glu His
            180                 185                 190

Leu Leu Lys Glu Ala Thr Asp Ala Phe Val Phe Asn His Gln Val Phe
        195                 200                 205

Ala Asp Leu Gly Lys Gly Leu
    210                 215

<210> SEQ ID NO 11
<211> LENGTH: 250
<212> TYPE: PRT
<213> ORGANISM: Synechocystis PCC6803

<400> SEQUENCE: 11

Met Thr Asn Leu Ala Gln Lys Leu Arg Tyr Gly Thr Gln Gln Ser His
  1               5                  10                  15

Thr Leu Ala Glu Asn Thr Ala Tyr Met Lys Cys Phe Leu Lys Gly Ile
                 20                  25                  30

Val Glu Arg Glu Pro Phe Arg Gln Leu Leu Ala Asn Leu Tyr Tyr Leu
             35                  40                  45

Tyr Ser Ala Leu Glu Ala Ala Leu Arg Gln His Arg Asp Asn Glu Ile
 50                  55                  60

Ile Ser Ala Ile Tyr Phe Pro Glu Leu Asn Arg Thr Asp Lys Leu Ala
 65                  70                  75                  80

Glu Asp Leu Thr Tyr Tyr Tyr Gly Pro Asn Trp Gln Gln Ile Ile Gln
                 85                  90                  95

Pro Thr Pro Cys Ala Lys Ile Tyr Val Asp Arg Leu Lys Thr Ile Ala
            100                 105                 110

Ala Ser Glu Pro Glu Leu Leu Ile Ala His Cys Tyr Thr Arg Tyr Leu
        115                 120                 125

Gly Asp Leu Ser Gly Gly Gln Ser Leu Lys Asn Ile Ile Arg Ser Ala
    130                 135                 140

Leu Gln Leu Pro Glu Gly Glu Gly Thr Ala Met Tyr Glu Phe Asp Ser
145                 150                 155                 160

Leu Pro Thr Pro Gly Asp Arg Arg Gln Phe Lys Glu Ile Tyr Arg Asp
                165                 170                 175

Val Leu Asn Ser Leu Pro Leu Asp Glu Ala Thr Ile Asn Arg Ile Val
            180                 185                 190

Glu Glu Ala Asn Tyr Ala Phe Ser Leu Asn Arg Glu Val Met His Asp
        195                 200                 205

Leu Glu Asp Leu Ile Lys Ala Ala Ile Gly Glu His Thr Phe Asp Leu
    210                 215                 220
```

Leu Thr Arg Gln Asp Arg Pro Gly Ser Thr Glu Ala Arg Ser Thr Ala
225                 230                 235                 240

Gly His Pro Ile Thr Leu Met Val Gly Glu
                245                 250

<210> SEQ ID NO 12
<211> LENGTH: 312
<212> TYPE: PRT
<213> ORGANISM: Oryctolagus cuniculus

<400> SEQUENCE: 12

Met Ser Ala Glu Val Glu Thr Ser Glu Gly Val Asp Glu Pro Glu Glu
1               5                   10                  15

Lys Asn Phe Gly Glu Asn His Ile Arg Met Ala Asp Leu Ser Glu Leu
            20                  25                  30

Leu Lys Glu Gly Thr Lys Glu Ala His Asp Arg Ala Glu Asn Thr Lys
        35                  40                  45

Phe Val Lys Asp Phe Leu Lys Gly Asn Ile Lys Lys Glu Ile Phe Lys
    50                  55                  60

Leu Ala Thr Thr Ala Leu Tyr Phe Thr Tyr Ser Ala Leu Glu Glu Glu
65                  70                  75                  80

Met Asp Arg Asn Lys Asp His Pro Ala Phe Ala Pro Leu Tyr Phe Pro
                85                  90                  95

Met Glu Leu His Arg Lys Glu Ala Leu Thr Lys Asp Met Glu Tyr Phe
            100                 105                 110

Phe Gly Glu Asn Trp Glu Glu Gln Val Gln Cys Ser Glu Ala Ala Gln
        115                 120                 125

Lys Tyr Val Glu Arg Ile His Tyr Ile Gly Gln Asn Glu Pro Glu Leu
    130                 135                 140

Leu Val Ala His Ala Tyr Thr Arg Tyr Met Gly Asp Leu Ser Gly Gly
145                 150                 155                 160

Gln Val Leu Lys Lys Val Ala Gln Arg Ala Leu Lys Leu Pro Ser Thr
                165                 170                 175

Gly Glu Gly Thr Gln Phe Tyr Leu Phe Glu Asn Val Asp Asn Ala Gln
            180                 185                 190

Gln Phe Lys Gln Phe Tyr Arg Ala Arg Met Asn Ala Leu Asp Leu Asn
        195                 200                 205

Leu Lys Thr Lys Glu Arg Ile Val Glu Glu Ala Asn Lys Ala Phe Glu
    210                 215                 220

Tyr Asn Met Gln Ile Phe Ser Glu Leu Asp Gln Ala Gly Ser Ala Pro
225                 230                 235                 240

Ala Ser Glu Thr Val Glu Asp Arg Ile Pro Val His Asp Gly Lys Gly
                245                 250                 255

Asp Val Arg Lys Cys Pro Tyr Tyr Ala Ala Gly Gln Val Asn Gly Ala
            260                 265                 270

Leu Glu Gly Ser Ser Cys Pro Phe Arg Ala Ala Met Ala Val Leu Arg
        275                 280                 285

Lys Pro Ser Leu Gln Leu Val Leu Ala Ala Val Ala Leu Ala Ala
    290                 295                 300

Gly Leu Leu Ala Trp Tyr Tyr Met
305                 310

<210> SEQ ID NO 13
<211> LENGTH: 198
<212> TYPE: PRT
<213> ORGANISM: Pseudomonas aeruginosa

```
<400> SEQUENCE: 13

Met Asp Thr Leu Ala Pro Glu Ser Thr Arg Gln Asn Leu Arg Ser Gln
1               5                   10                  15

Arg Leu Asn Leu Leu Thr Asn Glu Pro His Gln Arg Leu Glu Ser Leu
            20                  25                  30

Val Lys Ser Lys Glu Pro Phe Ala Ser Arg Asp Asn Phe Ala Arg Phe
        35                  40                  45

Val Ala Ala Gln Tyr Leu Phe Gln His Asp Leu Glu Pro Leu Tyr Arg
    50                  55                  60

Asn Glu Ala Leu Ala Arg Leu Phe Pro Gly Leu Ala Ser Arg Ala Arg
65                  70                  75                  80

Asp Asp Ala Ala Arg Ala Asp Leu Ala Asp Leu Gly His Pro Val Pro
                85                  90                  95

Glu Gly Asp Gln Ser Val Arg Glu Ala Asp Leu Ser Leu Ala Glu Ala
            100                 105                 110

Leu Gly Trp Leu Phe Val Ser Glu Gly Ser Lys Leu Gly Ala Ala Phe
        115                 120                 125

Leu Phe Lys Lys Ala Ala Ala Leu Glu Leu Asp Glu Asn Phe Gly Ala
    130                 135                 140

Arg His Leu Ala Glu Pro Glu Gly Gly Arg Ala Gln Gly Trp Lys Ser
145                 150                 155                 160

Phe Val Ala Ile Leu Asp Gly Ile Glu Leu Asn Glu Glu Glu Arg
                165                 170                 175

Leu Ala Ala Lys Gly Ala Ser Asp Ala Phe Asn Arg Phe Gly Asp Leu
            180                 185                 190

Leu Glu Arg Thr Phe Ala
        195

<210> SEQ ID NO 14
<211> LENGTH: 277
<212> TYPE: PRT
<213> ORGANISM: Fugu rubripes

<400> SEQUENCE: 14

Met Glu Ala Asp Lys Lys Thr Thr Ala Gln Thr Glu Ser Asn Arg Asp
1               5                   10                  15

Leu Ser Glu Gln Ile Lys Lys Val Thr Lys Asp Val His Val Arg Ala
            20                  25                  30

Glu Ser Thr Glu Leu Met Leu Ser Phe Gln Arg Gly Gln Val Thr Leu
        35                  40                  45

Gln Gln Tyr Lys Leu Leu Leu Cys Ser Leu Tyr Glu Ile Tyr Leu Ala
    50                  55                  60

Leu Glu Glu Glu Met Asp Arg Asn Cys Asp His Pro Ser Val Ala Pro
65                  70                  75                  80

Ile Tyr Phe Pro Ala Glu Leu Ala Arg Leu Ala Thr Ile Glu Lys Asp
                85                  90                  95

Leu Glu Phe Phe Phe Gly Pro Asp Trp Arg Glu Lys Ile Val Val Pro
            100                 105                 110

Ala Ala Thr Glu Arg Tyr Cys His Arg Ile Arg Gln Ile Gly Gln Glu
        115                 120                 125

Asn Pro Glu Tyr Leu Ile Ala His Ala Tyr Thr Arg Tyr Leu Gly Asp
    130                 135                 140

Leu Ser Gly Gly Gln Val Leu Gly Arg Ile Ala Gln Lys Ser Met Lys
145                 150                 155                 160
```

```
Leu Gly Gly Ser Glu Gly Leu Ser Phe Phe Ala Phe Pro Gly Val Ser
                165                 170                 175

Ser Pro Asn Leu Phe Lys Arg Leu Tyr Arg Ser Arg Met Asn Ser Val
            180                 185                 190

Glu Leu Thr Glu Glu Gln Arg Ser Ala Val Leu Gln Glu Ala Leu Gly
        195                 200                 205

Ala Phe Glu Phe Asn Ile Gln Val Phe Glu Asp Leu Gln Lys Met Leu
    210                 215                 220

Asn Val Thr Glu Asn Glu Pro Gly Val Gly Thr Pro Arg Ser Arg Pro
225                 230                 235                 240

Ala Thr Thr Leu Gln Val Gly Ser Met Ile Gln Thr Asn Pro Leu
                245                 250                 255

Phe Arg Met Val Leu Gly Leu Cys Leu Ala Leu Ala Thr Val Ser Ile
            260                 265                 270

Gly Leu Tyr Ala Leu
            275

<210> SEQ ID NO 15
<211> LENGTH: 296
<212> TYPE: PRT
<213> ORGANISM: Drosophila melanogaster

<400> SEQUENCE: 15

Met Ser Ala Ser Glu Glu Thr Ile Ala Asp Ser Gln Val Ser Glu Asn
1               5                   10                  15

Val Glu Asp Val Glu Phe Val Asp Met Ala Phe Thr Lys Glu Leu Arg
            20                  25                  30

Lys Ala Thr Lys Asp Val His Asn Leu Thr Asp Val Leu Val Asn Ala
        35                  40                  45

Lys Ile Ala Leu Ala Leu Ser Asp Asp Glu Val Trp Tyr Asp Gly Leu
    50                  55                  60

Leu Ala Phe Tyr Glu Leu Tyr Lys Phe Glu Thr His Leu Pro Glu
65                  70                  75                  80

Arg Leu Leu Pro Lys Glu Phe His Arg Thr Ala Ala Phe Glu Arg Asp
                85                  90                  95

Phe Ala Tyr Phe Tyr Gly Ser Asp Trp Arg Lys Asp Tyr Glu Ile Arg
            100                 105                 110

Pro Ala Val Gln Lys Tyr Leu Glu His Leu Glu Lys Ile Ala Ala Gln
        115                 120                 125

Asn Glu Leu Leu Leu Phe Ala Tyr Ser Tyr Gln Met Tyr Met Ala Leu
    130                 135                 140

Met Ser Gly Gly Gln Met Leu Gln Lys Lys Arg Met Ile Ala Arg Lys
145                 150                 155                 160

Met Trp Ile Phe Ser Lys Asn Asp Asp Glu Glu Gln Lys Gln Ala
                165                 170                 175

Asp Lys Glu Ala Glu Leu Ala Thr Ala Arg Ala Ala Asp Gly Ser Val
            180                 185                 190

Asp Lys Asp Asp Leu Glu Ala Arg Pro Met Pro Ala Gln Val Thr Ile
        195                 200                 205

Cys Pro Pro Gly Cys Glu Ala Thr Tyr Phe Pro Glu Lys Ile Ser Val
    210                 215                 220

Leu Lys Ala Lys Leu Arg Arg Val Phe Asn Asn His Tyr Gly Ala Phe
225                 230                 235                 240

Asp Asp Asp Leu Arg Ala Ala Phe Ile Glu Glu Ser Arg Asn Val Phe
                245                 250                 255
```

```
Arg Leu Asn Ile Glu Val Val Arg Thr Ile Lys Gly Val Asn Arg Ala
            260                 265                 270

Asn Leu Arg Lys Leu Ala Leu Ala Leu Ile Phe Val Ser Ser Ile Val
            275                 280                 285

Val Ala Val Lys Phe Ala Leu Lys
            290                 295

<210> SEQ ID NO 16
<211> LENGTH: 202
<212> TYPE: PRT
<213> ORGANISM: Bradyrhizobium sp. ORS278

<400> SEQUENCE: 16

Met Arg Glu Arg Thr Lys Thr Leu His Val Thr Ala Glu Arg Thr Gly
1               5                   10                  15

Val Val Ala Glu Leu Leu Arg Gly Arg Gly Thr Val Arg Ala Tyr Ala
            20                  25                  30

Leu Leu Leu Arg Asn Leu Leu Pro Val Tyr Glu Ala Leu Glu Ala Glu
            35                  40                  45

Leu Val Arg His Gln Ala Ser Pro Val Val Gly Leu Thr Val Arg Pro
        50                  55                  60

Glu Leu His Arg Cys Pro Ala Ile Lys Ala Asp Leu Ala Ala Leu Asp
65                  70                  75                  80

Ala Ser Asp Leu Pro Leu Leu Pro Glu Ala Ile Ala Tyr Val Arg Ala
                85                  90                  95

Ile Gln Glu Ala Gly Ser Gly Ser Gly His Pro Leu Leu Ala His Ala
            100                 105                 110

Tyr Thr Arg Tyr Leu Gly Asp Leu Ser Gly Gly Gln Ile Ile Lys Lys
            115                 120                 125

Ile Leu Ala Arg Ser Leu Glu Leu Gln Pro Glu Ala Leu Ser Phe Tyr
        130                 135                 140

Glu Phe Pro Ala Ile Thr Asp Ile Pro Arg Phe Lys Thr Glu Tyr Arg
145                 150                 155                 160

Glu Ala Leu Glu Gln Ala Gly Ser Ala Met Thr Glu His Asp Ser Val
                165                 170                 175

Val Glu Glu Ala Ala Thr Ala Phe Gln Leu Asn Ile Thr Leu Ser Gln
            180                 185                 190

Ala Leu Gln Ser Ala Ala Gly Leu Gly Arg
            195                 200

<210> SEQ ID NO 17
<211> LENGTH: 195
<212> TYPE: PRT
<213> ORGANISM: Pseudomonas aeruginosa

<400> SEQUENCE: 17

Met Ser Pro Ser Pro Ser Pro Ala Leu Ala Ala Leu Arg Asp Ala Thr
1               5                   10                  15

Arg Asp Leu His Ala Glu Leu Asp Arg Arg Ser Pro Leu Gly Asp Asp
            20                  25                  30

Asp Leu Asp Asp Arg Ala Tyr Leu Asp His Ala Gly Arg Ile Leu Gly
            35                  40                  45

Trp Leu Glu Pro Leu Glu Arg Ala Leu Arg Asp Asn Arg Ser Gly Trp
        50                  55                  60

Pro Ala Ala Leu Arg Ala Asp Ala Arg Leu Val Lys Ser Thr Trp Leu
65                  70                  75                  80

Glu Ser Asp Leu Leu Ala Gly Gly Met Ser Arg Ala Gln Val Glu Ala
```

```
            85                  90                  95
Leu Pro Arg Cys Ala Asp Leu Pro Asn Ala Thr Arg Ala Ala Glu Val
            100                 105                 110

Phe Gly Val Ala Tyr Val Met Glu Gly Ala Thr Leu Gly Gly Ala Tyr
            115                 120                 125

Leu Tyr Lys Arg Leu Ala Pro Arg Leu Pro Gly Leu Pro Leu Gln Trp
            130                 135                 140

Leu Gln Gly Tyr Gly Gln Ala Thr Gly Val Arg Trp Gln Glu Phe Leu
145                 150                 155                 160

Glu Gln Leu Ala Arg Gln Ile Asp Ser Pro Glu Ala Ile Gly Leu Ala
                165                 170                 175

Gln Asp Ala Ala Gln Ala Thr Phe Leu Ser Phe Arg Arg Trp Val Leu
            180                 185                 190

Asp Glu Ala
            195

<210> SEQ ID NO 18
<211> LENGTH: 215
<212> TYPE: PRT
<213> ORGANISM: Streptomyces coelicolor

<400> SEQUENCE: 18

Met Asp Ser Phe Ser Thr Leu Ile Arg Thr Ala Ser His Gln Gln His
1               5                   10                  15

Val Glu Ala Glu Thr Ser Thr Phe Met Ser Asp Leu Leu Gly Gly Gly
            20                  25                  30

Leu Gly Val Asp Ala Tyr Ala Arg Tyr Thr Glu Gln Leu Trp Phe Val
            35                  40                  45

Tyr Glu Ala Leu Glu Ala Ala Gly Arg Leu Ala Ala Asp Pro Val
50                  55                  60

Ala Gly Pro Phe Val Arg Pro Glu Leu Leu Arg Leu Ala Ser Leu Glu
65                  70                  75                  80

Arg Asp Leu Ala His Leu Arg Gly Ala Asp Trp Arg Thr Gly Leu Thr
                85                  90                  95

Ala Leu Pro Ala Thr Glu Ala Tyr Ala Ala Arg Val Arg Glu Cys Ala
            100                 105                 110

Glu Glu Trp Pro Ala Gly Tyr Val Ala His His Tyr Thr Arg Tyr Leu
            115                 120                 125

Gly Asp Leu Ser Gly Gly Gln Ile Ile Arg Asp Lys Ala Glu Arg Thr
            130                 135                 140

Trp Gly Phe Ala Arg Lys Gly Asp Gly Val Arg Phe Tyr Val Phe Glu
145                 150                 155                 160

Glu Ile Ser Asn Pro Ala Ala Phe Lys Arg Glu Tyr Arg Asp Leu Leu
                165                 170                 175

Asp Gly Ile Arg Ala Asp Asp Leu Glu Lys Gln Arg Val Val Ala Glu
            180                 185                 190

Cys Lys Arg Ala Phe Ala Leu Asn Thr Ala Val Phe Arg Ala Leu Gly
            195                 200                 205

Glu Glu Phe Pro Leu Ser Ala
            210                 215

<210> SEQ ID NO 19
<211> LENGTH: 289
<212> TYPE: PRT
<213> ORGANISM: Bos taurus

<400> SEQUENCE: 19
```

```
Met Glu Arg Pro Gln Pro Asp Ser Ser Met Pro Gln Asp Leu Ser Glu
1               5                   10                  15

Ala Leu Lys Glu Ala Thr Lys Glu Val His Thr Gln Ala Glu Asn Ala
            20                  25                  30

Glu Phe Met Lys Asn Phe Gln Lys Gly Glu Leu Thr Gln Glu Gly Phe
        35                  40                  45

Lys Leu Val Met Ala Ser Leu Tyr His Ile Tyr Val Ala Leu Glu Glu
    50                  55                  60

Glu Ile Glu Arg Asn Lys Glu Asn Pro Val Tyr Thr Pro Leu Tyr Phe
65                  70                  75                  80

Pro Glu Glu Leu His Arg Arg Ala Ser Leu Glu Gln Asp Met Ala Phe
                85                  90                  95

Trp Tyr Gly Pro Arg Trp Gln Glu Ala Ile Pro Tyr Thr Gln Ala Thr
            100                 105                 110

Lys Arg Tyr Val Gln Arg Leu Gln Glu Val Gly Arg Thr Glu Pro Glu
        115                 120                 125

Leu Leu Val Ala His Ala Tyr Thr Arg Tyr Leu Gly Asp Leu Ser Gly
    130                 135                 140

Gly Gln Val Leu Lys Lys Ile Ala Gln Lys Ala Leu Asn Leu Pro Ser
145                 150                 155                 160

Ser Gly Glu Gly Leu Ala Phe Phe Thr Phe Pro Asn Ile Ala Ser Ala
                165                 170                 175

Thr Lys Phe Lys Gln Leu Tyr Arg Ser Arg Met Asn Thr Leu Glu Met
            180                 185                 190

Thr Pro Glu Val Arg Gln Arg Val Leu Asp Glu Ala Lys Thr Ala Phe
        195                 200                 205

Leu Leu Asn Ile Gln Leu Phe Glu Glu Leu Gln Gly Leu Leu Thr Gln
    210                 215                 220

Lys Ala Lys Asp His Asp Pro Leu Gln Ala Pro Glu Leu His Arg Arg
225                 230                 235                 240

Ala Gly Ser Lys Val Gln Asp Leu Ala Pro Thr Lys Ala Ser Arg Gly
                245                 250                 255

Lys Pro Gln Pro Ser Val Leu Ser Gln Ala Pro Leu Leu Arg Trp Val
            260                 265                 270

Leu Thr Leu Ser Phe Leu Val Ala Thr Val Ala Val Gly Leu Tyr Ala
        275                 280                 285

Met

<210> SEQ ID NO 20
<211> LENGTH: 288
<212> TYPE: PRT
<213> ORGANISM: Homo sapiens

<400> SEQUENCE: 20

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
    50                  55                  60

Ile Glu Arg Asn Lys Glu Ser Pro Val Phe Ala Pro Val Tyr Phe Pro
65                  70                  75                  80
```

```
Glu Glu Leu His Arg Lys Ala Ala Leu Glu Gln Asp Leu Ala Phe Trp
            85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
            115                 120                 125

Leu Val Ala His Ala Tyr Thr Arg Tyr Leu Gly Asp Leu Ser Gly Gly
            130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
            165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
            195                 200                 205

Leu Asn Ile Gln Leu Phe Glu Glu Leu Gln Glu Leu Leu Thr His Asp
            210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
            245                 250                 255

Pro Pro Leu Asn Thr Arg Ser Gln Ala Pro Leu Leu Arg Trp Val Leu
            260                 265                 270

Thr Leu Ser Phe Leu Val Ala Thr Val Ala Val Gly Leu Tyr Ala Met
            275                 280                 285

<210> SEQ ID NO 21
<211> LENGTH: 289
<212> TYPE: PRT
<213> ORGANISM: Mus musculus

<400> SEQUENCE: 21

Met Glu Arg Pro Gln Pro Asp Ser Met Pro Gln Asp Leu Ser Glu Ala
1               5                   10                  15

Leu Lys Glu Ala Thr Lys Glu Val His Ile Gln Ala Glu Asn Ala Glu
            20                  25                  30

Phe Met Lys Asn Phe Gln Lys Gly Gln Val Ser Arg Glu Gly Phe Lys
            35                  40                  45

Leu Val Met Ala Ser Leu Tyr His Ile Tyr Thr Ala Leu Glu Glu Glu
            50                  55                  60

Ile Glu Arg Asn Lys Gln Asn Pro Val Tyr Ala Pro Leu Tyr Phe Pro
65                  70                  75                  80

Glu Glu Leu His Arg Arg Ala Ala Leu Glu Gln Asp Met Ala Phe Trp
            85                  90                  95

Tyr Gly Pro His Trp Gln Glu Ile Ile Pro Cys Thr Pro Ala Thr Gln
            100                 105                 110

His Tyr Val Lys Arg Leu His Glu Val Gly Arg Thr His Pro Glu Leu
            115                 120                 125

Leu Val Ala His Ala Tyr Thr Arg Tyr Leu Gly Asp Leu Ser Gly Gly
            130                 135                 140

Gln Val Leu Lys Lys Ile Ala Gln Lys Ala Met Ala Leu Pro Ser Ser
145                 150                 155                 160

Gly Glu Gly Leu Ala Phe Phe Thr Phe Pro Asn Ile Asp Ser Pro Thr
            165                 170                 175
```

```
Lys Phe Lys Gln Leu Tyr Arg Ala Arg Met Asn Thr Leu Glu Met Thr
            180                 185                 190

Pro Glu Val Lys His Arg Val Thr Glu Glu Ala Lys Thr Ala Phe Leu
        195                 200                 205

Leu Asn Ile Glu Leu Phe Glu Glu Leu Gln Val Met Leu Thr Glu Glu
    210                 215                 220

His Lys Asp Gln Ser Pro Ser Gln Met Ala Ser Leu Arg Gln Arg Pro
225                 230                 235                 240

Ala Ser Leu Val Gln Asp Thr Ala Pro Ala Glu Thr Pro Arg Gly Lys
                245                 250                 255

Pro Gln Ile Ser Thr Ser Ser Gln Thr Pro Leu Leu Gln Trp Val
        260                 265                 270

Leu Thr Leu Ser Phe Leu Leu Ala Thr Val Ala Val Gly Ile Tyr Ala
        275                 280                 285

Met

<210> SEQ ID NO 22
<211> LENGTH: 289
<212> TYPE: PRT
<213> ORGANISM: Rattus norvegicus

<400> SEQUENCE: 22

Met Glu Arg Pro Gln Leu Asp Ser Met Ser Gln Asp Leu Ser Glu Ala
1               5                   10                  15

Leu Lys Glu Ala Thr Lys Glu Val His Ile Arg Ala Glu Asn Ser Glu
            20                  25                  30

Phe Met Arg Asn Phe Gln Lys Gly Gln Val Ser Arg Glu Gly Phe Lys
        35                  40                  45

Leu Val Met Ala Ser Leu Tyr His Ile Tyr Thr Ala Leu Glu Glu Glu
    50                  55                  60

Ile Glu Arg Asn Lys Gln Asn Pro Val Tyr Ala Pro Leu Tyr Phe Pro
65                  70                  75                  80

Glu Glu Leu His Arg Arg Ala Ala Leu Glu Gln Asp Met Ala Phe Trp
                85                  90                  95

Tyr Gly Pro His Trp Gln Glu Ala Ile Pro Tyr Thr Pro Ala Thr Gln
            100                 105                 110

His Tyr Val Lys Arg Leu His Glu Val Gly Gly Thr His Pro Glu Leu
        115                 120                 125

Leu Val Ala His Ala Tyr Thr Arg Tyr Leu Gly Asp Leu Ser Gly Gly
    130                 135                 140

Gln Val Leu Lys Lys Ile Ala Gln Lys Ala Met Ala Leu Pro Ser Ser
145                 150                 155                 160

Gly Glu Gly Leu Ala Phe Phe Thr Phe Pro Ser Ile Asp Asn Pro Thr
                165                 170                 175

Lys Phe Lys Gln Leu Tyr Arg Ala Arg Met Asn Thr Leu Glu Met Thr
            180                 185                 190

Pro Glu Val Lys His Arg Val Thr Glu Glu Ala Lys Thr Ala Phe Leu
        195                 200                 205

Leu Asn Ile Glu Leu Phe Glu Glu Leu Gln Ala Leu Leu Thr Glu Glu
    210                 215                 220

His Lys Asp Gln Ser Pro Ser Gln Thr Glu Phe Leu Arg Gln Arg Pro
225                 230                 235                 240

Ala Ser Leu Val Gln Asp Thr Thr Ser Ala Glu Thr Pro Arg Gly Lys
                245                 250                 255

Ser Gln Ile Ser Thr Ser Ser Ser Gln Thr Pro Leu Leu Arg Trp Val
```

```
                    260                 265                 270
Leu Thr Leu Ser Phe Leu Leu Ala Thr Val Ala Val Gly Ile Tyr Ala
                275                 280                 285
Met

<210> SEQ ID NO 23
<211> LENGTH: 283
<212> TYPE: PRT
<213> ORGANISM: Arabidopsis thaliana

<400> SEQUENCE: 23

Met Ala Thr Ser Arg Leu Asn Ala Ser Cys Arg Phe Pro Ala Ser Arg
1               5                   10                  15

Arg Leu Asp Cys Glu Ser Tyr Val Ser Leu Arg Ala Lys Thr Val Thr
                20                  25                  30

Ile Arg Tyr Val Arg Thr Ile Ala Ala Pro Arg Arg His Leu Val Arg
            35                  40                  45

Arg Ala Asn Glu Asp Gln Thr Leu Val Val Asn Val Ala Ala Ala
        50                  55                  60

Gly Glu Lys Pro Glu Arg Arg Tyr Pro Arg Glu Pro Asn Gly Phe Val
65                  70                  75                  80

Glu Glu Met Arg Phe Val Val Met Lys Ile His Pro Arg Asp Gln Val
                85                  90                  95

Lys Glu Gly Lys Ser Asp Ser Asn Asp Leu Val Ser Thr Trp Asn Phe
            100                 105                 110

Thr Ile Glu Gly Tyr Leu Lys Phe Leu Val Asp Ser Lys Leu Val Phe
        115                 120                 125

Glu Thr Leu Glu Arg Ile Ile Asn Glu Ser Ala Ile Gln Ala Tyr Ala
130                 135                 140

Gly Leu Lys Asn Thr Gly Leu Glu Arg Ala Glu Asn Leu Ser Arg Asp
145                 150                 155                 160

Leu Glu Trp Phe Lys Glu Gln Gly Tyr Glu Ile Pro Glu Ser Met Val
                165                 170                 175

Pro Gly Lys Ala Tyr Ser Gln Tyr Leu Lys Asn Ile Ala Glu Lys Asp
            180                 185                 190

Pro Pro Ala Phe Ile Cys His Phe Tyr Asn Ile Asn Phe Ala His Ser
        195                 200                 205

Ala Gly Gly Arg Met Ile Gly Thr Lys Val Ala Glu Lys Ile Leu Asp
210                 215                 220

Asn Lys Glu Leu Glu Phe Tyr Lys Trp Asp Gly Gln Leu Ser Glu Leu
225                 230                 235                 240

Leu Gln Asn Val Ser Glu Glu Leu Asn Lys Val Ala Glu Leu Trp Thr
                245                 250                 255

Arg Glu Glu Lys Asn His Cys Leu Glu Glu Thr Glu Lys Ser Phe Lys
            260                 265                 270

Phe Tyr Trp Glu Ile Phe Arg Tyr Leu Leu Ser
        275                 280

<210> SEQ ID NO 24
<211> LENGTH: 285
<212> TYPE: PRT
<213> ORGANISM: Arabidopsis thaliana

<400> SEQUENCE: 24

Met Ala Thr Thr Arg Leu Asn Pro Ser Cys His Phe Pro Ala Ser Thr
1               5                   10                  15
```

```
Arg Leu Ser Cys Glu Ser Tyr Leu Gly Leu Arg Thr Thr Gly Arg Ile
         20                  25                  30

Ser Tyr Ala Arg Thr Leu Thr Ala Pro Arg Gly Tyr Leu Ala Val Lys
             35                  40                  45

Ala Asn Gly Gly Gln Ala Ser Val Val Thr Ala Ala Ile Thr Glu
 50                  55                  60

Lys Gln Gln Lys Lys Tyr Pro Gly Glu Ser Lys Gly Phe Val Glu Glu
 65                  70                  75                  80

Met Arg Phe Val Ala Met Arg Leu His Thr Lys Asp Gln Ala Arg Glu
                 85                  90                  95

Gly Glu Lys Glu Ser Arg Ser Pro Glu Glu Gly Pro Val Ala Lys Trp
            100                 105                 110

Glu Pro Thr Val Glu Gly Tyr Leu His Phe Leu Val Asp Ser Lys Leu
            115                 120                 125

Val Tyr Asp Thr Leu Glu Gly Ile Ile Asp Gly Ser Asn Phe Pro Thr
130                 135                 140

Tyr Ala Gly Phe Lys Asn Thr Gly Leu Glu Arg Ala Glu Ser Leu Arg
145                 150                 155                 160

Lys Asp Leu Glu Trp Phe Lys Glu Gln Gly Tyr Glu Ile Pro Glu Pro
                165                 170                 175

Met Ala Pro Gly Lys Thr Tyr Ser Glu Tyr Leu Lys Asp Leu Ala Glu
            180                 185                 190

Asn Asp Pro Gln Ala Phe Ile Cys His Phe Tyr Asn Ile Tyr Phe Ala
            195                 200                 205

His Ser Ala Gly Gly Gln Met Ile Gly Thr Lys Val Ser Lys Lys Ile
    210                 215                 220

Leu Asp Asn Lys Glu Leu Glu Phe Tyr Lys Trp Asp Gly Gln Leu Ser
225                 230                 235                 240

Gln Leu Leu Gln Asn Val Arg Gln Lys Leu Asn Lys Val Ala Glu Trp
                245                 250                 255

Trp Thr Arg Glu Glu Lys Ser His Cys Leu Glu Glu Thr Glu Lys Ser
            260                 265                 270

Phe Lys Phe Ser Gly Glu Ile Leu Arg Leu Ile Leu Ser
            275                 280                 285

<210> SEQ ID NO 25
<211> LENGTH: 296
<212> TYPE: PRT
<213> ORGANISM: Gallus gallus

<400> SEQUENCE: 25

Met Glu Thr Ser Gln Pro His Asn Ala Glu Ser Met Ser Gln Asp Leu
1               5                  10                  15

Ser Glu Leu Leu Lys Glu Ala Thr Lys Glu Val His Glu Gln Ala Glu
            20                  25                  30

Asn Thr Pro Phe Met Lys Asn Phe Gln Lys Gly Gln Val Ser Leu His
            35                  40                  45

Glu Phe Lys Leu Val Thr Ala Ser Leu Tyr Phe Ile Tyr Ser Ala Leu
 50                  55                  60

Glu Glu Glu Ile Glu Arg Asn Lys Asp Asn Pro Val Tyr Ala Pro Val
 65                  70                  75                  80

Tyr Phe Pro Met Glu Leu His Arg Lys Ala Leu Glu Lys Asp Leu
                 85                  90                  95

Glu Tyr Phe Tyr Gly Ser Asn Thr Arg Ala Glu Ile Pro Cys Pro Glu
            100                 105                 110
```

```
Ala Thr Gln Lys Tyr Val Glu Arg Leu His Val Val Gly Lys Lys His
        115                 120                 125

Pro Glu Leu Leu Val Ala His Ala Tyr Thr Arg Tyr Leu Gly Asp Leu
    130                 135                 140

Ser Gly Gly Gln Val Leu Lys Lys Ile Ala Gln Lys Ala Leu Gln Leu
145                 150                 155                 160

Pro Ser Thr Gly Glu Gly Leu Ala Phe Phe Thr Phe Asp Gly Val Ser
                165                 170                 175

Asn Ala Thr Lys Phe Lys Gln Leu Tyr Arg Ser Arg Met Asn Ala Leu
                180                 185                 190

Glu Met Asp His Ala Thr Lys Lys Arg Val Leu Glu Glu Ala Lys Lys
            195                 200                 205

Ala Phe Leu Leu Asn Ile Gln Val Phe Glu Ala Leu Gln Lys Leu Val
        210                 215                 220

Ser Lys Ser Gln Glu Asn Gly His Ala Val Gln Pro Lys Ala Glu Leu
225                 230                 235                 240

Arg Thr Arg Ser Val Asn Lys Ser His Glu Asn Ser Pro Ala Ala Gly
                245                 250                 255

Lys Glu Ser Glu Arg Thr Ser Arg Met Gln Ala Asp Met Leu Thr Thr
            260                 265                 270

Ser Pro Leu Val Arg Trp Leu Leu Ala Leu Gly Phe Ile Ala Thr Thr
        275                 280                 285

Val Ala Val Gly Leu Phe Ala Met
        290                 295

<210> SEQ ID NO 26
<211> LENGTH: 272
<212> TYPE: PRT
<213> ORGANISM: Danio rerio

<400> SEQUENCE: 26

Met Asp Ser Thr Lys Ser Lys Ala Ala Glu Asn Thr Gly Ser Asp Leu
1               5                   10                  15

Ser Glu Gln Ile Lys Ala Val Thr Lys Asp Ser His Val Arg Ala Glu
            20                  25                  30

Asn Thr Gln Leu Met Leu Ser Tyr Gln Lys Gly Gln Ile Thr Gln Thr
        35                  40                  45

Gln Tyr Lys Leu Leu Leu Cys Ser Leu Tyr Glu Ile Tyr Arg Ala Leu
    50                  55                  60

Glu Glu Glu Leu Asp Arg Asn Ala Asp His Pro Ala Val Gln Pro Ile
65                  70                  75                  80

Tyr Phe Pro Gln Glu Leu Ala Arg Leu Glu Ala Leu Gly Gln Asp Leu
                85                  90                  95

Glu His Phe Phe Gly Pro Gln Trp Arg Lys Arg Ile Thr Val Pro Ala
            100                 105                 110

Ala Thr His Arg Tyr Ala Gln Arg Leu Arg Glu Ile Gly Lys Ser Ser
        115                 120                 125

Pro Glu Leu Leu Val Ala His Ala Tyr Thr Arg Tyr Leu Gly Asp Leu
    130                 135                 140

Ser Gly Gly Gln Val Leu Gly Lys Ile Thr Gln Lys Ser Leu Gly Leu
145                 150                 155                 160

Thr Gly Asn Lys Gly Ile Leu Phe Phe Ser Phe Pro Gly Val Thr Ser
                165                 170                 175

Ala Asn Arg Phe Lys Gln Leu Tyr Arg Ser Arg Met Asn Ser Ile Glu
                180                 185                 190
```

```
Phe Thr Glu Gln Lys Arg Gln Glu Ala Leu Asp Glu Ala Val Arg Ala
            195                 200                 205

Phe Glu Phe Asn Ile Asp Val Phe Asp Asp Leu Gln Lys Met Leu Ser
    210                 215                 220

Ile Thr Glu Glu Ala Ser Ser Asp Lys Gly Asn Glu Ala Ala Ser Gln
225                 230                 235                 240

Ser Leu Ser Lys Thr Phe Ser Ser Pro Ala Leu Gln Phe Ala Leu
            245                 250                 255

Gly Val Gly Ile Thr Leu Ala Thr Val Gly Met Gly Val Tyr Ala Phe
            260                 265                 270
```

<210> SEQ ID NO 27
<211> LENGTH: 288
<212> TYPE: PRT
<213> ORGANISM: Pan troglodytes

<400> SEQUENCE: 27

```
Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
    50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
        115                 120                 125

Leu Val Ala His Ala Tyr Thr Arg Tyr Leu Gly Asp Leu Ser Gly Gly
    130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
        195                 200                 205

Leu Asn Ile Gln Leu Phe Glu Glu Leu Gln Glu Leu Leu Thr His Asp
    210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Arg Ser Gln Ala Pro Leu Leu Arg Trp Val Leu
            260                 265                 270

Thr Leu Ser Phe Leu Val Ala Thr Val Ala Val Gly Leu Tyr Ala Met
        275                 280                 285
```

<210> SEQ ID NO 28
<211> LENGTH: 338

<212> TYPE: PRT
<213> ORGANISM: Canis lupus

<400> SEQUENCE: 28

```
Met Glu Arg Pro Gln Pro Asp Arg Gln Ala Pro Gly Ala Gly Arg Gly
1               5                   10                  15
Ala Arg Gly Ala Gly Arg Gly Val Arg Ala Leu Ser Pro Gly Trp Ala
            20                  25                  30
Ala Pro Ala Arg Arg Arg Glu Ala Pro Ser Pro Ser Phe Gly Phe
        35                  40                  45
Gly Leu Arg Gly Gly Arg Val Ser Val Cys Met Pro Gln Asp Leu Ser
    50                  55                  60
Glu Ala Leu Lys Glu Ala Thr Lys Glu Val His Thr Gln Ala Glu Asn
65                  70                  75                  80
Ala Glu Phe Met Lys Asn Phe Gln Lys Gly Gln Val Thr Arg Lys Gly
                85                  90                  95
Phe Lys Leu Val Met Ala Ser Leu Tyr His Val Tyr Glu Ala Leu Glu
            100                 105                 110
Glu Glu Ile Glu His Asn Arg Glu Asn Pro Val Tyr Ala Pro Leu Tyr
        115                 120                 125
Phe Pro Glu Glu Leu His Arg Lys Ala Ala Leu Glu Arg Asp Met Ala
    130                 135                 140
Phe Trp Tyr Gly Pro Arg Trp His Glu Ala Ile Pro Tyr Thr Gln Ala
145                 150                 155                 160
Thr Arg Arg Tyr Val Gln Arg Leu Gln Glu Val Gly Arg Arg Glu Pro
                165                 170                 175
Glu Leu Leu Val Ala His Ala Tyr Thr Arg Tyr Leu Gly Asp Leu Ser
            180                 185                 190
Gly Gly Gln Val Leu Lys Lys Ile Ala Gln Lys Ala Leu Asp Leu Pro
        195                 200                 205
Ser Ser Gly Glu Gly Val Asp Phe Phe Thr Phe Pro Asn Ile Ala Ser
    210                 215                 220
Ala Thr Lys Phe Lys Gln Leu Tyr Arg Ser Arg Met Asn Ser Leu Glu
225                 230                 235                 240
Met Thr Pro Glu Val Arg Gln Arg Val Ile Glu Glu Ala Lys Thr Ala
                245                 250                 255
Phe Leu Leu Asn Ile Gln Leu Phe Glu Glu Leu Gln Glu Leu Leu Ser
            260                 265                 270
Lys Asp Thr Glu Asp Gln Ser Pro Ser Gln Ala Ser Gly Leu Arg Gln
        275                 280                 285
Arg Val Gly Ser Arg Ala Gln Asp Ser Thr Pro Ala Glu Thr Pro Arg
    290                 295                 300
Gly Lys Pro Gln Leu Asn Leu Pro Ser Gln Ala Pro Leu Leu Arg Trp
305                 310                 315                 320
Val Leu Thr Leu Ser Phe Leu Val Ala Thr Val Ala Val Gly Leu Tyr
                325                 330                 335
Val Met
```

<210> SEQ ID NO 29
<211> LENGTH: 405
<212> TYPE: PRT
<213> ORGANISM: Hyphomonas neptunium ATCC 15444

<400> SEQUENCE: 29

```
Met Gln His Leu Lys Ala Phe Glu Asp Ala Leu Gly Ala Ile His Ser
1               5                   10                  15
```

Glu Gly Arg Tyr Arg Val Phe Ile Asp Leu His Arg His Lys Gly Arg
                20                  25                  30

Phe Pro Lys Ala Thr Ala Arg Phe Glu Ala Gly Glu Arg Glu Val Thr
            35                  40                  45

Ile Trp Cys Ser Asn Asp Tyr Leu Gly Met Gly Gln Asp Asp Asp Val
    50                  55                  60

Ile Lys Ser Met His Glu Ala Ile Asp Ser Phe Gly Ala Gly Ser Gly
65                  70                  75                  80

Gly Thr Arg Asn Ile Ser Gly Thr Thr Arg Phe His Val Asp Leu Glu
                85                  90                  95

Gln Glu Leu Ala Asp Leu His Arg Lys Glu Ala Ala Leu Leu Phe Thr
            100                 105                 110

Ser Gly Tyr Val Ser Asn Glu Ala Thr Leu Ser Thr Leu Gly Lys Ile
        115                 120                 125

Leu Pro Asn Leu Ile Ile Tyr Ser Asp Ala Leu Asn His Ala Ser Met
130                 135                 140

Ile Glu Gly Ile Arg Arg Ser Gly Ala Glu Tyr Arg Val Phe Arg His
145                 150                 155                 160

Asn Asp Val Asp His Leu Arg Ala Leu Leu Glu Leu Asp Asp Ala Asp
                165                 170                 175

Arg Pro Lys Leu Ile Ala Phe Glu Ser Val Tyr Ser Met Asp Gly Asp
            180                 185                 190

Phe Gly Arg Met Glu Glu Ile Cys Asp Leu Ala Gln Glu Phe Asn Ala
        195                 200                 205

Ile Thr Tyr Leu Asp Glu Val His Ala Val Gly Met Tyr Gly Glu Gln
210                 215                 220

Gly Ala Gly Val Ala Glu Met Leu Gly Leu Ala Asp Arg Ile Asp Ile
225                 230                 235                 240

Met Glu Gly Thr Leu Ala Lys Ala Tyr Gly Val Met Gly Gly Tyr Ile
                245                 250                 255

Ala Ser His Ser Ser Val Ile Asp Ala Ile Arg Ser Met Ala Ser Gly
            260                 265                 270

Phe Ile Phe Thr Thr Ser Thr Cys Pro Val Met Ala Ala Gly Ala Leu
        275                 280                 285

Ala Ser Ile Arg Lys Leu Arg Ala Asp Glu Gly Arg Arg Leu Arg Ala
290                 295                 300

Ile His Gln Asp Lys Ala Ala Thr Leu Lys Gln Lys Phe Arg Asp Ala
305                 310                 315                 320

Gly Leu Pro Val Met Glu Ser Pro Ser His Ile Val Pro Leu Leu Val
                325                 330                 335

Gly Asp Pro Glu Arg Cys Lys Ala Leu Ser Asp Thr Leu Leu Phe Asp
            340                 345                 350

Phe Gly Ile Tyr Val Gln Pro Ile Asn Tyr Pro Thr Val Pro Arg Gly
        355                 360                 365

Thr Glu Arg Leu Arg Phe Thr Pro Ser Pro Val His Asp Glu Val Met
370                 375                 380

Met Asp Glu Leu Val Ala Ala Ile Leu Ala Val Trp Lys Gln Leu Gly
385                 390                 395                 400

Leu Asp Lys Ala Ala
            405

<210> SEQ ID NO 30
<211> LENGTH: 403
<212> TYPE: PRT

```
<213> ORGANISM: Orientia tsutsugamushi str. Boryong

<400> SEQUENCE: 30

Met Leu Ser Tyr Asn Asn Phe Phe Asp Asn His Leu His Ser Ile Lys
1               5                   10                  15

Leu Glu Gly Arg Tyr Arg Lys Phe Thr Cys Ile Lys Lys Ser Thr Lys
            20                  25                  30

Trp Phe Pro Tyr Asn Ile Cys Ala Gln Thr Gly Lys Lys Val Leu Ile
        35                  40                  45

Trp Cys Thr Asn Asp Tyr Leu Gly Met Ser Phe His Pro Glu Val Leu
    50                  55                  60

Ser Ser Ala Val Leu Ala Val Lys Gln Met Gly Val Gly Ser Gly Gly
65                  70                  75                  80

Thr Arg Asn Ile Gly Gly Asn Asn Ser Ala Ile Val Glu Leu Glu Glu
                85                  90                  95

Leu Leu Ala Ile Leu His Lys Lys Gln Lys Ala Leu Val Phe Thr Ser
            100                 105                 110

Gly Tyr Val Ala Asn Asp Thr Thr Leu Gln Thr Leu Ala Lys Ile Ile
        115                 120                 125

Pro Gly Leu Val Phe Ile Ser Asp Glu Tyr Asn His Ala Ser Ile Ile
    130                 135                 140

Ala Gly Ile Arg Asn Ser Arg Ala Glu Lys His Ile Tyr Phe His Asn
145                 150                 155                 160

Asn Met Gln Ser Leu Gln Gln Ile Leu Ser Ser Ile Pro Ile Asn Gln
                165                 170                 175

Pro Lys Ile Ile Val Phe Glu Ala Ile Tyr Ser Met Ser Gly Thr Ile
            180                 185                 190

Ala Ala Val Lys Glu Ile Cys Asn Leu Ala Lys Met Tyr Asn Ala Leu
        195                 200                 205

Thr Tyr Ile Asp Glu Val His Ser Val Gly Leu Tyr Gly Asp Asp Gly
    210                 215                 220

Ser Gly Ile Cys Thr Leu Thr Gly Leu Phe Asn Gln Val Asp Ile Ile
225                 230                 235                 240

Gln Gly Asn Leu Ala Lys Ala Tyr Gly Ala Ile Gly Gly Tyr Ile Ala
                245                 250                 255

Ala Asn Ser Asn Ile Ile Asp Ala Ile Arg Ser Thr Ala Ser Gly Phe
            260                 265                 270

Ile Phe Thr Thr Ala Leu Pro Pro Val Ile Ser Cys Ala Ala Met Thr
        275                 280                 285

Ser Ile Lys Tyr Leu Met Lys Ser Asn Lys Glu Arg Leu Lys Leu Gln
    290                 295                 300

Glu Thr Val Ala Lys Leu Lys Asp Ser Leu Thr Ser Ala Gly Ile Arg
305                 310                 315                 320

Tyr Leu Thr Asn Asn Ser His Ile Ile Ala Ile Val Ile Gly Glu Pro
                325                 330                 335

Val Leu Thr Gln Arg Val Ala Gln Ile Leu Leu Glu Glu Tyr Asn Ile
            340                 345                 350

Tyr Ile Gln Ala Ile Asn Phe Pro Thr Val Pro Arg Gly Thr Glu Arg
        355                 360                 365

Leu Arg Ile Thr Pro Thr Pro Phe His Thr Asp Gly Met Ile His Asn
    370                 375                 380

Leu Thr Val Ala Leu Lys Gln Ile Leu Leu Asn Leu Asn Ile Tyr Ala
385                 390                 395                 400

Ala Leu Arg
```

<210> SEQ ID NO 31
<211> LENGTH: 425
<212> TYPE: PRT
<213> ORGANISM: Azorhizobium caulinodans

<400> SEQUENCE: 31

```
Met Ser Tyr Asp His Phe Phe Ala Asp Ala Val Asp Ala Leu Arg Arg
1               5                   10                  15

Glu Arg Arg Tyr Arg Thr Phe Ala Asp Val Glu Arg Asp Ala Thr Arg
            20                  25                  30

Phe Pro Arg Ala Thr Trp His Ser Pro Gly Gly Pro Arg Glu Ile Val
        35                  40                  45

Val Trp Cys Ser Asn Asp Tyr Leu Gly Met Gly Ser His Pro Ala Val
    50                  55                  60

Val Glu Ala Met Arg Glu Thr Ala Leu Arg Arg Gly Ala Gly Ala Gly
65                  70                  75                  80

Gly Thr Arg Asn Ile Ser Gly Asn Ser His Glu Ile Val Leu Leu Glu
                85                  90                  95

Arg Glu Leu Ala Asp Leu His Gly Lys Glu Gln Gly Leu Val Phe Thr
            100                 105                 110

Ser Gly Tyr Val Ser Asn Ala Thr Gly Ile Ser Thr Ile Ala Lys Leu
        115                 120                 125

Ile Pro Asp Cys Val Val Ile Ser Asp Glu Leu Asn His Asn Ser Met
130                 135                 140

Ile Glu Gly Val Arg Gln Gly Gly Arg Gln Lys Phe Ile Phe Arg His
145                 150                 155                 160

Asn Asp Leu Ala His Leu Glu Glu Ile Leu Gln Ala Val Ala Asp Arg
                165                 170                 175

Pro Lys Leu Ile Val Phe Glu Ser Val Tyr Ser Met Asp Gly Asp Ile
            180                 185                 190

Ala Pro Met Ala Ala Ile Cys Asp Leu Ala Glu Arg Tyr Gly Ala Met
        195                 200                 205

Thr Tyr Leu Asp Glu Val His Ala Val Gly Met Tyr Gly Pro Arg Gly
    210                 215                 220

Gly Gly Val Ala Glu Arg Asp Gly Val Met Asp Arg Ile Asp Val Ile
225                 230                 235                 240

Glu Gly Thr Leu Gly Lys Ala Phe Gly Val Val Gly Gly Tyr Leu Thr
                245                 250                 255

Gly Lys Arg Val Val Met Asp Ala Val Arg Ser Tyr Ala Pro Gly Phe
            260                 265                 270

Ile Phe Thr Thr Ala Leu Pro Pro Ala Val Ala Ala Ala Ala Thr Ala
        275                 280                 285

Ser Ile Arg His Leu Lys Ala Ser Asn Ala Gly Arg Asp Gly Gln Arg
    290                 295                 300

Arg Gln Val Ala Lys Val Lys Ala Ala Leu Ala Ala Ala Gly Leu Pro
305                 310                 315                 320

Gln Met Glu Thr Pro Thr His Ile Val Pro Val Met Val Gly Asp Ala
                325                 330                 335

Lys Ala Cys Lys Ala Ala Ser Asp Val Leu Leu Asn Glu His Asn Ile
            340                 345                 350

Tyr Ile Gln Pro Ile Asn Tyr Pro Thr Val Pro Arg Gly Thr Glu Arg
        355                 360                 365

Leu Arg Ile Thr Pro Thr Pro Phe His Asn Asp Lys Leu Ile Ala His
    370                 375                 380
```

```
Leu Ala Asp Ala Leu Asn Asp Val Trp Asn Arg Leu Asp Leu Pro Arg
385                 390                 395                 400

Val Arg Asp Thr Gly Ser Glu Arg Arg Leu Val Ala Ala Gly Ala Ala
            405                 410                 415

Ser Leu Ala Met Pro Thr Ala Gly Gly
            420                 425

<210> SEQ ID NO 32
<211> LENGTH: 408
<212> TYPE: PRT
<213> ORGANISM: Caulobacter crescentus

<400> SEQUENCE: 32

Met Asp Tyr Lys Ala Ala Phe Arg Ser Ala Val Glu Gln Ile Arg Glu
1               5                   10                  15

Glu Gly Arg Tyr Arg Val Phe Ala Asp Leu Lys Arg Gln Arg Gly Gln
            20                  25                  30

Phe Pro Arg Ala Thr Trp Thr Arg Gln Asp Gly Ser Glu His Glu Val
        35                  40                  45

Val Val Trp Cys Ser Asn Asp Tyr Leu Gly Gln Gly Gln Asn Pro Val
50                  55                  60

Val Leu Glu Ala Met Lys Ala Val Asp Glu His Gly Ser Gly Ser
65                  70                  75                  80

Gly Gly Thr Arg Asn Ile Ser Gly Thr Asn His Asp His Val Leu Leu
                85                  90                  95

Glu Gln Glu Leu Ala Asp Leu His Gly Lys Ala Gly Leu Leu Phe
            100                 105                 110

Thr Ser Gly Tyr Val Ser Asn Glu Ala Thr Leu Ser Val Val Gln Lys
        115                 120                 125

Ile Leu Pro Gly Leu Ile Ile Phe Ser Asp Glu Leu Asn His Ala Ser
130                 135                 140

Met Ile Ala Gly Ile Arg Asn Gly Gly Gly Pro Arg Lys Ile Phe Lys
145                 150                 155                 160

His Asn Asp Leu Ala His Leu Glu Gln Leu Leu Ala Glu Ala Pro Ala
                165                 170                 175

Asp Ala Pro Lys Leu Ile Ala Phe Glu Ser Val Tyr Ser Met Asp Gly
            180                 185                 190

Asp Ile Ala Asp Leu Ala Gly Thr Val Ala Leu Ala Lys Lys Tyr Gly
        195                 200                 205

Ala Met Thr Tyr Leu Asp Glu Val His Ala Val Gly Met Tyr Gly Pro
210                 215                 220

Arg Gly Gly Gly Val Ala Glu Arg Asp Gly Leu Met Gly Glu Ile Asp
225                 230                 235                 240

Ile Ile Glu Gly Thr Leu Gly Lys Ala Phe Gly Val Met Gly Gly Tyr
                245                 250                 255

Ile Thr Gly Asp Ala Glu Val Ile Asp Ala Ile Arg Leu Met Ala Ser
            260                 265                 270

Gly Phe Ile Phe Thr Thr Ser Leu Pro Pro Ala Leu Thr Ala Gly Ala
        275                 280                 285

Leu Ala Ser Val Arg Trp Leu Lys Gln His Pro Glu Val Arg Glu Ile
290                 295                 300

His Gln Glu Arg Ala Ala Thr Leu Lys Ala Met Phe Lys Ala Ala Gly
305                 310                 315                 320

Leu Pro Val Met Asp Ser Val Ser His Ile Val Pro Val Leu Val Gly
                325                 330                 335
```

-continued

```
Asp Pro Val His Cys Lys Met Ile Ser Asp Met Leu Leu Ala Asp Phe
            340                 345                 350

Gly Val Tyr Val Gln Pro Ile Asn Tyr Pro Thr Val Pro Arg Gly Thr
        355                 360                 365

Glu Arg Leu Arg Phe Thr Pro Thr Pro Phe His Thr Asp Asp Met Met
    370                 375                 380

Arg Lys Leu Val Ala Ala Met Glu Lys Leu Trp Ala His Cys Asn Val
385                 390                 395                 400

Ala Arg Met Gly Gly Tyr Ala Ala
                405

<210> SEQ ID NO 33
<211> LENGTH: 425
<212> TYPE: PRT
<213> ORGANISM: Brucella canis

<400> SEQUENCE: 33

Met Asp Tyr Arg Arg Phe Phe Glu Glu Ala Ile Asp Gln Leu His Ala
1               5                   10                  15

Glu Lys Arg Tyr Arg Val Phe Ala Asp Leu Glu Arg Ile Val Gly Arg
            20                  25                  30

Phe Pro Gln Ala Ile Trp Arg Asn Asn Gly Thr Ala Arg Glu Ile Thr
        35                  40                  45

Val Trp Cys Ser Asn Asp Tyr Leu Gly Met Gly His His Pro Asp Val
    50                  55                  60

Ile Lys Ala Met Cys Glu Thr Ala Gly Ser Ala Gly Ser Gly Ala Gly
65                  70                  75                  80

Gly Thr Arg Asn Ile Ser Gly Asn Asn His Pro Leu Val Glu Leu Glu
                85                  90                  95

Ser Glu Leu Ala Asp Leu His Gly Lys Glu Ala Gly Leu Val Phe Thr
            100                 105                 110

Ser Gly Phe Val Ser Asn Glu Ala Ser Ile Ser Thr Ile Ala Arg Leu
        115                 120                 125

Leu Pro Asn Cys Leu Ile Leu Ser Asp Glu Leu Asn His Ala Ser Met
    130                 135                 140

Ile Glu Gly Val Arg His Ser Gly Ala Glu Lys Lys Ile Phe Arg His
145                 150                 155                 160

Asn Asp Val Glu His Leu Glu Gln Leu Leu Lys Ala Ala Asp Arg Ser
                165                 170                 175

Arg Ala Lys Leu Ile Val Phe Glu Ser Val Tyr Ser Met Asp Gly Asp
            180                 185                 190

Ile Ala Pro Ile Glu Lys Ile Ala Asp Leu Ala Asp Lys Tyr Asn Ala
        195                 200                 205

Met Thr Tyr Ile Asp Glu Val His Ala Val Gly Met Tyr Gly Ala His
    210                 215                 220

Gly Gly Gly Ile Thr Glu Arg Asp Gly Leu Ala His Arg Ile Asp Ile
225                 230                 235                 240

Ile Glu Gly Thr Leu Ala Lys Ala Phe Gly Ala Leu Gly Gly Tyr Ile
                245                 250                 255

Thr Gly Ser Arg Ala Ile Ile Asp Ala Val Arg Ser Tyr Ala Pro Gly
            260                 265                 270

Phe Ile Phe Thr Thr Ser Leu Pro Pro Ala Val Ala Ala Ala Ala Thr
        275                 280                 285

Ala Ala Ile Arg His Leu Lys Ser Ser Gln Ala Glu Arg Asp Gly Gln
    290                 295                 300
```

```
Gln Arg Gln Ala Gln Arg Ala Lys Asp Val Leu Ser Ala Ala Gly Leu
305                 310                 315                 320

Pro Val Met Pro Ser Gln Thr His Ile Val Pro Ile Leu Val Gly Asp
                325                 330                 335

Pro Glu Leu Cys Lys Lys Ala Ser Asp Arg Leu Leu Glu Val His Gly
            340                 345                 350

Ile Tyr Ile Gln Pro Ile Asn Tyr Pro Thr Val Pro Arg Gly Thr Glu
        355                 360                 365

Arg Leu Arg Ile Thr Pro Ser Pro Leu His Asp Asp Lys Leu Ile Asp
    370                 375                 380

Gly Leu Lys Asp Ala Leu Leu Glu Ile Trp Asn Glu Leu Gly Ile Pro
385                 390                 395                 400

Phe Ala Glu Pro Ser Ala Pro Gln Ala Ala Asn Ser Asp Arg Ile Ile
                405                 410                 415

Pro Leu Met Val Ser Lys Ala Gly Gly
            420                 425

<210> SEQ ID NO 34
<211> LENGTH: 413
<212> TYPE: PRT
<213> ORGANISM: Bordetella petrii

<400> SEQUENCE: 34

Met Tyr Gln Thr Leu Leu Ser Lys Lys Leu Ser Asp Leu Lys Ala Ser
1               5                   10                  15

Gly Gln Tyr Arg Thr Phe Val Thr Leu Asn Arg Ile Cys Gly Gln Tyr
            20                  25                  30

Pro Leu Ala Gln Leu Glu Gly Gly Asp Glu Arg Pro Val Ile Val Trp
        35                  40                  45

Cys Ser Asn Asp Tyr Leu Gly Met Ser Gln His Leu Val Val Arg Gln
    50                  55                  60

Ala Met His Asp Ala Ile Asp Arg Tyr Gly Ala Gly Ser Gly Gly Ser
65                  70                  75                  80

Arg Asn Ile Gly Gly Ser His Gly Ile Phe Ser Gln Leu Glu Arg Ser
                85                  90                  95

Leu Ala Asp Trp His Ser Lys Glu Ala Ala Leu Val Phe Pro Thr Gly
            100                 105                 110

Phe Ser Ser Asn Asp Ala Thr Leu Gln Cys Leu Leu Arg Glu Ile Pro
        115                 120                 125

Asp Cys Val Val Ile Ser Asp Glu Lys Asn His Ala Ser Ile Ile Asn
    130                 135                 140

Gly Ile Arg Ala Thr Ser Thr Glu Arg Gln Val Phe Arg His Asn Asp
145                 150                 155                 160

Leu Asp His Leu Glu Glu Ser Leu Ala Arg Tyr Pro Leu Glu Arg Pro
                165                 170                 175

Lys Ile Val Val Phe Glu Ser Val Tyr Ser Met Asp Gly Asp Ile Ser
            180                 185                 190

Pro Met Ala Glu Ile Val Asp Ile Ala Lys Gln Tyr Asn Ala Leu Thr
        195                 200                 205

Tyr Leu Asp Glu Val His Ala Val Gly Met Tyr Gly Pro Arg Gly Ala
    210                 215                 220

Gly Leu Ala Ala Gln Leu Gly Ile Ala Asp Lys Val Asp Ile Ile Gln
225                 230                 235                 240

Gly Thr Met Ala Lys Ala Ile Gly Val Ile Gly Gly Tyr Ile Thr Gly
                245                 250                 255
```

Ala Gln Trp Leu Ile Asp Ala Val Arg Ser Phe Ser Thr Gly Phe Ile
            260                 265                 270

Phe Thr Thr Ser Leu Pro Pro Val Val Ala Ala Gly Cys Leu Ala Ser
        275                 280                 285

Ile Glu His Leu Lys Thr Gln Ser Gln Glu Arg Glu Leu Leu His Thr
    290                 295                 300

Lys Thr Gln Gln Leu Arg Gln Ala Leu Asp Ser Leu Asp Ile Pro Val
305                 310                 315                 320

Met Ser Cys Ser Ser Thr His Val Leu Pro Val Leu Val Gly Asp Ala
                325                 330                 335

Ile Lys Cys Lys Glu Ala Ala Glu Arg Leu Leu Ser Val His Gly Val
            340                 345                 350

Tyr Leu Gln Pro Ile Asn Phe Pro Ser Val Ala Ala Gly Thr Glu Arg
        355                 360                 365

Phe Arg Val Asn Val Thr Pro Asn His Thr Asp Glu Gln Val Thr His
    370                 375                 380

Leu Ala Glu Ala Leu Arg Glu Val Phe Glu His Phe Asp Ile Pro Leu
385                 390                 395                 400

Lys Thr Pro Pro Ala Phe Ala Ser Ala Arg Glu Ala Ser
                405                 410

<210> SEQ ID NO 35
<211> LENGTH: 408
<212> TYPE: PRT
<213> ORGANISM: Caulobacter sp. K31

<400> SEQUENCE: 35

Met Asp Tyr Lys Ala Ala Phe Arg Asn Thr Val Asp Gln Ile Arg Asp
1               5                   10                  15

Glu Gly Arg Tyr Arg Val Phe Ala Asp Val Lys Arg His Arg Gly Ala
            20                  25                  30

Phe Pro Arg Ala Thr Trp Thr Arg Pro Asp Gly Gly Glu Ser Glu Ile
        35                  40                  45

Val Val Trp Cys Ser Asn Asp Tyr Leu Gly Gln Gly Gln Asn Pro Leu
    50                  55                  60

Val Leu Asp Ala Met His Ala Ala Ile Asp Gln His Gly Ser Gly Ser
65                  70                  75                  80

Gly Gly Thr Arg Asn Ile Ser Gly Thr Asn His His Val Glu Leu
                85                  90                  95

Glu Ala Glu Leu Ala Asp Leu His Gly Lys Glu Ala Ala Leu Leu Phe
            100                 105                 110

Thr Ser Gly Tyr Val Ser Asn Glu Ala Ser Leu Ser Ala Leu Gln Lys
        115                 120                 125

Ile Leu Pro Gly Leu Ile Ile Phe Ser Asp Ala Gln Asn His Ala Ser
    130                 135                 140

Met Ile Ala Gly Ile Arg Asn Gly Gly Cys Gln Arg His Val Phe Arg
145                 150                 155                 160

His Asn Asp Leu Ala His Leu Glu Glu Leu Ile Ala Ala Pro Ala
                165                 170                 175

Asp Ala Pro Lys Leu Ile Ala Phe Glu Ser Val Tyr Ser Met Asp Gly
            180                 185                 190

Asp Ile Ala Asp Leu Ala Gly Thr Val Ala Leu Ala Lys Lys Tyr Gly
        195                 200                 205

Ala Met Thr Tyr Leu Asp Glu Val His Ala Val Gly Met Tyr Gly Pro
    210                 215                 220

```
Arg Gly Gly Gly Val Ala Glu Arg Asp Arg Leu Met Asp Gln Ile Asp
225                 230                 235                 240

Ile Ile Glu Gly Thr Leu Gly Lys Ala Phe Gly Val Met Gly Gly Tyr
            245                 250                 255

Ile Thr Gly Asp Ala Val Val Asp Ala Ile Arg Leu Met Ala Ser
                260                 265                 270

Gly Phe Ile Phe Thr Thr Ser Leu Pro Pro Ala Leu Thr Ala Gly Ala
            275                 280                 285

Leu Ala Ser Val Lys Tyr Leu Lys His His Pro Glu Val Arg Glu Ala
            290                 295                 300

His Gln Glu Arg Ala Gln Thr Leu Lys Ala Met Phe Lys Ala Ala Gly
305                 310                 315                 320

Leu Pro Val Met Glu Asn Asp Ser His Ile Val Pro Val Leu Val Gly
                325                 330                 335

Asp Pro Val His Cys Lys Leu Ile Ser Asp Met Leu Leu Ala Asp His
                340                 345                 350

Gly Val Tyr Val Gln Pro Ile Asn Tyr Pro Thr Val Pro Arg Gly Thr
            355                 360                 365

Glu Arg Leu Arg Phe Thr Pro Thr Pro Phe His Thr Asp Asp Met Met
370                 375                 380

Arg Lys Leu Val Gly Ala Met Glu Thr Leu Trp Ala His Cys Asn Val
385                 390                 395                 400

Ala Arg Met Gly Gly Tyr Ala Ala
                405

<210> SEQ ID NO 36
<211> LENGTH: 411
<212> TYPE: PRT
<213> ORGANISM: Streptomyces griseus

<400> SEQUENCE: 36

Met Ile Ser Thr Leu Ala Pro Pro Ala Asp Ala Thr Ser Thr Ala
1               5                   10                  15

Asp Thr Tyr Ala Gly Leu Arg Ala Gly Leu Asp Lys Leu Arg Ala Asp
                20                  25                  30

Gly Leu Tyr Arg Asp Phe Val Ala Cys Ser Tyr Leu Ala Glu Asp Arg
            35                  40                  45

Gly His Ala Leu His Gln Gly Arg Arg Ile Gln Val Trp Cys Thr Asn
    50                  55                  60

Asp Tyr Leu Gly Met Ser Gln His Pro Asp Val Met Arg Ala Gln Ile
65                  70                  75                  80

Ala Ser Thr Leu Arg His Gly Thr Gly Asn Gly Gly Ser Arg Asn Ile
                85                  90                  95

Ala Gly Thr Ser Glu Ala His Val Glu Leu Glu Thr Leu Leu Ala Gly
            100                 105                 110

Trp His Ala Lys Glu Arg Ala Leu Val Phe Asn Ser Gly Tyr Val Ala
        115                 120                 125

Asn Val Glu Thr Leu Thr Thr Leu Leu Arg Ala Glu Pro Arg Thr Met
    130                 135                 140

Val Phe Ser Asp Ala Leu Asn His Arg Ser Leu Ile Glu Gly Val Arg
145                 150                 155                 160

Thr Ser Gly Asn Asp Lys Tyr Val Phe Ala His Asn Asp Leu Thr Asp
                165                 170                 175

Leu Glu Leu Ala Leu Ala Ala Gln Pro Leu Asp Arg Pro Lys Leu Ile
            180                 185                 190
```

```
Val Phe Glu Ser Val Tyr Ser Met Asp Gly Asp Val Ala Pro Ile Arg
        195                 200                 205

Glu Ile Cys Asp Leu Ala Glu Arg Tyr His Ala Gln Thr Tyr Leu Asp
    210                 215                 220

Glu Thr His Ala Ile Gly Val Leu Gly Pro Thr Gly Ala Gly Val Cys
225                 230                 235                 240

Glu Glu Ile Gly Glu Ser Arg Ala Thr Phe Val Gln Gly Val Phe Gly
                245                 250                 255

Lys Ala Val Gly Ala Thr Gly Gly Tyr Val Ala Gly Pro Asp Val Pro
            260                 265                 270

Leu Asp Tyr Thr Arg Ser His Ala Pro Gly Phe Ile Phe Thr Thr Thr
        275                 280                 285

Ile Pro Arg Ala Ser Leu Asp Ala Ala Leu Ala Ser Leu Ser Val Ile
    290                 295                 300

Arg Ser Pro Glu Gly Ala Gly Met Arg Glu Arg Leu His Ala Asn Ala
305                 310                 315                 320

Glu Leu Met Arg Arg Arg Leu Thr Glu Ala Gly Ile Ala His Val Pro
                325                 330                 335

Ala Pro Thr His Leu Val Pro Ile Leu Val Pro Gly Gly Asn Arg Val
            340                 345                 350

Lys Arg Val Ser Arg Arg Leu Leu Asp Glu His Ser Val Tyr Val Gln
        355                 360                 365

Pro Ile Asn Phe Pro Ser Val Pro Lys Gly Gly Glu Arg Phe Arg Val
    370                 375                 380

Thr Val Ala Pro Phe Arg Thr Glu Ala Gln Ile Glu Gly Phe Val Glu
385                 390                 395                 400

Ala Leu Ala Arg Cys Leu Ala Asp Asp Pro Ser
                405                 410

<210> SEQ ID NO 37
<211> LENGTH: 403
<212> TYPE: PRT
<213> ORGANISM: Orientia tsutsugamushi str. Ikeda

<400> SEQUENCE: 37

Met Val Ser Tyr Asn Asn Phe Phe Asp Asn His Leu His Ser Ile Lys
1               5                   10                  15

Leu Glu Gly Arg Tyr Arg Lys Phe Thr Cys Ile Lys Lys Ser Ala Lys
            20                  25                  30

Cys Phe Pro Tyr Asn Ile Cys Ala Gln Thr Gly Lys Lys Val Leu Ile
        35                  40                  45

Trp Cys Thr Asn Asp Tyr Leu Gly Met Ser Phe His Pro Glu Val Leu
    50                  55                  60

Ser Ser Ala Val Leu Ala Val Lys Gln Met Gly Val Gly Ala Gly Gly
65                  70                  75                  80

Thr Arg Asn Ile Gly Gly Asn Asn Ser Ala Ile Val Glu Leu Glu Glu
                85                  90                  95

Leu Leu Ala Ile Leu His Lys Lys Gln Lys Ala Leu Val Phe Thr Ser
            100                 105                 110

Gly Tyr Val Ala Asn Asp Thr Thr Leu Gln Thr Leu Ala Lys Ile Ile
        115                 120                 125

Pro Gly Leu Val Phe Ile Ser Asp Glu Tyr Asn His Ala Ser Ile Ile
    130                 135                 140

Ala Gly Ile Arg Asn Ser Arg Ala Glu Lys His Ile Tyr Phe His Asn
145                 150                 155                 160
```

Asn Met Gln Ser Leu Gln Gln Ile Leu Ser Ser Ile Pro Ile Asn Gln
            165                 170                 175

Pro Lys Ile Ile Val Phe Glu Ala Ile Tyr Ser Met Ser Gly Thr Ile
            180                 185                 190

Ala Asp Val Lys Gly Ile Cys Asn Leu Ala Lys Met Tyr Asn Ala Leu
            195                 200                 205

Thr Tyr Ile Asp Glu Val His Ser Val Gly Leu Tyr Gly Asp Asp Gly
210                 215                 220

Ser Gly Ile Cys Thr Leu Thr Gly Leu Phe Asn Gln Val Asp Ile Ile
225                 230                 235                 240

Gln Gly Asn Leu Ala Lys Ala Tyr Gly Ala Ile Gly Tyr Ile Ala
            245                 250                 255

Ala Asn Ser Asn Ile Ile Asp Ala Ile Arg Ser Thr Ala Ser Gly Phe
            260                 265                 270

Ile Phe Thr Thr Ala Leu Pro Pro Val Ile Ser Cys Ala Ala Met Thr
            275                 280                 285

Ser Ile Arg Tyr Leu Met Lys Ser Asn Lys Glu Arg Leu Lys Leu His
            290                 295                 300

Glu Thr Val Ser Lys Leu Lys Asp Ser Leu Ser Asn Ala Gly Ile Arg
305                 310                 315                 320

Tyr Leu Thr Asn Asn Ser His Ile Ile Ala Ile Val Ile Gly Glu Pro
            325                 330                 335

Val Leu Thr Gln Arg Leu Ala Gln Ile Leu Glu Glu Tyr Asn Ile
            340                 345                 350

Tyr Ile Gln Ala Ile Asn Phe Pro Thr Val Pro Arg Gly Thr Glu Arg
            355                 360                 365

Leu Arg Ile Thr Pro Thr Pro Phe His Thr Asp Glu Met Ile His Asn
            370                 375                 380

Leu Thr Val Ala Leu Lys Gln Val Leu Leu Asn Leu Asn Ile Ser Ala
385                 390                 395                 400

Ala Leu Gly

<210> SEQ ID NO 38
<211> LENGTH: 409
<212> TYPE: PRT
<213> ORGANISM: Phenylobacterium zucineum

<400> SEQUENCE: 38

Met Asp Tyr Arg Val Ala Phe Arg Thr Ala Leu Glu Asn Ile Arg Ser
1               5                   10                  15

Glu Gly Arg Tyr Arg Val Phe Ala Asp Leu Lys Arg His Arg Gly Ala
            20                  25                  30

Phe Pro Arg Ala Thr Trp Thr Arg Ala Asp Gly Ser Glu Ser Asp Val
            35                  40                  45

Val Val Trp Cys Ser Asn Asp Tyr Leu Gly Gln Gly Gln Asn Pro Val
            50                  55                  60

Val Leu Asp Ala Met His Arg Ala Ile Glu Ala Ala Gly Ala Gly Ser
65                  70                  75                  80

Gly Gly Thr Arg Asn Ile Ser Gly Thr Thr His Tyr His Val Glu Leu
            85                  90                  95

Glu Arg Glu Leu Ala Asp Leu His Gly Lys Glu Ala Ala Leu Leu Phe
            100                 105                 110

Thr Ser Gly Tyr Val Ser Asn Glu Ala Thr Leu Ser Thr Leu Tyr Lys
            115                 120                 125

```
Ile Leu Pro Gly Leu Val Val Phe Ser Asp Ala Leu Asn His Asn Ser
            130                 135                 140

Met Ile Ser Gly Ile Arg Ala Gly Lys Arg Glu Gln Arg His Val Phe
145                 150                 155                 160

Arg His Asn Asp Leu Ala His Leu Glu Glu Leu Leu Ala Ala Ala Asp
                165                 170                 175

Pro Ala Ala Pro Lys Leu Ile Ala Phe Glu Ser Val Tyr Ser Met Asp
                180                 185                 190

Gly Asp Ile Ala Asp Leu Pro Ala Met Val Ala Leu Ala Arg Lys Tyr
                195                 200                 205

Gly Ala Met Thr Tyr Leu Asp Glu Val His Ala Val Gly Met Tyr Gly
            210                 215                 220

Pro Arg Gly Ala Gly Val Ala Glu Arg Asp Gly Val Met Asp Gln Ile
225                 230                 235                 240

Asp Ile Val Glu Gly Thr Leu Gly Lys Ala Phe Gly Val Met Gly Gly
                245                 250                 255

Tyr Ile Ala Ala Asp Ala Val Ile Val Asp Ala Ile Arg Ser Tyr Ala
                260                 265                 270

Asp Gly Phe Ile Phe Thr Thr Ser Leu Pro Pro Ala Leu Ala Ala Gly
                275                 280                 285

Ala Ala Ala Ser Ile Arg Trp Leu Lys Glu His Asp Glu Val Arg Thr
290                 295                 300

Ala His Gln Glu Arg Ala Ala Thr Leu Lys Ala Lys Met Arg Ala Ala
305                 310                 315                 320

Gly Leu Pro Val Met Asp Ser Val Ser His Ile Val Pro Val Leu Val
                325                 330                 335

Gly Asp Pro Val His Cys Lys Met Ile Ser Asp Ile Leu Leu Glu Asp
                340                 345                 350

His Gly Ile Tyr Val Gln Pro Ile Asn Tyr Pro Thr Val Pro Arg Gly
                355                 360                 365

Thr Glu Arg Leu Arg Phe Thr Pro Ser Pro Ala His Thr Asp Ala Met
370                 375                 380

Met Asp Ala Leu Val Ala Ala Leu Glu Thr Leu Trp Val Arg Cys Asn
385                 390                 395                 400

Val Lys Arg Val Gly Gly Val Ala Ala
                405

<210> SEQ ID NO 39
<211> LENGTH: 409
<212> TYPE: PRT
<213> ORGANISM: Phenylobacterium zucineum HLK1

<400> SEQUENCE: 39

Met Asp Tyr Lys Thr Ala Phe Ala Ser Ala Leu Asp Arg Val Gln Ala
1               5                   10                  15

Glu Gly Arg Tyr Arg Val Phe Ala Asp Leu Lys Arg His Arg Gly Ala
                20                  25                  30

Phe Pro Arg Ala Thr Trp Thr Lys Ala Asp Gly Ser Glu Ser Asp Val
            35                  40                  45

Val Val Trp Cys Ser Asn Asp Tyr Leu Gly Gln Gly Gln Asn Pro Val
        50                  55                  60

Val Leu Asp Ala Met His Arg Ala Ile Glu Ala Ala Gly Ala Gly Ser
65              70                  75                  80

Gly Gly Thr Arg Asn Ile Ser Gly Thr Thr His Tyr His Val Glu Leu
                85                  90                  95
```

```
Glu Arg Glu Leu Ala Asp Leu His Gly Lys Glu Ala Ala Leu Leu Phe
            100                 105                 110

Thr Ser Gly Tyr Val Ser Asn Glu Ala Thr Leu Ser Thr Leu Tyr Lys
            115                 120                 125

Ile Leu Pro Gly Leu Val Val Phe Ser Asp Ala Leu Asn His Asn Ser
            130                 135                 140

Met Ile Ser Gly Ile Arg Ala Gly Lys Arg Glu Gln Arg His Val Phe
145                 150                 155                 160

Arg His Asn Asp Leu Ala His Leu Glu Glu Leu Leu Ala Ala Ala Asp
                165                 170                 175

Pro Ala Ala Pro Lys Leu Ile Ala Phe Glu Ser Val Tyr Ser Met Asp
            180                 185                 190

Gly Asp Ile Ala Asp Leu Pro Ala Met Val Ala Leu Ala Arg Lys Tyr
            195                 200                 205

Gly Ala Met Thr Tyr Leu Asp Glu Val His Ala Val Gly Met Tyr Gly
210                 215                 220

Pro Arg Gly Ala Gly Val Ala Glu Arg Asp Gly Val Met Asp Gln Ile
225                 230                 235                 240

Asp Ile Val Glu Gly Thr Leu Gly Lys Ala Phe Gly Val Met Gly Gly
                245                 250                 255

Tyr Ile Ala Ala Asp Ala Val Ile Val Asp Ala Ile Arg Ser Tyr Ala
            260                 265                 270

Asp Gly Phe Ile Phe Thr Thr Ser Leu Pro Pro Ala Leu Ala Ala Gly
            275                 280                 285

Ala Ala Ala Ser Ile Arg Trp Leu Lys Glu His Asp Glu Val Arg Gln
290                 295                 300

Ala His Gln Glu Arg Ala Ala Thr Leu Lys Ala Lys Met Arg Ala Ala
305                 310                 315                 320

Gly Leu Pro Val Met Asp Ser Val Ser His Ile Val Pro Val Leu Val
                325                 330                 335

Gly Asp Pro Val His Cys Lys Met Ile Ser Asp Ile Leu Leu Glu Asp
            340                 345                 350

His Gly Ile Tyr Val Gln Pro Ile Asn Phe Pro Thr Val Pro Arg Gly
            355                 360                 365

Thr Glu Arg Leu Arg Phe Thr Pro Ser Pro Ala His Thr Asp Ala Met
370                 375                 380

Met Asp Ala Leu Val Ala Ala Leu Glu Thr Leu Trp Val Arg Cys Asn
385                 390                 395                 400

Val Val Arg Val Gly Gly Met Ala Ala
                405

<210> SEQ ID NO 40
<211> LENGTH: 408
<212> TYPE: PRT
<213> ORGANISM: Caulobacter crescentus

<400> SEQUENCE: 40

Met Asp Tyr Lys Ala Ala Phe Arg Ser Ala Val Glu Gln Ile Arg Glu
1               5                   10                  15

Glu Gly Arg Tyr Arg Val Phe Ala Asp Leu Lys Arg Gln Arg Gly Gln
            20                  25                  30

Phe Pro Arg Ala Thr Trp Thr Arg Gln Asp Gly Ser Glu His Glu Val
            35                  40                  45

Val Val Trp Cys Ser Asn Asp Tyr Leu Gly Gln Gly Gln Asn Pro Val
        50                  55                  60
```

-continued

Val Leu Glu Ala Met Lys Ala Ala Val Asp Glu His Gly Ser Gly Ser
65 70 75 80

Gly Gly Thr Arg Asn Ile Ser Gly Thr Asn His Asp His Val Leu Leu
85 90 95

Glu Gln Glu Leu Ala Asp Leu His Gly Lys Glu Ala Gly Leu Leu Phe
100 105 110

Thr Ser Gly Tyr Val Ser Asn Glu Ala Thr Leu Ser Val Val Gln Lys
115 120 125

Ile Leu Pro Gly Leu Ile Ile Phe Ser Asp Glu Leu Asn His Ala Ser
130 135 140

Met Ile Ala Gly Ile Arg Asn Gly Gly Gly Pro Arg Lys Ile Phe Lys
145 150 155 160

His Asn Asp Leu Ala His Leu Glu Gln Leu Leu Ala Glu Ala Pro Ala
165 170 175

Asp Ala Pro Lys Leu Ile Ala Phe Glu Ser Val Tyr Ser Met Asp Gly
180 185 190

Asp Ile Ala Asp Leu Ala Gly Thr Val Ala Leu Ala Lys Lys Tyr Gly
195 200 205

Ala Met Thr Tyr Leu Asp Glu Val His Ala Val Gly Met Tyr Gly Pro
210 215 220

Arg Gly Gly Gly Val Ala Glu Arg Asp Gly Leu Met Gly Glu Ile Asp
225 230 235 240

Ile Ile Glu Gly Thr Leu Gly Lys Ala Phe Gly Val Met Gly Gly Tyr
245 250 255

Ile Thr Gly Asp Ala Glu Val Ile Asp Ala Ile Arg Leu Met Ala Ser
260 265 270

Gly Phe Ile Phe Thr Thr Ser Leu Pro Pro Ala Leu Thr Ala Gly Ala
275 280 285

Leu Ala Ser Val Arg Trp Leu Lys Gln His Pro Glu Val Arg Glu Ile
290 295 300

His Gln Glu Arg Ala Ala Thr Leu Lys Ala Met Phe Lys Ala Ala Gly
305 310 315 320

Leu Pro Val Met Asp Ser Val Ser His Ile Val Pro Val Leu Val Gly
325 330 335

Asp Pro Val His Cys Lys Met Ile Ser Asp Met Leu Leu Ala Asp Phe
340 345 350

Gly Val Tyr Val Gln Pro Ile Asn Tyr Pro Thr Val Pro Arg Gly Thr
355 360 365

Glu Arg Leu Arg Phe Thr Pro Thr Pro Phe His Thr Asp Asp Met Met
370 375 380

Arg Lys Leu Val Ala Ala Met Glu Lys Leu Trp Ala His Cys Asn Val
385 390 395 400

Ala Arg Met Gly Gly Tyr Ala Ala
405

<210> SEQ ID NO 41
<211> LENGTH: 401
<212> TYPE: PRT
<213> ORGANISM: Candidatus Liberibacter asiaticus str. psy62

<400> SEQUENCE: 41

Met Asp Phe Glu Lys Phe Phe Lys Asp Gln Ile Asn Tyr Leu His His
1 5 10 15

Glu Lys Arg Tyr Arg Phe Phe Thr Glu Leu Ala Tyr Glu Gln Tyr Gln
20 25 30

Phe Pro Tyr Ala Ile His Asn Ser Asp Glu Gly Ser Arg Lys Val Thr
         35                  40                  45

Ile Trp Cys Ser Asn Asp Tyr Leu Gly Met Gly Lys His Pro Lys Val
 50                  55                  60

Ile Glu Asn Ala Gln Arg Thr Phe Glu Lys Cys Gly Ile Gly Ala Gly
 65                  70                  75                  80

Gly Thr Arg Asn Ile Ala Gly Thr Asn Tyr Tyr His Val Met Leu Glu
                 85                  90                  95

Lys Glu Leu Ala Thr Leu His Gly Lys Lys Ala Ala Leu Ile Phe Asn
                 100                 105                 110

Ser Gly Tyr Ile Ala Asn Trp Ala Thr Ile Gly Thr Leu Cys Ser Gln
             115                 120                 125

Ile Asp Asn Ile Ile Cys Phe Ser Asp Ser His Asn His Ala Ser Ile
130                 135                 140

Ile Glu Gly Ile Asn Lys Ala Arg Cys Lys Lys Val Ile Trp Asn His
145                 150                 155                 160

Asn Asp Leu Glu Asp Leu Glu Lys Asn Leu Ala Ala Thr Asp Leu Ser
                 165                 170                 175

Ile Pro Lys Ile Ile Phe Glu Ser Ile Tyr Ser Met Asp Gly Asp
             180                 185                 190

Ile Ala Pro Ile Lys Glu Ile Cys Asp Leu Ala Asp Gln Tyr Asn Ala
             195                 200                 205

Ile Thr Tyr Ile Asp Glu Val His Ala Val Gly Ile His Gly Ser Cys
210                 215                 220

Gly Ala Gly Ile Ser Glu Arg Glu Gly Ile Met Asn Arg Ile Thr Ile
225                 230                 235                 240

Ile Ser Gly Thr Leu Ala Lys Gly Phe Gly Thr Phe Gly Gly Tyr Ile
                 245                 250                 255

Ala Ala Ser Glu Asn Leu Cys Asp Phe Ile Arg Ser Phe Ala Ser Gly
             260                 265                 270

Phe Ile Phe Ser Thr Ser Leu Pro Pro Ala Ile Ala Ser Ala Ser Val
         275                 280                 285

Thr Ser Ile Gln Tyr Ile Lys Gln His Tyr Asp Glu Arg Lys Lys Tyr
290                 295                 300

Leu Glu Arg Val Lys Gln Leu Arg His Ser Leu Glu Asn Lys Ala Ile
305                 310                 315                 320

Pro Cys Ile Pro Asn Glu Ser His Ile Ile Pro Ile Met Val Gly Asp
                 325                 330                 335

Ser His Lys Cys Thr Gln Ile Ser Asn Ile Leu Lys Glu Phe Gly
             340                 345                 350

Ile Tyr Ile Gln Pro Ile Asn Tyr Pro Thr Val Ala Lys Lys Glu
         355                 360                 365

Arg Leu Arg Val Thr Leu Thr Pro Leu His Thr Asp Ser Asp Ile Glu
370                 375                 380

His Leu Val Ser Ser Leu Glu Asn Val Trp Gln Lys Met Asn Arg Tyr
385                 390                 395                 400

Ala

<210> SEQ ID NO 42
<211> LENGTH: 406
<212> TYPE: PRT
<213> ORGANISM: Neorickettsia risticii str. Illinois

<400> SEQUENCE: 42

Met Ser Asn Tyr Ser Gly Val Phe Ala Gln Ala Leu Asp Thr Ile Lys

```
              1               5               10              15
Asn Glu Lys Arg Tyr Arg Glu Phe Val Asn Leu Ala Arg Ile Ser Gly
                20                  25                  30

Glu Phe Pro Cys Ala Ile Asn Glu Glu Thr Asn Glu Lys Ile Val Ile
                35                  40                  45

Trp Cys Ser Asn Asp Tyr Leu Gly Met Gly Gln Asn Phe Thr Val Cys
                50                  55                  60

Asp Ser Met Lys Glu Thr Ile Asp Arg Met Gly Ala Gly Ala Gly Gly
 65                  70                  75                  80

Thr Arg Asn Ile Ser Gly Asn Asn Lys Glu Val Val Leu Leu Glu Lys
                    85                  90                  95

Thr Ile Ala Arg Leu His Gln Lys Glu Ala Ala Leu Ser Phe Val Cys
                100                 105                 110

Gly Tyr Val Ala Asn Leu Ala Ser Ile Ser Thr Ile Ile Ser Leu Met
                115                 120                 125

Lys Asp Cys Ile Ala Phe Ser Asp Gln Cys Asn His Ser Ser Ile Ile
                130                 135                 140

Glu Gly Ile Arg Ser Ser Arg Cys Glu Lys Arg Ile Phe Arg His Asn
145                 150                 155                 160

Asp Val Asn His Leu Glu Glu Leu Leu Ser Gln Val Pro Arg Glu Ala
                165                 170                 175

His Lys Ile Ile Ile Phe Glu Ser Val Tyr Ser Met Asp Gly Asp Val
                180                 185                 190

Ala Pro Ile Lys Glu Ile Cys Asp Leu Ala Glu Lys Tyr Asn Ala Leu
                195                 200                 205

Thr Tyr Ile Asp Glu Val His Ala Val Gly Met Tyr Gly Arg His Gly
                210                 215                 220

Gly Gly Ile Thr Glu Glu Met Asp Leu Val Asp Arg Val Asp Ile Ile
225                 230                 235                 240

Gln Gly Thr Leu Ala Lys Ala Tyr Gly Val Ile Gly Gly Tyr Ile Ala
                245                 250                 255

Ala Lys Ala Asp Ile Ile Asp Val Val Arg Ser His Ala Ser Gly Phe
                260                 265                 270

Ile Phe Thr Thr Ala Leu Pro Pro Val Ile Ala Ser Ala Gly Arg Ala
                275                 280                 285

Ser Ile Thr His Leu Tyr Asp Ser Asn Glu Glu Arg Lys Gln Lys
                290                 295                 300

Glu Asn Val Ala Lys Leu Lys Ala Met Phe Lys Ala Asn Ser Ile Pro
305                 310                 315                 320

Tyr Lys Asp Ala Pro Thr His Ile Ile Pro Val Ile Ile Gly His Pro
                325                 330                 335

Glu Glu Cys Lys Tyr Ala Ser Gln Thr Leu Leu Glu Glu Phe Lys Ile
                340                 345                 350

Phe Ile Gln His Ile Asn Tyr Pro Thr Val Pro Arg Gly Thr Glu Arg
                355                 360                 365

Leu Arg Ile Thr Pro Thr Pro Gln His Thr His Thr Met Met Glu Glu
                370                 375                 380

Leu Val Phe Ala Leu Lys Glu Val Leu Gly Arg Ile Gln His Lys Lys
385                 390                 395                 400

Ser Ala Arg Gly Ala Val
                405

<210> SEQ ID NO 43
<211> LENGTH: 425
```

```
<212> TYPE: PRT
<213> ORGANISM: Brucella microti CCM 4915

<400> SEQUENCE: 43
```

| | | | | | | | | | | | | | | |
|---|---|---|---|---|---|---|---|---|---|---|---|---|---|---|
| Met | Asp | Tyr | Arg | Arg | Phe | Phe | Glu | Glu | Ala | Ile | Asp | Gln | Leu | His | Ala |
| 1 | | | | 5 | | | | | 10 | | | | | 15 | |

Glu Lys Arg Tyr Arg Val Phe Ala Asp Leu Glu Arg Ile Val Gly Arg
            20                  25                  30

Phe Pro Gln Ala Ile Trp Arg Asn Asn Gly Thr Ala Arg Glu Ile Thr
        35                  40                  45

Val Trp Cys Ser Asn Asp Tyr Leu Gly Met Gly His His Pro Asp Val
 50                  55                  60

Ile Lys Ala Met Cys Glu Thr Ala Gly Ser Ala Gly Ser Gly Ala Gly
65                  70                  75                  80

Gly Thr Arg Asn Ile Ser Gly Asn Asn His Pro Leu Val Glu Leu Glu
                85                  90                  95

Ser Glu Leu Ala Asp Leu His Gly Lys Glu Ala Gly Leu Val Phe Thr
            100                 105                 110

Ser Gly Phe Val Ser Asn Glu Ala Ser Ile Ser Thr Ile Ala Arg Leu
        115                 120                 125

Leu Pro Asn Cys Leu Ile Leu Ser Asp Glu Leu Asn His Ala Ser Met
130                 135                 140

Ile Glu Gly Val Arg Arg Ser Gly Ala Glu Lys Lys Ile Phe Arg His
145                 150                 155                 160

Asn Asp Val Glu His Leu Glu Gln Leu Leu Lys Ala Ala Asp Arg Ser
                165                 170                 175

Arg Ala Lys Leu Ile Val Phe Glu Ser Val Tyr Ser Met Asp Gly Asp
            180                 185                 190

Ile Ala Pro Ile Glu Lys Ile Ala Asp Leu Ala Asp Lys Tyr Asn Ala
        195                 200                 205

Met Thr Tyr Ile Asp Glu Val His Ala Val Gly Met Tyr Gly Ala His
210                 215                 220

Gly Gly Gly Ile Thr Glu Arg Asp Gly Leu Ala His Arg Ile Asp Ile
225                 230                 235                 240

Ile Glu Gly Thr Leu Ala Lys Ala Phe Gly Ala Leu Gly Gly Tyr Ile
                245                 250                 255

Thr Gly Ser Arg Ala Ile Ile Asp Ala Val Arg Ser Tyr Ala Pro Gly
            260                 265                 270

Phe Ile Phe Thr Thr Ser Leu Pro Pro Ala Val Ala Ala Ala Ala Thr
        275                 280                 285

Ala Ala Ile Arg His Leu Lys Ser Ser Gln Ala Glu Arg Asp Gly Gln
290                 295                 300

Gln Arg Gln Ala Gln Arg Ala Lys Asp Val Leu Ser Ala Ala Gly Leu
305                 310                 315                 320

Pro Val Met Pro Ser Gln Thr His Ile Val Pro Ile Leu Val Gly Asp
                325                 330                 335

Pro Glu Leu Cys Lys Lys Ala Ser Asp Arg Leu Leu Glu Val His Gly
            340                 345                 350

Ile Tyr Ile Gln Pro Ile Asn Tyr Pro Thr Val Pro Arg Gly Thr Glu
        355                 360                 365

Arg Leu Arg Ile Thr Pro Ser Pro Leu His Asp Asp Lys Leu Ile Asp
370                 375                 380

Gly Leu Lys Asp Ala Leu Leu Glu Val Trp Asn Glu Leu Gly Ile Pro
385                 390                 395                 400

Phe Ala Glu Pro Ser Ala Pro Gln Ala Asn Ser Asp Arg Ile Ile
                405                 410                 415

Pro Leu Met Val Ser Lys Ala Gly Gly
            420                 425

<210> SEQ ID NO 44
<211> LENGTH: 403
<212> TYPE: PRT
<213> ORGANISM: Chromobacterium violaceum

<400> SEQUENCE: 44

Met Ser Thr Asp Asn Ala Thr Ile Glu Leu Asn Leu Asp Arg Glu Leu
1               5                   10                  15

Arg Val Leu Phe Glu Asp Arg Leu Thr Gln Leu Lys Ser Glu Gly Leu
            20                  25                  30

Tyr Arg Ser Phe Met Pro Cys Glu His Asp Ala Ser His Pro Gly Thr
        35                  40                  45

Thr Arg Tyr Arg Gln Arg Gln Val Glu Val Trp Cys Ser Asn Asp Tyr
    50                  55                  60

Leu Gly Leu Ser Gln Asp Pro Gln Val Ile Glu Arg Leu Arg Glu Ser
65                  70                  75                  80

Ala Ala Leu His Gly Ser Gly Thr Gly Ser Arg Asn Ile Ala Gly
                85                  90                  95

Thr Ser Ile Ser His Val Glu Leu Glu Arg Gln Leu Ala Gln Trp His
            100                 105                 110

Gly Lys Glu Gln Ala Leu Val Phe Asn Gly Gly Tyr Thr Ala Asn Phe
        115                 120                 125

Glu Phe Leu Ser Thr Leu Ile Ala Ala Val Pro Asp Met Ala Ile Phe
    130                 135                 140

Ser Asp Ser Leu Asn His Arg Ser Leu Ile Glu Gly Ile Arg Arg His
145                 150                 155                 160

Pro Cys Gln Lys Phe Ile Phe Pro His Asn Asp Val Glu Thr Leu Glu
                165                 170                 175

Lys Gln Leu Ala Ser Val Pro Leu Ser Gln Pro Lys Leu Ile Val Phe
            180                 185                 190

Glu Ser Ile Tyr Ser Met Asp Gly Asp Ile Ala Pro Ile Gln Val Ile
        195                 200                 205

Leu Asp Leu Ala Asp Arg Tyr Gln Ala Trp Thr Phe Leu Asp Glu Thr
    210                 215                 220

His Ala Ile Gly Leu Tyr Gly Gly Ser Gly Ala Gly Leu Cys Glu Glu
225                 230                 235                 240

Ile Glu Glu Thr Arg Ala Thr Phe Ile Gln Gly Val Phe Gly Lys Ala
                245                 250                 255

Met Gly Thr Leu Gly Gly Tyr Ile Ala Gly Pro Ala Ser Val Val Asp
            260                 265                 270

Phe Val Arg Ser Ser Ala Pro Gly Phe Ile Phe Thr Thr Ala Leu Pro
        275                 280                 285

Gln Ala Leu Leu Asp Ala Thr Leu Cys Ser Phe Glu Arg Val Arg Glu
    290                 295                 300

Asp Arg Gln Leu Val Gln Asp Leu His Ser Asn Val Ile Phe Phe Arg
305                 310                 315                 320

Ala Gln Leu Asp Ala Ala Gly Ile Pro Tyr Leu Pro Ala Gln Ser His
                325                 330                 335

Leu Val Leu Val Pro Val Ala Gly Ala Glu Arg Ile Lys Thr Val Ala
            340                 345                 350

```
Arg Arg Leu Leu Glu Glu Phe Asp Ile Tyr Val Gln Pro Ile Asn Tyr
        355                 360                 365

Pro Ser Val Pro Arg Gly Gly Glu Arg Phe Arg Leu Thr Val Gly Pro
370                 375                 380

Arg Arg Ser His Glu Glu Ile Gln Arg Phe Val Ala Ala Leu Lys His
385                 390                 395                 400

Cys Leu Ala

<210> SEQ ID NO 45
<211> LENGTH: 425
<212> TYPE: PRT
<213> ORGANISM: Brucella abortus

<400> SEQUENCE: 45

Met Asp Tyr Arg Arg Phe Phe Glu Glu Ala Ile Asp Gln Leu His Ala
1               5                   10                  15

Glu Lys Arg Tyr Arg Val Phe Ala Asp Leu Glu Arg Ile Val Gly Arg
            20                  25                  30

Phe Pro Gln Ala Ile Trp Arg Asn Asn Gly Thr Ala Arg Glu Ile Thr
        35                  40                  45

Val Trp Cys Ser Asn Asp Tyr Leu Gly Met Gly His His Pro Asp Val
50                  55                  60

Ile Lys Ala Met Cys Asp Thr Ala Gly Ser Ala Gly Ser Gly Ala Gly
65                  70                  75                  80

Gly Thr Arg Asn Ile Ser Gly Asn Asn His Pro Leu Val Glu Leu Glu
                85                  90                  95

Ser Glu Leu Ala Asp Leu His Gly Lys Glu Ala Gly Leu Val Phe Thr
            100                 105                 110

Ser Gly Phe Val Ser Asn Glu Ala Ser Ile Ser Thr Ile Ala Arg Leu
        115                 120                 125

Leu Pro Asn Cys Leu Ile Leu Ser Asp Glu Leu Asn His Ala Ser Met
130                 135                 140

Ile Glu Gly Val Arg Arg Ser Gly Ala Glu Lys Lys Ile Phe Arg His
145                 150                 155                 160

Asn Asp Val Glu His Leu Glu Gln Leu Leu Lys Ala Ala Asp Arg Ser
                165                 170                 175

Arg Ala Lys Leu Ile Val Phe Glu Ser Val Tyr Ser Met Asp Gly Asp
            180                 185                 190

Ile Ala Pro Ile Glu Lys Ile Ala Asp Leu Ala Asp Lys Tyr Asn Ala
        195                 200                 205

Met Thr Tyr Ile Asp Glu Val His Ala Val Gly Met Tyr Gly Ala His
210                 215                 220

Gly Gly Gly Ile Thr Glu Arg Asp Gly Leu Ala His Arg Ile Asp Ile
225                 230                 235                 240

Ile Glu Gly Thr Leu Ala Lys Ala Phe Gly Ala Leu Gly Gly Tyr Ile
                245                 250                 255

Thr Gly Ser Arg Ala Ile Ile Asp Ala Val Arg Ser Tyr Ala Pro Gly
            260                 265                 270

Phe Ile Phe Thr Thr Ser Leu Pro Pro Ala Val Ala Ala Ala Ala Thr
        275                 280                 285

Ala Ala Ile Arg His Leu Lys Ser Ser Gln Ala Glu Arg Asp Gly Gln
290                 295                 300

Gln Arg Gln Ala Gln Arg Ala Lys Asp Val Leu Ser Ala Ala Gly Leu
305                 310                 315                 320

Pro Val Met Pro Ser Gln Thr His Ile Val Pro Ile Leu Val Gly Asp
```

```
                    325                 330                 335
Pro Glu Leu Cys Lys Lys Ala Ser Asp Arg Leu Leu Glu Val His Gly
                340                 345                 350

Ile Tyr Ile Gln Pro Ile Asn Tyr Pro Thr Val Pro Arg Gly Thr Glu
                355                 360                 365

Arg Leu Arg Ile Thr Pro Ser Pro Leu His Asp Asp Lys Leu Ile Asp
                370                 375                 380

Gly Leu Lys Asp Ala Leu Leu Glu Val Trp Asn Glu Leu Gly Ile Pro
385                 390                 395                 400

Phe Ala Glu Pro Ser Ala Pro Gln Ala Ala Asn Ser Asp Arg Ile Ile
                405                 410                 415

Pro Leu Met Val Ser Lys Ala Gly Gly
                420                 425

<210> SEQ ID NO 46
<211> LENGTH: 356
<212> TYPE: PRT
<213> ORGANISM: Staphylococcus aureus

<400> SEQUENCE: 46

Met Phe Cys Ser Asn Asp Tyr Leu Gly Met Ser Gln Asn Gln Glu Val
1               5                   10                  15

Ile Asn Val Met Gly Asp Ala Leu Lys Glu Tyr Gly Ala Gly Ala Gly
                20                  25                  30

Gly Ser Arg Asn Ile Gly Gly Ser His Lys Tyr Phe Lys Leu Leu Glu
                35                  40                  45

Asn Glu Ile Ala Lys Trp His Lys Lys Asp Ser Ala Leu Val Phe Pro
50                  55                  60

Thr Gly Tyr Ser Ser Asn Asp Ala Ser Leu Gln Gly Leu Leu Arg Ile
65                  70                  75                  80

Phe Pro Glu Met Ile Val Phe Ser Asp Ser Lys Asn His Ala Ser Ile
                85                  90                  95

Ile Asn Ala Leu Arg Ser Val Lys Asn Lys Ile Glu Ile Phe Glu His
                100                 105                 110

Asn Asn Val Lys His Leu Asn Glu Leu Leu Asn Gln Tyr Asp Ile Asn
                115                 120                 125

Thr Pro Lys Leu Ile Val Phe Glu Ser Val Tyr Ser Met Asp Gly Asp
                130                 135                 140

Ile Ala Pro Ile Val Glu Ile Val Glu Leu Ala Lys Glu Tyr Asn Ser
145                 150                 155                 160

Leu Thr Phe Leu Asp Glu Val His Ala Ile Gly Met Tyr Gly Glu Glu
                165                 170                 175

Gly Arg Gly Tyr Ser Asp Val Val Gly Val Gln Glu Asp Ile Asp Ile
                180                 185                 190

Ile Gln Ser Thr Met Ala Lys Gly Ile Gly Ile Gly Gly Tyr Ile
                195                 200                 205

Thr Gly Asp Gln Leu Leu Ile Asp Val Ile Arg Ser Tyr Ser Ser Gly
                210                 215                 220

Phe Ile Phe Thr Thr Ala Leu Pro Pro Val Ile Ala Ala Gly Cys Leu
225                 230                 235                 240

Thr Ser Ile Lys Ile Val Arg Ser Asn Asp Lys Leu Arg Glu Glu Leu
                245                 250                 255

Gln Asp Lys Thr Lys Tyr Leu Lys Glu Lys Phe Lys Glu Asn Gly Ile
                260                 265                 270

Glu Val Leu Lys Gln Ser Lys Thr His Ile Leu Pro Val Ile Ile Gly
```

```
                275                 280                 285
Asp Ser Lys Lys Cys Glu Glu Ala Ala Lys Leu Leu Leu Gly Lys Phe
    290                 295                 300

Asn Ile Tyr Asp Gln Ala Ile Asn Ser Pro Thr Val Glu Ile Gly Thr
305                 310                 315                 320

Glu Arg Phe Arg Ile Asn Val Thr Pro Asn His Thr Lys Glu Gln Met
                325                 330                 335

Asp Leu Leu Val Ser Ser Ile Val Tyr Val Phe Asp Phe Leu Asn Ile
                340                 345                 350

Arg Arg Ser Val
        355

<210> SEQ ID NO 47
<211> LENGTH: 406
<212> TYPE: PRT
<213> ORGANISM: Neorickettsia sennetsu str. Miyayama

<400> SEQUENCE: 47

Met Ser Asn Tyr Ser Ser Val Phe Ala Arg Ala Leu Asp Thr Ile Lys
1               5                   10                  15

Asn Glu Lys Arg Tyr Arg Glu Phe Val Asn Leu Ala Arg Ile Ser Gly
                20                  25                  30

Glu Phe Pro Cys Ala Ile Asn Glu Thr Asn Glu Lys Ile Val Ile
            35                  40                  45

Trp Cys Ser Asn Asp Tyr Leu Gly Met Gly Gln Asn Phe Thr Val Cys
    50                  55                  60

Asp Ser Met Lys Glu Thr Ile Asp Arg Met Gly Ala Gly Ala Gly Gly
65                  70                  75                  80

Thr Arg Asn Ile Ser Gly Asn Asn Lys Glu Val Val Leu Leu Glu Lys
                85                  90                  95

Thr Ile Ala Lys Leu His Gln Lys Glu Ala Ala Leu Ser Phe Val Cys
            100                 105                 110

Gly Tyr Val Ala Asn Leu Ala Ser Ile Ser Thr Ile Ile Ser Leu Met
        115                 120                 125

Glu Asn Cys Ile Ala Phe Ser Asp Gln Tyr Asn His Ser Ser Ile Ile
130                 135                 140

Glu Gly Ile Arg Thr Ser Arg Cys Glu Lys Arg Ile Phe Arg His Asn
145                 150                 155                 160

Asp Val Asn His Leu Glu Lys Leu Leu Ser Gln Val Pro Lys Gly Ala
                165                 170                 175

Tyr Lys Ile Ile Ile Phe Glu Ser Val Tyr Ser Met Asp Gly Asp Val
            180                 185                 190

Ala Pro Ile Lys Lys Ile Cys Asp Leu Ala Glu Lys Tyr Asn Ala Leu
        195                 200                 205

Thr Tyr Ile Asp Glu Val His Ala Val Gly Met Tyr Gly Lys His Gly
    210                 215                 220

Gly Gly Ile Thr Glu Glu Met Asp Leu Val Asp Arg Val Asp Ile Ile
225                 230                 235                 240

Gln Gly Thr Leu Ala Lys Ala Tyr Gly Val Ile Gly Gly Tyr Ile Ala
                245                 250                 255

Ala Lys Ala Asp Ile Ile Asp Ile Ile Arg Ser His Ala Ser Gly Phe
            260                 265                 270

Ile Phe Thr Thr Ala Leu Pro Pro Val Ile Ala Ser Ala Gly Arg Ala
        275                 280                 285

Ser Ile Thr His Leu Tyr Asp Ser Asp Glu Glu Arg Arg Lys Gln Lys
```

```
                290                 295                 300
Glu Asn Val Ala Lys Leu Lys Ala Met Phe Lys Ala Asn Gly Ile Pro
305                 310                 315                 320

Tyr Lys Asp Ala Pro Thr His Ile Ile Pro Val Ile Ile Gly His Pro
                325                 330                 335

Glu Glu Cys Lys Tyr Ala Ser Lys Thr Leu Leu Glu Glu Phe Lys Ile
                340                 345                 350

Phe Ile Gln His Ile Asn Tyr Pro Thr Val Pro Arg Gly Thr Glu Arg
                355                 360                 365

Leu Arg Ile Thr Pro Thr Pro Gln His Thr Asp Thr Met Met Glu Glu
                370                 375                 380

Leu Val Phe Ala Leu Lys Glu Val Leu Gly Arg Ile Gln His Lys Lys
385                 390                 395                 400

Ser Ala Arg Gly Ala Ile
                405

<210> SEQ ID NO 48
<211> LENGTH: 726
<212> TYPE: DNA
<213> ORGANISM: Synechocystis PCC6803

<400> SEQUENCE: 48
atgagtgtca acttagcttc ccagttgcgg gaagggacga aaaaatccca ctccatggcg      60
gagaacgtcg gctttgtcaa atgcttcctc aagggcgttg tcgagaaaaa ttcctaccgt     120
aagctggttg gcaatctcta ctttgtctac agtgccatgg aagaggaaat ggcaaaattt     180
aaggaccatc ccatcctcag ccacatttac ttccccgaac tcaaccgcaa acaaagccta     240
gagcaagacc tgcaattcta ttacggctcc aactggcggc aagaagtgaa aatttctgcc     300
gctggccaag cctatgtgga ccgagtccgg caagtggccg ctacggcccc tgaattgttg     360
gtggcccatt cctacacccg ttacctgggg gatctttccg gcggtcaaat tctcaagaaa     420
attgcccaaa atgccatgaa tctccacgat ggtggcacag ctttctatga atttgccgac     480
attgatgacg aaaaggcttt taaaaatacc taccgtcaag ctatgaatga tctgcccatt     540
gaccaagcca ccgccgaacg gattgtggat gaagccaatg acgcctttgc catgaacatg     600
aaaatgttca cgaacttgaa aggcaacctg atcaaggcga tcggcattat ggtgttcaac     660
agcctcaccc gtcgccgcag tcaaggcagc accgaagttg gcctcgccac ctccgaaggc     720
taataa                                                               726

<210> SEQ ID NO 49
<211> LENGTH: 1224
<212> TYPE: DNA
<213> ORGANISM: Rhodobacter sphaeroides

<400> SEQUENCE: 49
atggactaca atctggcact cgataccgct ctgaaccggc tccataccga gggccggtac      60
cggaccttca tcgacatcga gcggcgcaag ggtgccttcc cgaaagccat gtggcgcaag     120
cccgacggga gcgagaagga atcaccgtc tggtgcggca acgactatct cggcatgggc     180
cagcatccgg tggtgctggg ggccatgcac gaggcgctgg attcgaccgg cgccgggtcg     240
ggcggcacgc gcaacatctc gggcaccacg ctctatcaca agcgcctcga ggccgagctc     300
gccgacctgc acggcaagga agcggcgctg gtcttctcgt cggcctatat cgccaacgac     360
gcgaccctct cgacgctgcc gcagctgatc ccggcctcg tcatcgtctc ggacaagttg     420
aaccacgctt cgatgatcga gggcatccgc cgctcgggca ccgagaagca catcttcaag     480
```

-continued

```
cacaatgacc tcgacgacct gcgccggatc ctgacctcga tcggcaagga ccgtccgatc    540
ctcgtggcct tcgaatccgt ctattcgatg gatggcgact tcggccgcat cgaggagatc    600
tgcgacatcg ccgacgagtt cggcgcgctg aaatacatcg acgaggtcca tgccgtcggc    660
atgtacggcc cccgcggcgg cggcgtggcc gagcgggacg ggctgatgga ccggatcgac    720
atcatcaacg ggacgctggg caaggcctat ggcgtgttcg gcggctatat cgcggcctcg    780
tcaaagatgt gcgacgcggt gcgctcctac gcgccgggct tcatcttctc gacctcgctg    840
ccgcccgtcg tggcggccgg tgcggcggcc tcggtgcgcc acctcaaggg cgatgtggag    900
ctgcgcgaga agcaccagac ccaggcccgc atcctgaaga tgcgcctcaa ggggctcggc    960
ctgccgatca tcgaccacgg ctcgcacatc gtgccggtcc atgtgggcga ccccgtgcac   1020
tgcaagatga tctcggacat gctgctcgag catttcggca tctatgtcca gccgatcaac   1080
ttcccgaccg tgccgcgcgg gaccgagcgg ctgcgcttca ccccgtcgcc cgtgcatgat   1140
tccggcatga tcgatcacct cgtgaaggcc atggacgtgc tctggcagca ctgtgcgctg   1200
aatcgcgccg aggtcgttgc ctga                                          1224
```

```
<210> SEQ ID NO 50
<211> LENGTH: 782
<212> TYPE: DNA
<213> ORGANISM: Artificial Sequence
<220> FEATURE:
<223> OTHER INFORMATION: HO-1 gene optimized for expression in  E. coli

<400> SEQUENCE: 50
aggaggtaaa acatatgcat caccaccacc atcacgaaaa cttatacttc caaggcagcg     60
taaatctggc atcgcaactg agagagggca ccaaaaagtc gcacagcatg gcggagaatg    120
tgggttttgt caagtgtttc ttgaagggtg ttgttgagaa gaacagctac cgtaaactgg    180
tcggtaatct gtattttgtc tacagcgcga tggaagagga aatggcgaag ttcaaggatc    240
atccgattct gtcccacatc tacttcccgg aactgaaccg taagcagtcc ctggaacagg    300
acctgcagtt ttactacggt agcaactggc gtcaggaagt gaaaatcagc gctgcaggcc    360
aagcttacgt ggaccgcgtg cgccaggttg cggcaaccgc accggagctg ctggtcgcac    420
acagctacac ccgttatctg ggtgatctgt ctggcggcca aatcctgaag aaaatcgcgc    480
agaacgcgat gaatctgcac gacggcggca ctgcctttta cgaatttgca gacattgacg    540
atgaaaaggc gttcaagaat acttaccgtc aagccatgaa cgacctgccg attgaccaag    600
ctaccgcgga acgtatcgtc gatgaagcga atgacgcgtt tgcgatgaat atgaaaatgt    660
tcaacgagct ggagggcaat ctgatcaaag cgatcggtat tatggtattc aatagcctga    720
cgcgccgtcg ctctcagggc agcaccgagg tgggtctggc aacgagcgaa ggctgactcg    780
ag                                                                   782
```